(12) United States Patent
Martin et al.

(10) Patent No.: US 6,746,695 B1
(45) Date of Patent: Jun. 8, 2004

(54) PHARMACEUTICAL PREPARATIONS OF BIOACTIVE SUBSTANCES EXTRACTED FROM NATURAL SOURCES

(75) Inventors: Michael Z. Martin, Laupahoehoe, HI (US); Mehdi Ashraf-Khorassani, Blacksburg, VA (US); Larry Taylor, Blacksburg, VA (US)

(73) Assignees: Armadillo Pharmaceuticals, Inc., Armocas, CA (US); Virginia Tech. Intellectual Properties, Inc., Blackburg, VA (US)

( * ) Notice: Subject to any disclaimer, the term of this patent is extended or adjusted under 35 U.S.C. 154(b) by 0 days.

(21) Appl. No.: 09/578,849

(22) Filed: May 26, 2000

Related U.S. Application Data

(63) Continuation-in-part of application No. 09/518,191, filed on Mar. 3, 2000, now abandoned, and a continuation-in-part of application No. 09/408,922, filed on Sep. 30, 1999, now abandoned.

(60) Provisional application No. 60/136,409, filed on May 27, 1999, provisional application No. 60/122,526, filed on Mar. 3, 1999, and provisional application No. 60/102,912, filed on Oct. 2, 1998.

(51) Int. Cl.$^7$ ............................................. A61K 35/78
(52) U.S. Cl. ....................... 424/734; 424/725; 424/773; 210/656; 210/690; 210/691; 210/692
(58) Field of Search ................................ 424/725, 734, 424/773; 210/656, 690, 691, 692

(56) References Cited

U.S. PATENT DOCUMENTS

| | | | |
|---|---|---|---|
| 4,148,928 A | 4/1979 | Sodini et al. | |
| 4,209,539 A | 6/1980 | Banigan et al. | |
| 4,985,265 A | 1/1991 | Duboc et al. | |
| 5,120,558 A | 6/1992 | Nguyen et al. | |
| 5,296,224 A | * 3/1994 | Schwabe | 424/195.1 |
| 5,440,055 A | * 8/1995 | Castor | 549/510 |
| 5,512,285 A | 4/1996 | Wilde | |
| 5,672,371 A | 9/1997 | d'Oosterlynck | |
| 5,750,709 A | * 5/1998 | Castor | 546/348 |
| 5,925,355 A | 7/1999 | Chatterjee et al. | |
| 5,962,043 A | 10/1999 | Jones et al. | |
| 6,007,823 A | 12/1999 | Abbott et al. | |
| 6,013,304 A | 1/2000 | Todd | |
| 6,245,364 B1 | 6/2001 | Jones et al. | |

FOREIGN PATENT DOCUMENTS

| | | |
|---|---|---|
| GB | 2 288552 | 10/1995 |
| WO | 95/26795 | 10/1995 |

OTHER PUBLICATIONS

Berger et al, J. Pharmaceutical Sciences, 83(3):281–286, 1994.*

Bejar et al, Int. J. Pharmacognosy 33(1):25–32, 1995.*

Lopez–Avila et al, J. High. Resol. Chromatogr. 20:555–559, 1997.*

Abad, MJ et al., Anti–inflammatory activity of some medicinal plant extracts from Venezuela. J. Ethnopharmacol1996 Dec;55(1):63–8.

Alarcon–Aguilara, FJ, et al., Study of the anti–hyperglycemic effect of plants used as antidiabetics. J. Ethnopharmacol 61 2:101–110 (1998).

Almeida CE et al., Analysis of anti–diarrheic effect of plants used in popular medicine. Rev Saude Publica 1995 Dec;29(6):428–33.

Alves KB, et al., Inhibition of aminopeptidase activity by aromatic and other cyclic compounds. Braz J Med Biol Res. 1992;25(11):1103–6.

Anesini C, et al., Screening of plants used in Argentine folk medicine for anti–microbial activity. J Ethnopharmacol. 1993 Jun;39(2):119–28.

Arletti, R, et al., Stimulating property of *Turnera diffusa* and *Pfaffia paniculata* extracts on the sexual behavior of male rats, Psychopharmacology (Berl). 1999 Mar;143(1):15–9.

Auterhoff, H et al., Constituents of the drug Damiana. Arch Pharm (Weinheim) 301:537–544(1968).

Ballot D, et al., The effects of fruit juices and fruits on the absorption of iron from a rice meal. Br J Nutr. 1987 May;57(3):331–43.

Batista IF et al., Primary structure of a Kunitz–type trypsin inhibitor from *Enteroloubium contorlisiliquum* seeds. Phytochemistry. 1996 Mar;41(4):1017–22.

Becerra JX, et al., Nuclear ribosomal DNA phylogeny and its implications for evolutionary trends in Mexican Bursera (Burseraceae) Am J Bot 1999 Jul;86(7):1047.

Bejar et al., International J. Pharmacognosy 33(1), 1995, pp. 25–32.

(List continued on next page.)

*Primary Examiner*—Francisco Prats
(74) *Attorney, Agent, or Firm*—Morrison & Foerster LLP

(57) ABSTRACT

This invention relates to methods of extracting and purifying bioactive substances from various plants and herbs. More specifically the invention relates to methods of extracting and separating bioactive substances from various plants and herbs, such as Kava root, Byrsonima species, *Aesculus californica, Crataegus mexicana, Simmondsia chinensis*, Pfaffia species, *Alternanthera repens*, Bursera species, Turnera species, Perezia species, *Heimia salicifolia*, Psidium species, Enterlobium species, *Ptychopetalum olacoides, Liriosma ovata*, and *Chaunochiton kappleri*, using supercritical fluid extraction and/or fluorocarbon solvent extract. The present invention further relates to separation of bioactive substances contained in extracts using packed column supercritical fluid chromatography or HPLC where dense gas with or without modifiers is the mobile phase. The present invention also relates to pharmaceutical preparations and dietary supplements which may be prepared with the extracted bioactive substances and use of such pharmaceutical preparations and dietary supplements to treat various human ailments.

21 Claims, 33 Drawing Sheets

OTHER PUBLICATIONS

Bianchi E, et al., Antitumor agents from *Bursera fagroides* (Burseraceae) (Beta–peltatin–A–methylether and 5' desemethoxy–beta–peltatin–Am–methylether) 1969 Jul; 32:2759–62.

Bianchi E, et al., Antitumor agents from *Bursera microphylla* (Burseraceae) I. Isolation and characterization of deoxypodophyllotoxin. J Pharm Sci 1968 Apr;57(4):696–7.

Bocek, BR, Ethnobotany of Costanoan Indians, California, based on collections by John P. Harrington. Econ Bot 38 1984 2:240–255.

Caceres A, et al., Plants used in Guatemala for the treatment of gastrointestinal disorders. 1. Screening of 84 plants against enterobacteria. J Ethnopharmacol. 1990 Aug;30(1):55–73.

Caceres A., et al., Plants used in Guatemala for the treatment of gastrointestinal disorders. 3. Confirmation of activity against enterobacteria of 16 plants. J Ethnopharmacol. 1993 Jan;38(1):31–8.

Caldwell, ME, Brewer, WR, Plants with potential to enhance significant tumor growth. Cancer Res 43 1983 12:5775–5777.

Carabez, A. et al., The action of the sesquiterpenic benzoquinone, perezone on electron transport in biological membranes. Arch Biochem Biophys. 1988 Jan;260(1):293–300.

Castr–Faria–Neto HC et al., Pro–inflammatory activity of enterolobin: a hemolytic protein purified from seeds of the Brazilian tree *Enterolobium contortisiliquum*. Toxicon. 1991;29(9):1143–50.

Cheng, JT et al., Hypoglycemic effect of guava juice in mice and human subjects. Am Chin Med. 1983;11(104):74–6.

Costa RH et al., Purification and partial characterization of *Enterolobium contortisiliquum* seed arylamidase. Braz J Med Bio Res. 1991;24(4):337–44.

de Sousa MV, et al, Enterolobin, a hemolytic protein from *Enterolobium contortisilquum* seeds (Leguminosae–Mimosaideae). Purification and characterization. An Acad Bras Cienc. 1989 Dec;61(4):405–12.

Diaz, JL, Ethnopharmacology of sacred psychoactive plants used by the Indians of Mexico. Ann Rev Pharmacol Toxicol 17:647–(1977).

Dimayuga, RE; Murillo, RF; Pantoja, ML, Traditional medicine of Baja, California, Sur (Mexico II). J Ethnopharmacol 20 3:209–222 (1987).

Enriquez, R. et al., Active components in Perezia roots. J Ethnopharmacol. 1980 Dec;2(4):389–93.

Evans, MA, Ecology and removal of introduced rhesus monkeys; Desecheo Island National Wildlife Refuge, Puerto Rico, PR Health Sci J 1989 Apr; 8(1):139–56.

Fontes W. et al., Determination of the amino acid sequence of the plant cytolysin enterolobin. Arch Biochem Biophys 1997 Nov 15;347(2):201–7.

Fowden, L; Smith, A, Newly Characterized amino acids from Aesculus california Phytochemistry 1968 7:809–819.

Giessler, C; Horton, T; Double–blind trial of herbal slimming pill. Lancet 1986 8504 461–(1986).

Gnan, SO, et al, Inhibition of *Staphylococcus aureus* by aqueous Goiaba extracts. J Ethnopharmacol 1999 Dec 15;68(1–3):103–8.

Ionescu F, et al., The structure of benulin, a new pentacyclic triterpene hemiketal isolated from *Bursera arida* (Burseraceae) J Org Chem 1977 Apr 29:42(9):1627–9.

Jairaj, P et al., Anti–cough and antimicrobial activities of *Psidium guajava* Linn. Leaf extract. J Ethnopharmacol. 1999 Nov 1;67(2):203–12.

Jolad SD, et al., Cytotoxic agents from *Bursera klugii* (Burseraceae) I: isolation of sapelins A and B.J Pharm Sci 1977 Jun: 66(6):889–90.

Jolad–SD, et al., Cytotoxic agents from *Bursera morelensis* (Burseraceae) deoxypodophyllotoxin and a new lignan, 5'–desmethoxydeoxypodophyllotoxin. J Pharm Sci 1977 Jun:66(6):892–3.

Kubo, I et al., Combined effect on plant growth of (–)–Epicatchin and Hydroquinone, compounds from *Aesculus californica* Nutt. Chem Pharm Bull 33 1985 9:3826–3828.

Kubo, I; Ying, BP, Phenolic constituents of California buckeye fruit. Phytochemistry 31 1992 11:37933–3794.

Le Grand A, [Anti–infective phytotherapies of the tree–savannah, Senegal (occidental Africa). III. A review of photochemical substances and the anti microbial activity of 43 species]. J Ethnopharmacol. 1989 May;25(3):315–38. Review. French.

Lema, WJ et al., Prostaglandin synthetase inhibition by alkaloids of *Heimia salifcifolia*. J Ethnopharmacol 1986 Feb;15(2):161–7.

Leon de Pinto G, et al., Chemical and 13C NMR studies of *Enterolobium cyclacarpum* gum and its degradation products. Phytochemistry. 1994 Nov;37(5):1311–5.

Lozoya X, et al., Quercetin glycosides in *Psidium guajava* L. leaves and determination of a spasmolytic principle. Arch Med Res. 1994 Spring;25(1):11–5.

Lutterodt GD, Inhibition of Microlax–induced experimental diarrhea with narcotic–like extracts of *Psidium guajava* leaf in rats. J Ethnopharmacol 1992 Sep;37(2):151–7.

Lutterodt GD, Inhibition of gastrointestinal release of acetylcholine by quercetin as a possible mode of action of *Psidium guajava* leaf extracts in the treatment of acute diarrheal disease. J Ethnopharmacol 1989 May;25(3):235–47.

Lutterodt GD et al., Effects on mice locomotor activity of a narcotic like principle from *Psidium guajava* leaves. J Ethnopharmacol. 1988 Dec;24(2–3):219–31.

Malone, MH, et al., *Heimia salicifolia*: a phytochemical and phytopharmacologic review. J Ethnopharmacol 1994 May:;42(3):135–59.

Matsuo, T et al., Identification of (+)–gallocatchin as a bio–anti–mutagenic compound in *Psidium guava* leaves. Phytochemistry 1994 Jul;36(4)1027–9.

Mazzanti, G, et al., Pharmacol Res 27 Anti–inflammatory activity of *Pfaffia paniculata* (Martius) Kuntze and *Pfaffia stenophylla* (Sprengel) Stuchl.1:91–92 (1993).

Mazzanti, G. Braghiroli, L, Analgesic and anti–inflammatory action of *Pfaffia paniculata* (Martius) Kuntze. Phtother Res 8 7:413–416(1994).

McDoniel PB, et al., Antitumor activity of *Bursera schlechtendalii* (burseraceae): isolation and structure determination of two new lignans. J Pharm Sci 1972 Dec;61(12):1992–4.

Morales MA, et al., Calcium–antagonist effect of quercetin and its relation with the spasmolytic properties of *Psidium guajava* L. Arch Med Res. 1994 Spring;25(1):17–21.

Nakal, S. et al., Pfaffosides, nortriterpnenoid sponins from *Pfassfica paniculata*. Phytochemistry 23 8:1703–1705 (1984).

Nascimento, SC, et al., Antimicrobial and cytotoxic activities in plants from Pernambuco, Brazil. Fitoterapia 61 4: 353–355 (1990).

Nishimoto, N; et al., Pfaffosides and nortriterpenoid saponins from *Pfaffia paniculata*. Phytochemistry 23 1:139–142(1984).

Obatomi, DK et al., Anti–diabetic properties of the African mistletoe in streptozotocin–induced diabetic rats. J Ethnopharmacol. 1994 Jun;43(1)13–7.

Oliva ML, et al., Serine–and SH–proteinase inhibitors from *Enterolobium contortisiliquum* beans. Purification and preliminary characterization. Braz J Med Biol Res. 1987;20(6):767–70.

Opute FI, The component fatty acids of *Psidium guajava* seed fats. 1978 Aug;29(8):737–8.

Peraza–Sanchez SR et al., Isolation of picropolygamain from the resin of *Bursera simaruba*. J Nat Prod 1992 Dec:55(12):1768–71. No abstract available.

Perez, RM et al., A study of the hypoglucemic effect of some Mexican plants. J Ethnopharmacol 12 3:253–262 (1984).

Ponce–Macotela M et al., [In vitro effect against Giardia of 14 plant extracts]. Rev Invest Clin. 1994 Sep-Oct;46(5):343–7. Spanish.

Proll J, et al., Low nutritional quality of unconventional tropical crop seeds in rats. J. Nutr. 1998 Nov;128(11):2014–22.

Rabe, T et al., Anti–bacterial activity of South African plants used for medicinal purporses. J Ethnopharmacol. 1997 Mar;56(1):81–7.

Re L, et al., Effects of some natural extracts on the acetylcholine release at the mouse neuromuscular junction. Pharmacol Res. 1999 Mar;39(3):239–45.

Riquelme BD et al., Complex viscoelasticity of normal and lectin treated erythrocytes using laser diffractometry. Biorheology 1998 Jul–Oct;35(4–5).

Roman–Ramos R, et al., Anti–hyperglycemic effect of some edible plants. J Ethnopharmacol. 1995 Aug 11;48(1)25–32.

Rother, A, The phenyl–and biphenyl–quinolizidines of in–vitro–grown *Heimia salificolia*. J Nat Prod 1985 Jan-Feb;48(1):33–41.

Sampaio CA et al., Action of plant proteinase inhibitors on enzymes of the kallikrein kinin system. Agents Actions Suppl. 1992;36:191–9.

Santos, FA et al., The leaf essential oil of *Psidium guyanensis* offers protection against pentylenetetrazole–induced seizures. Planta Med. 1997 Apr;63(2):133–5.

Schimmer, O; et al., An evaluation of 55 commercial plant extracts in the Ames mutagenicity test. Pharmazie 49 6: 448–451(1994) (Inst Bot Pharm Biol Univ Erlangen Nurnberg Germany).

Silva GA, et al., Isolation and partial characterization of an endopeptidase from *Enterolobium contortisiliquum* seeds. Braz J Med Biol Res. 1994 Jun;27(6):1299–310.

Sousa MV et al., Homology between the seed cytolysin enterlobin and bacterial aerolysins. J Protein Chem. 1994 Nov;13(8):659–67.

Spencer, KC; Seigler, DS, Tetraphyllin B from *Turnera diffusa*. Planta Med 43:175–178 (1981).

Subiza, J et al., Occupational asthma caused by Brazil ginseng dust, J. Allergy Clinic Immuno 88 5:731–736 (1991).

Takemoto, T, et al., Pfaffic acid, anovel nortritepene from *Pfaffia paniculata*. Tetrahedron Lett 24 10:1057–1060 (1983).

Tona L, et al., Anti–amoebic and phytochemical screening of some Congolese medicinal plants. J Ethnopharmacol. 1988 May ;61(1):57–65.

Trumbull, ER et al., Antitumor agents from *Bursera microphylla* (Burseraceae) 3. Synthesis of burseran. J Pharm Sc 1969 Feb; 58(2):176–8.

Wickramaratne, DB et al., Cytotoxic constituents of *Bersera permollis*. Planta Med. 1995 Fed;61(1):80–1.

Winkelman, M, Frequently used medicinal plants in Baja, California Norte. J Ethnopharmacol 18 2:109–131 (1986).

Zavala, MA, et al., Antidiarreheal activity of *Waltheria Americana*, *Commeline coelestis* and *Alternanthera repens*. J. Ethnopharmacol. 1998 May; 61(1):41–7.

R. Hansel, Characterization and Physiological Activity of Some Kava Constituents Pacific Science, Jul. 1968, vol. XXII: pp. 293–313.

* cited by examiner

PHARMACEUTICAL PREPARATIONS OF BIOACTIVE SUBSTANCES EXTRACTED FROM NATURAL SOURCES

CROSS REFERENCE TO RELATED APPLICATIONS

This application claims the benefit of provisional application No. 60/136,409, filed May 27, 1999. This application is a CIP of application Ser. No. 09/408,922, filed Sep. 30, 1999, now abandoned, which claimed the benefit of provisional application No. 60/102,912, filed Oct. 2, 1998. This application is also a CIP of application Ser. No. 09/518,191, filed Mar. 3, 2000, now abandoned, which claimed benefit of provisional application No. 60/122,526, filed Mar. 3, 1999.

BACKGROUND

1. Field of the Invention

This invention relates to methods of extracting and purifying bioactive substances from various plants and herbs. More specifically the invention relates to methods of extracting and separating bioactive substances from various plants and herbs using supercritical fluid extraction and/or fluorocarbon solvent extract. The present invention further relates to separation of bioactive substances contained in extracts using packed column supercritical fluid chromatography. The present invention also relates to formulations, pharmaceutical preparations and dietary supplements which may be prepared with the extracted bioactive substances and use of such pharmaceutical preparations and dietary supplements to treat various human ailments.

2. Description of the Background

Throughout history humans have ingested and otherwise consumed a wide variety of plants and herbs, and extracts of such plants and herbs to help alleviate aches and pains, improve immunity to infection, treat various illnesses, or even to induce relaxation or stress reduction.

One plant that has been commonly ingested by the people of the South Pacific to induce relaxation is called Kava Root. K. Schubel, J. Soc. Chem. Ind., 43, 766 (1924); A. G. Van Veen, Rec. Trav. Chim., 58, 52 (1939). Kava root consists of the dried rootstock and/or shoots of Piper methysticum Forst (Family: Piperaceae). The Kava root is most typically ingested by drinking an aqueous macerate (pulverized Kava root mixed with water) known as the beverage Kava.

First attempts to identify the active compounds within Kava root were made over a hundred years ago. Those efforts resulted in the identification of kavalactones, also known as kavapyrones. More than ten kavalactones as well as four other substances have been identified in the Kava root to date, including kavain, dihydrokavain (a.k.a. marindinin), methysticin, dihydromethysticin, yangonin, and desmethoxyyangonin. V. Lebot, M. Merling, and L. Lindstrom, "Kava the Pacific Drug", Yale University Press, New Haven, Conn. (1992). These compounds are neutral, nitrogen-poor compounds that may be specifically referred to as substituted d-lactones and substituted a-pyrones. The lactone ring is substituted by a methoxy group in the C3 position, and the differences in the compounds lie in the degree of unsaturation (e.g. yangonin, desmethyoxyyangonin, kavain and methysticin) or by bezene substitution (e.g. dihydrokavain and dihydromethysticin), as shown in FIG. 24.

The particular kavalactones in a Kava root extract vary depending upon its origin. Different species of kavalactones have been found to have varying physiological effects in vivo depending on their molecular structure. All naturally occurring kavalactones contain an enolic double bond between C3 and C4. The dienolides of the yangonin type appear to be pharmacologically inert. In the enolides, the effective optimum varies as a function of the hydrogenation of the double-bonded C7. For example, kavain has the strongest effect as a local anesthetic, dihydromethysticin as a spasmolytic, and dihydrokavain as an intensifier of narcosis. R. Hansel, Characterization and Physiological Activity of Some Kava Constituents Pacific Science, July 1968, Vol. XXII: pp293–313.

Further, the particular kavalactones present depend upon whether, in addition to rhizome parts, roots and stems of the plant are included in the extract. High quality extracts of the Kava root are sold based upon the total kavalactone content, rather than upon analysis of the individual lactones contained therein. The concentration ranges of total kavalactone levels in the Kava root extracts employed, e.g. in Germany are generally within the range of 30 to 55 weight percent.

Although many types of kavalactones have been identified, no simple and efficient method is available for both extraction of the root and separation of each individually extracted lactone. The traditional extraction method (e.g. steam distillation) usually involved mixing 100 grams of root with a suitable quantity of distilled water producing a slurry having a volume of approximately 200 mL. A. R. Furgiuele, W. J. Kinnard, M. D. Aceto, and J. P. Buckley, J. Pharmaceutical Sci., 54, 248 (1965). The slurry was steam distilled and the first 100 mL of distillate was collected, filtered and lyophilized. The yield for each extraction was about 50 mg. Alternately, a liquid-solid extraction at room temperature has been reported wherein the above slurry was intimately mixed in a Waring blender for 15 minutes. The mixture was then filtered and lyophilized. In certain cases, rather than lyophilization, the filtrate was subjected to successive extractions with chloroform. This purification operation basically removed impurities from the aqueous layer. The extraction yield for these methods varied depending on the solvent and methodology used.

Modern Kava root extracts are commonly manufactured using ethanol as a solvent because kavalactones are readily soluble in ethanol. The extractable materials are in the form of a yellowish brown paste or powder, which is then tested to assure proper concentrations of kavalactones.

A plant that has been commonly ingested by the people of Mexico and other Latin American countries is *Byrsonima crassifolia* (Nanche). The medicinal importance of this tropical tree, which is indigenous to Mexico, has been documented historically since the sixteenth century. Traditional healers use the plant to treat gastrointestinal disorders, especially diarrhea and dysentery.

To date, about 21 chemical substances have been extracted from the dried leaves and bark of the tree, including β-sitosterol and betulin (triterpenes), pipecolic acid and proline (amino acids), and catechin and quercetin (flavonoids). Béjar, E., et al., Constituents of *Byrsonima crassifolia* and their spasmogenic activity, Int. J. Pharmacog. 1995, 33:1, 25–32. The discovery of pipecolic acid is significant in that it is a rare compound in nature and is an important intermediate in a number of pharmacological preparations which demonstrate therapeutic effect for stroke, Parkinson's disease, Alzheimer's disease, and other neurological and vascular disorders. Prior to the discovery of pipecolic acid in *Byrsonima crassifolia*, preparations containing pipecolic acid were derived from various cultured micro-organisms.

Traditional healers prepared aqueous solutions of Byrsonima as teas. It was recently discovered that aqueous extracts of Byrsonima contain only catechin. However, when methanol is used to extract bioactive substances from Byrsonima, a wide variety of triterpenes, amino acids and flavonoids can be isolated.

Plants in the genera Aesculus and Crataegus are known to contain bioactive substances which affect the heart and circulatory system. Galenical preparations of, for example, *Crataegus oxyacantha, C. azarolus, C. monogyna, C. pentagyna, C. laevigata* and *C. nigra* have been used in European herbalism for centuries for these purposes. *Crataegus pinnatifida* has been used for similar purposes in Traditional Chinese Medicine for even longer. Likewise the use of *Aesculus hippocastanum* in Europe for the treatment of circulatory disorders is well documented. The effect has been attributed to aescin, a mixture of triterpene glycosides which have an anti-exudative and vascular tightening effect. While these European and Asian species have been the subject of a great deal of research, co-generic species endemic to the New World have been largely ignored. *Aesculus californica*, commonly known as 'California buckeye' in English and 'berruco' in Spanish, had been used by the native tribes and early colonists of California for a variety of purposes. The dried bark of the tree was used for toothaches, the fresh seeds were eaten after leaching out the bitter principles, and the unprocessed fruits were used to treat hemorrhoids, as a fish poison, and as an abortifacient.

Analyses of the seeds of *Aesculus californica* by several groups have revealed the presence of a number of known bioactive compounds: the proteids β-methyl alanine, phenylalanine, isohomoleucine, isohomo-6-hydroxyleucine, mino4-methyl-hex-tans-4-enoic acid and gamma-glutamyl-2-A-hex-4-enoic acid; the benzoids arbutin and hydroquinone; the flavonoid epicatechin; and the coumarin eleutheroside B-1, as well as the carbohydrate quebrachitol. This chemical profile differs from the European *A. hippocastanum*.

Extracts of Crataegus and Aesculus species are commonly prepared using various solvents, such as methanol, ethanol or acetone. The extracts are taken from the leaves and flowers of Crataegus species and from the seeds, leaves and bark of the Aesculus species.

The plant *Simmondsia chinensis*, also known as Jojoba, is native to the desert areas of the Southwestern United States and Mexico. Jojoba has a unique wax ester oil which is 50 to 60% of its seed weight. This oil is currently used in cosmetics and lubricants. The remainder of the seed is not used as much as the oil although it contains about 25% crude protein after the oil is removed. The defatted meal contains sugars and 11 to 15% of a unique group of natural products.

Simmondsin, one of the natural products contained in Jojoba meal, has been shown to be an effective hunger satiation agent by reducing food intake in mice, rats, and chickens. Cokeleare et al. (1995, Ind. Crops Prod., 4:91–96). Simmondsin has also been shown to be a useful weight reduction agent for Dogs. See U.S. Pat. No. 5,962,043. However, Jojoba meal also contains other antinutritional factors such as trypsin inhibitor, polyphenols, bitter taste, nonnutritive protein, and indigestible Jojoba oil.

Methods of removing so-called "toxic" principles from Jojoba seed meal in order to render it palatable to animals as feed have been described. See U.S. Pat. No. 5,672,371 to d'Oosterlynck, U.S. Pat. No. 4,209,534 to Banigan et al., and U.S. Pat. No. 4,148,928 to Sodini. Also, solvents have been used to extract simmondsins from Jojoba meal. U.S. Pat. No. 6,007,823.

*Pfaffia paniculata*, commonly called Brazilian ginseng, is a plant in the family Amaranthaceae which grows in parts of Brasil, Paraguay, Uruguay and Argentina. All parts of the plant are used in folk medicine, but it is the roots that are considered most valuable medicinally. Traditionally, the plant has been used to treat diabetes, rheumatism, ulcers, leukemia and other cancers, and as a tranquilizer, general tonic, and aphrodisiac.

Recent studies have demonstrated that the plant has biological activity as an anti-allergenic, analgesic, anti-inflammatory, antitumor agent, has a weak CNS-depressant effect and decreases vascular permeability. The plant has further been shown to be non toxic to humans.

Extracts of the plant have been shown to contain allantoin, daucosterol, b-ecdysone, pfaffic acid, pfaffosides A, B, C, D, E, and F, polypodine B, β-sitosterol, stigmasterol, and stigmasterol-3-O-β-D-glucoside.

*Turnera diffusa* and other Turnera species, commonly called damiana, hierba del venado, and other names, are small, herbaceous perennials ranging from California to South America. The plant has been used since pre-Columbian times as an aphrodisiac and sexual tonic, expectorant, diuretic, antidiabetic, to increase fertility, treat spermatorrhea, orchitis, nephritis, chronic coughing, and as a stimulant, digestive aid, and laxative. Laboratory tests of various Turnera preparations have shown cytotoxic and antihyperglycemic effects. The plant extract has been found to be non-mutagenic.

Turnera species are known to contain arbutin, caffeine, gonzalitosin, β-sitosterol, an acetovanillin-like benzenoid compound, hexacosan-1-ol, tetraphyllin B, N-triacontane, tricosan-2-one, an essential oil which contains 1-8-cineol, paracymene, a-pinene, b-pinene, and three sesquiterpenes.

The roots of plants of the genus Perezia produce perezone (2-(1,5-dimethyl-4-hexenyl)-3-hydroxymethyl-p-benzoquinone). Perezone is a sesquiterpenic benzoquinone which exhibits oxido-reduction characteristics. Certain species of the perezia genus have been used as laxatives in Mexican folk medicine.

In studies of the effect of perezone on electron transport in biological membranes, it was found that perezone inhibits mitochondrial electron transport in rat liver mitochondria differently than rotenone, amytal, and Antimycin A. Carabez A. et al., The Action of the Sesquiterpenic Benzoquinone, Perezone, on Electron Transport in Biological Membranes. Arch Biochem Biophys. 1988 January; 260(1):293–300. The low respiration of rat liver mitochondria depleted of coenzyme Q10 (CoQ) was shown to be increased by perezone.

*Heimia salicifolia* was used as a traditional medicine in the Americas to treat inflammation. In recent studies, two alkaloids from *Heimia salicifolia*, cryogenine and nesodine, were discovered to be more than twice as potent as aspirin as inhibitors of prostoglandin synthetase prepared from bovine seminal vesicles.

In-vitro-grown shoots of *Heimia salicifolia* have been found to be active in alkaloid biosynthesis, yielding the biphenylquinolizidine lactones vertine, lytrine, and lyfoline, the ester alkaloids demethoxyabresoline and epidemethoxylabresoline, the phenylquinolizidinols demethyllasubine-I and demethyllasubine-II. Rother, A., The phenyl- and biphenyl-quinolizidines of in-vitro-grown *Heimia salicifolia*. J. Nat. Prod. 1985 January–February; 48(1):3341. Five to ten day old seedlings of *Heimia salicifolia* have also been used to extract bioactive species. Two isomeric 2-hydroxy-4-(3-hydroxy4-methoxyphenyl)

quinolizidines, differing in the configuration of the bridgehead carbon, have been isolated by Rother, A. et al. Radioactive dilution has been used to isolate 2-keto-4-(3-hydroxy4-methoxyphenyl)quinolizidine from the seedlings.

Although these and many other plant species are known for various therapeutic and healing effects, these plants have further benefits, and synergistic effects when multiple plants are combined, that have not yet been described. The bioactive substances which make these plants medicinally effective are commonly extracted with solvents and/or water. This technology has several disadvantages among which are the cost of the solvents, costs associated with their safe disposal, and removal of the solvents from the extract.

Furthermore, medicinal plant chemistry is complex and the vast majority of medicinal plants owe their pharmacological action to many different molecular entities which often belong to more than one class of compounds. Many solvents have only a limited effectiveness for eluting certain classes of compounds, resulting in inefficient extractions. These types of extractions generally result in low concentrations of bioactive substances and a need for multiple extractions with different solvents to isolate differing substances.

An extraction method which removes high concentrations of multiple bioactive substances is desirable. A separation method which permits efficient separation of the substances to obtain purified, therapeutically effective quantities of bioactive substances is also desired. Such methods would provide new extracts from known plant species, the ability to isolate useful quantities of specific bioactive substances, new uses of extracts from known plant species, and more efficient extraction.

Supercritical fluid extraction and supercritical fluid chromatography have been used in the chemical arts for many years. Gases such as carbon dioxide or propane have proven to have excellent solvating properties when pressurized, particularly above their critical point This so-called supercritical region occurs when a gas is pressurized to a point where it would normally liquify, but is simultaneously heated above its now greatly reduced boiling point to prevent liquification. This "supercritical fluid" is neither a liquid nor a gas, but exhibits properties of both. In particular, supercritical fluids possess excellent solvating properties with high selectivity for particular analytes. This selectivity can be further adjusted by variations of pressure, temperature and use of mixed gases.

Lopez and Benedicto used supercritical $CO_2$ to extract kavalactones from Kava herb. V. Lopez-Avila and J. Benedicto, J. High Resolut. Chromatogr., 20, 555 (1997). In each extraction a 10 mL cartridge was filled with 2.5 grams of Kava herb which was extracted with both pure and 15% ethanol-modified $CO_2$ for a dynamic extraction time of 60 minutes at 250 atm and 60° C. Extracted analytes were collected in a vial filled initially with 4 mL of ethanol maintained at 22° C. Recovery was less than 25% when pure $CO_2$ was used as the extraction fluid, but was greater than 90% (relative to a solid-liquid extraction) when using 15% ethanol-modified $CO_2$. Identification of each of the extracted kavalactones was determined via GC/MS. Not only was the supercritical fluid extraction highly efficient, but there were very few co-extractives.

Although $CO_2$ proved generally effective for extraction of kavalactones, $CO_2$ only works as an extraction medium at extreme pressures, generally on the order of several thousands of pounds per square inch. This factor contributes to the high cost of equipment and to inherent dangers associated with extreme pressure vessels. Various types of chromatography have been used to separate and determine the major constituents of Kava extracts. Nakayama et al. used thin layer chromatography to separate and quantify six kavalactones (R. L. Young, J. W. Hylin, D. L. Plucknett, Y. Kawano, and R. T. Nakayama. Phytochemistry, 5, 795 (1966)). Later, Gracza et al. used normal phase high pressure liquid chromatography (HPLC) to separate a mixture of kavalactones (L. Gracza and P. Ruff, J. Chromatogr., 486, 193 (1980)). Haberlein et al. have also used normal phase HPLC to separate and quantify a series of kavalactones (H. Haberlein, G. Boonen, and M. A. Beck; Planta Med. 63, 63 (1997); G. Boonen, M. A. Beck, and H. Haberlein, J. Chromatogr. B, 702, 240 (1997)). Reverse phase HPLC was used to separate kavalactones, however, most of the separations were poor. R. M. Smith, H. Thakrar, T. A. Arowolo, and A. A. Shafi J. Chromatogr., 283, 303 (1984). Recently, Shao et al. used reverse phase HPLC with atmospheric pressure chemical ionization mass spectrometry in the positive ion mode to separate and identify specific kavalactones. Baseline separation of six lactones was achieved in less than 36 minutes. Y. Shao, K. He, B. Zheng, and Q. Zheng. J. Chromatogr. A, 825, 1 (1998).

Although some of these methods have proven fairly efficient for identifying, obtaining, separating, and isolating various kavalactones, improvements to the field are necessary. Additionally, a method for simply and accurately obtaining, separating and isolating different species of bioactive substances from other plant species are still lacking. Furthermore, in today's health conscious society, novel applications of natural source substances, and methods for obtaining such therapeutically useful substances, are necessary.

SUMMARY OF THE INVENTION

The present invention overcomes the problems and disadvantages associated with current strategies and designs and provides novel methods for extracting, separating, and isolating bioactive substances from natural sources. The present invention further relates to novel therapeutic uses of such extracts.

Accordingly, one embodiment of the invention is directed to methods for the preparative and/or commercial scale extraction of bioactive substances comprising the step of using supercritical fluid extraction (SFE) or near-critical extraction (NCE) for said preparative and/or commercial-scale extraction. The SFE or NCE may be accomplished with $CO_2$ or $CO_2$ modified with various other volatile substances. The SFE or NCE may further be accomplished as a batch-wise extraction, continuous-cascading extraction, or countercurrent-solvent extraction.

Another embodiment is directed to methods for the preparative and/or commercial scale processing of bioactive substances comprising coupling SFE or NCE and supercritical fluid chromatography (SFC), with or without modifiers, for said preparative and/or commercial scale processing. In this embodiment, isopropyl amine may be used as a modifier in SFC.

Another embodiment of the invention is directed to methods for the preparative and/or commercial scale extraction of bioactive substances comprising the step of using dense gases in the supercritical, near critical, or subcritical state with or without modifiers, for said preparative and/or commercial scale extraction. The dense gas may be any non-chlorinated fluorocarbon solvent and the modifiers may be any other volatile substance. The extraction may be performed under a pressure of 0–10 bar, or under supercritical or near critical fluid conditions. Dense gas extraction may further be accomplished as a batch-wise extraction, continuous-cascading extraction or countercurrent-solvent extraction Another embodiment of the invention is directed to methods for the separation of bioactive substances comprising the step of SFC. The step of using SFC preferably comprises the use of $HH_2$ and/or C4 columns, singly or in combination, in the SFC separation.

Another embodiment of the invention is directed to compositions comprising medicinal formulations of extracts of Byrsonima species recovered with supercritical fluid extraction and/or dense gases or with various organic solvents and/or water, and to methods of administering therapeutically effective amounts of these formulations to patents in need of treatment. Byrsonima species extracts are used alone or are combined with advantageous effect with various Psidium and Enterolobium species extracts, which are similarly prepared. Compositions may comprise extracts or isolated products of *Aesculus californica* and *Crataegus mexicana*, either on their own, in combination with one another, or in combination with extracts from various Bursera species.

Another embodiment of the invention is directed to extraction of simmondsin compounds from Jojoba (*Simmondsia chinensis*) and use of these compounds as a human weight loss agent.

Another embodiment of the invention is directed to formula and compositions comprising a combination of extracted phytochemicals from Turnera species and Pfaffia species, with or without muira puama (a crude drug derived from various species including *Ptychopetalum olacoides*, *Liriosma ovata*, and *Chaunochiton kappleri*) for use as a health tonic and to support sexual function.

Another embodiment of the invention is directed to formula and compositions comprising a combination of extracted phytochemicals from, for example, *Heimia salicifolia*, for use as a Non-steroidal Anti-inflammatory Drug (NSAID).

Other embodiments and advantages of the invention are set forth in part in the description which follows, and in part, will be obvious from this description, or may be learned from the practice of the invention.

DESCRIPTION OF THE INVENTION

Figure 1:
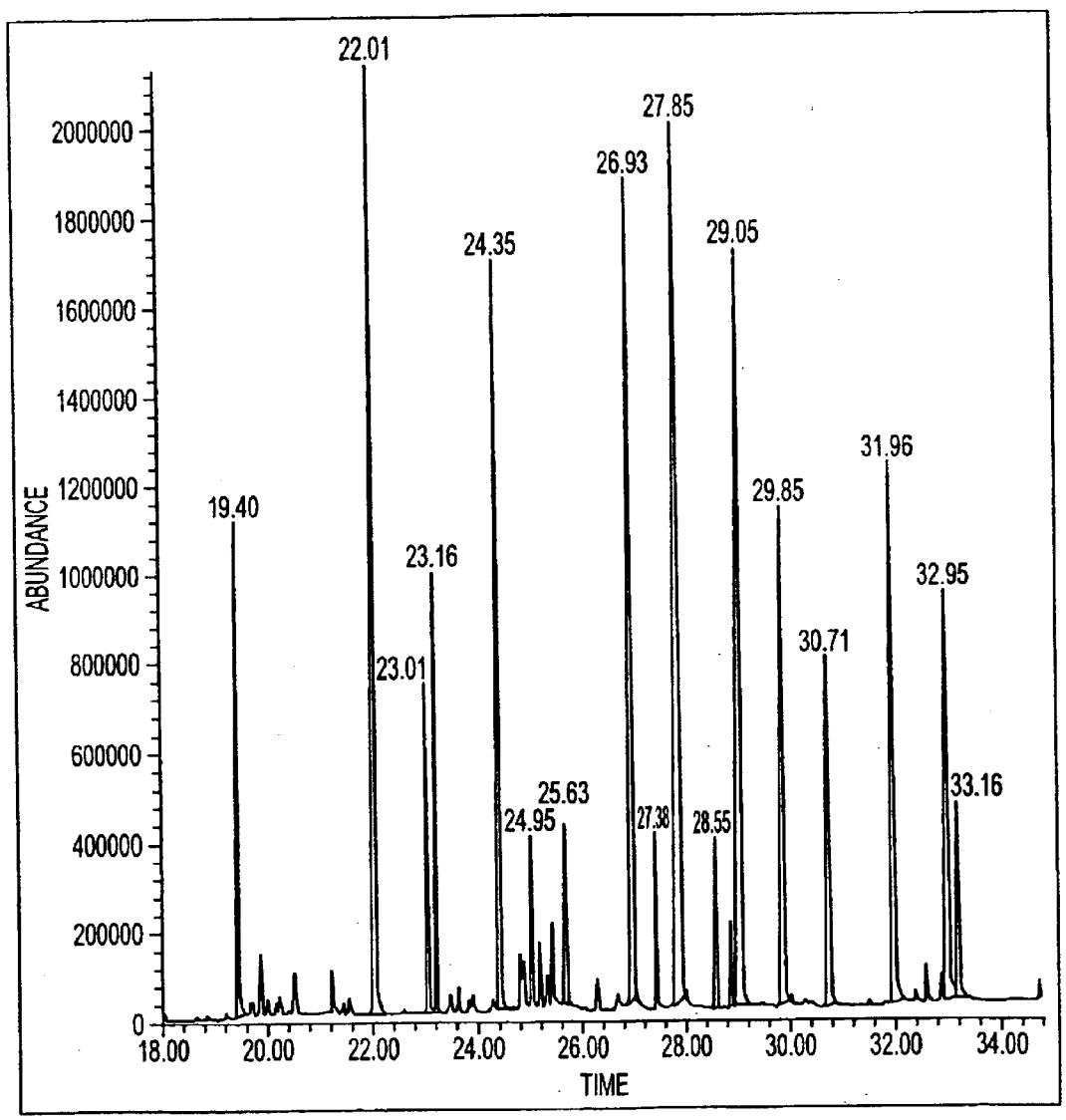
FIG. 1 Gas Chromatograph/Mass Spectroscopy (GC/MS) separation of kavalactones extracted using SFE.
Figure 2:
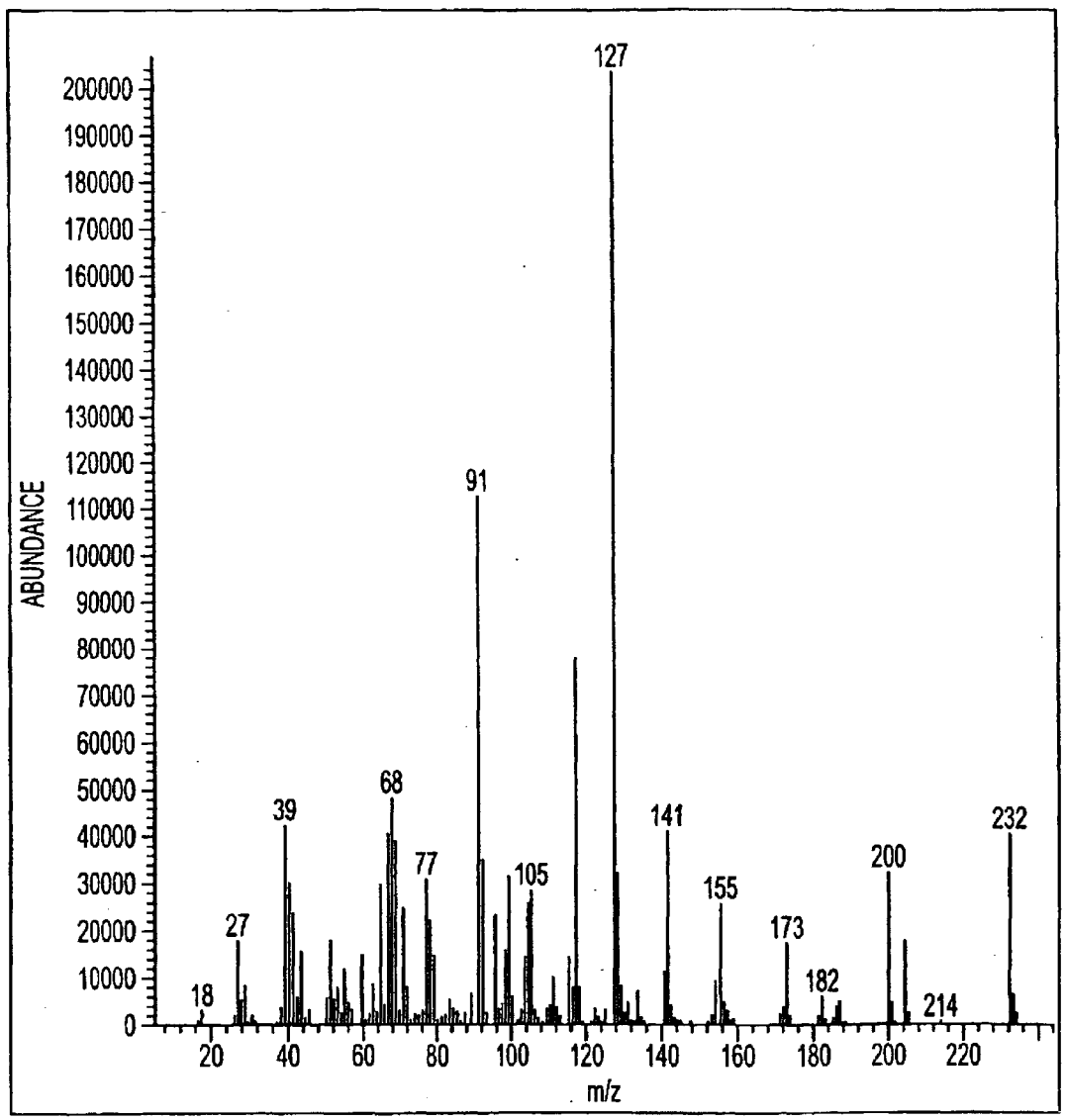
FIGS. 2–8 Mass spectra of each kavalactone listed in Table 2.
Figure 3A:
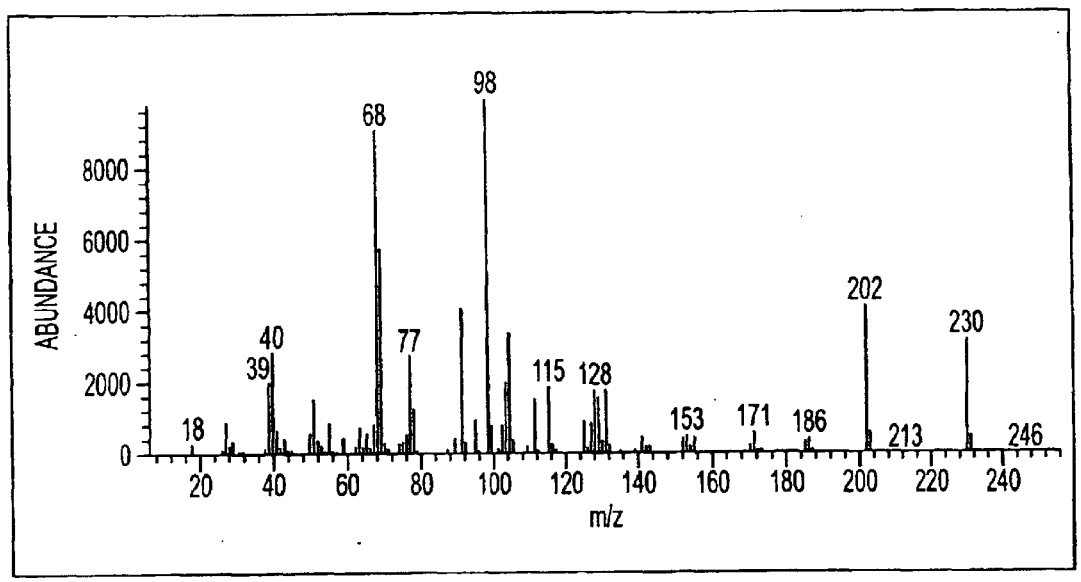
Figure 3B:
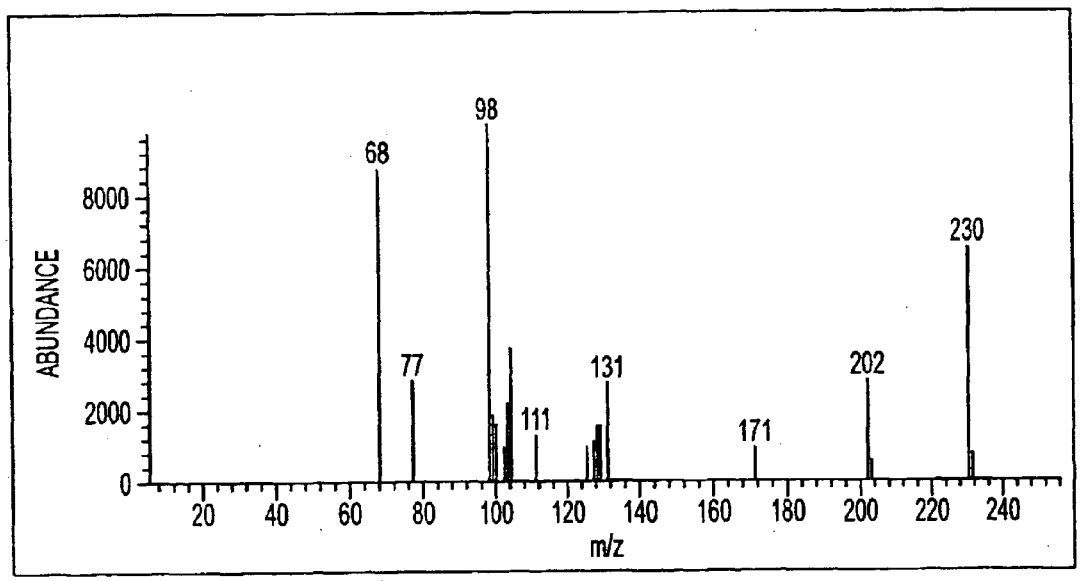
Figure 4:
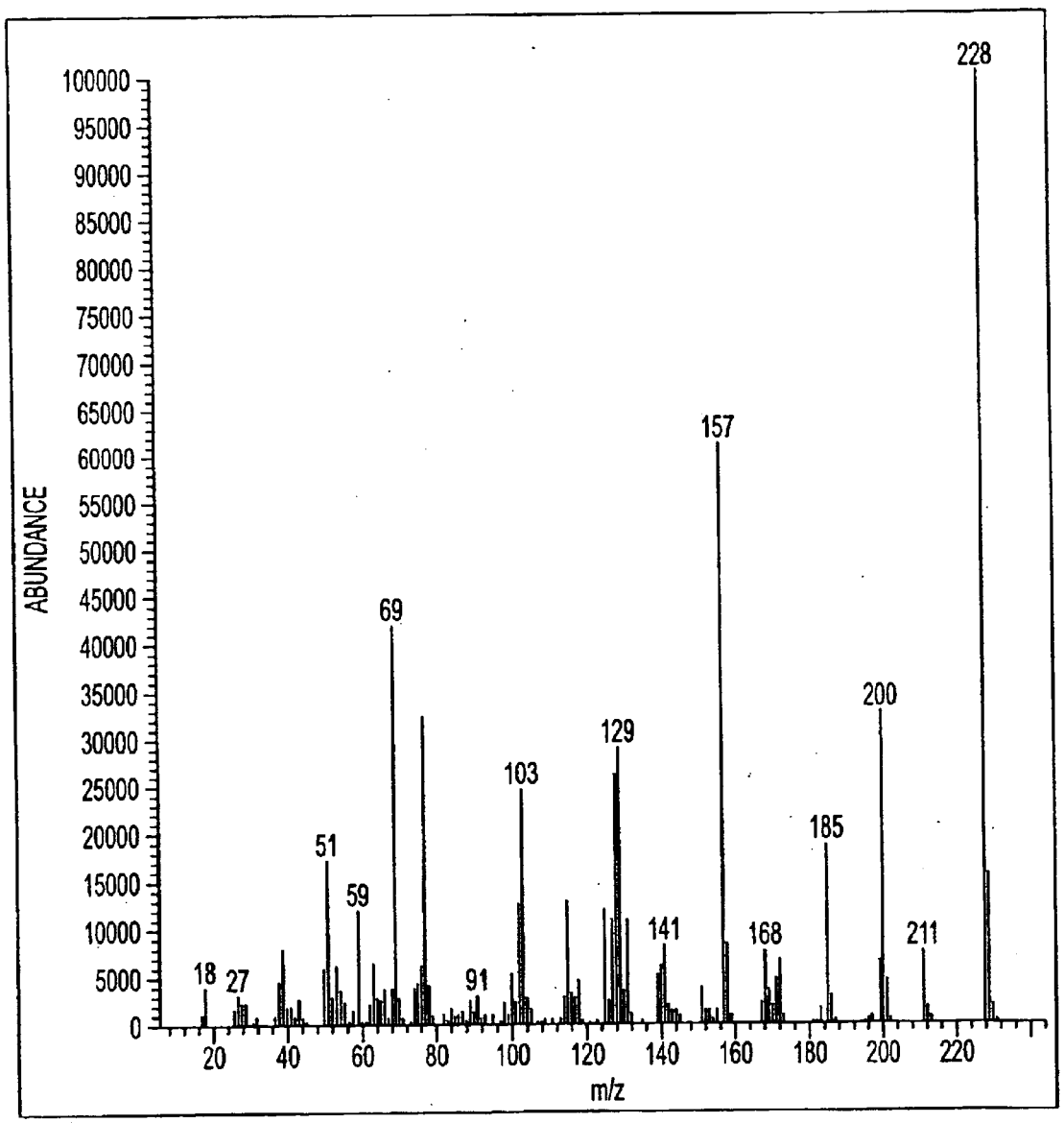
Figure 5:
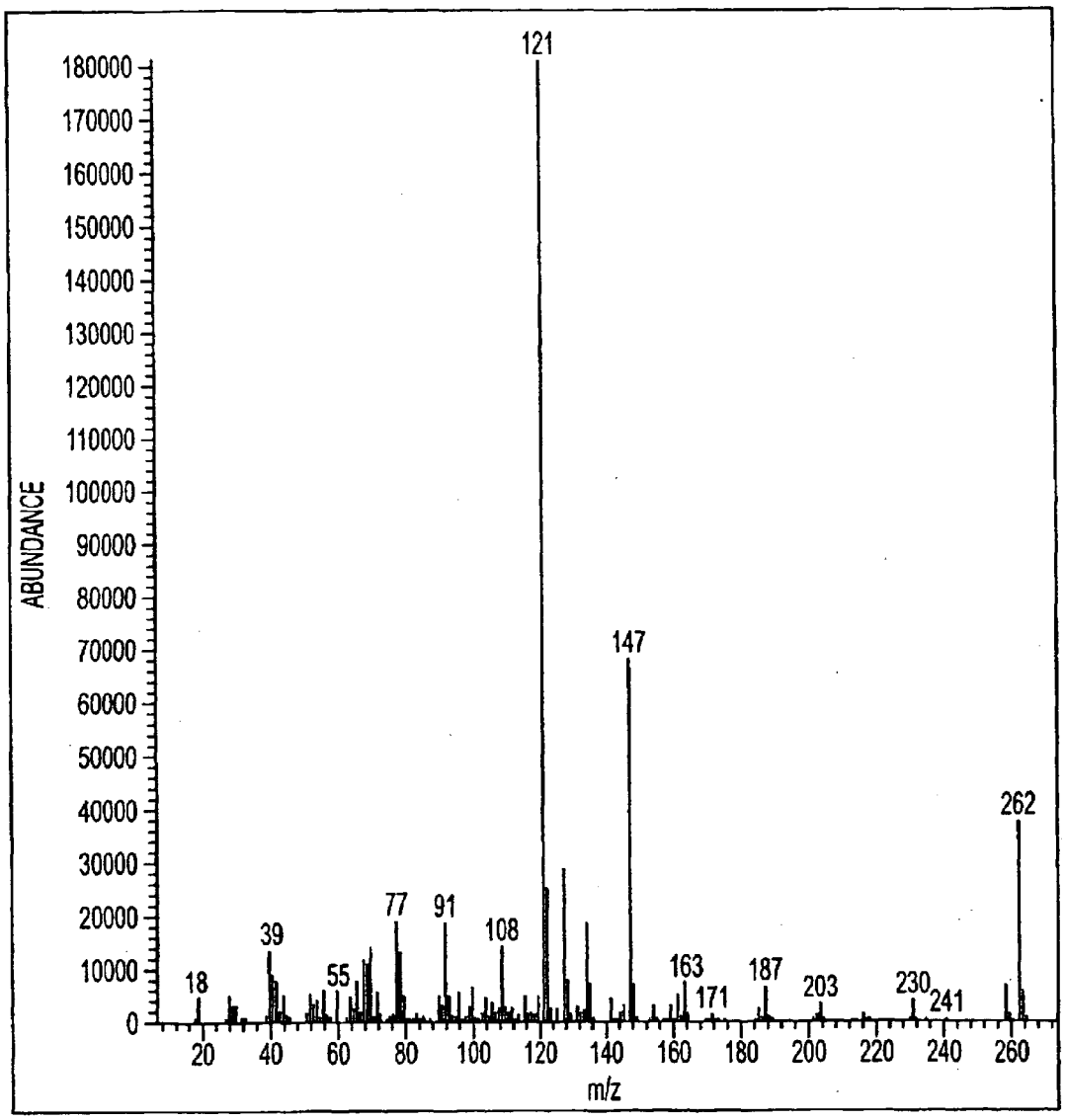
Figure 6:
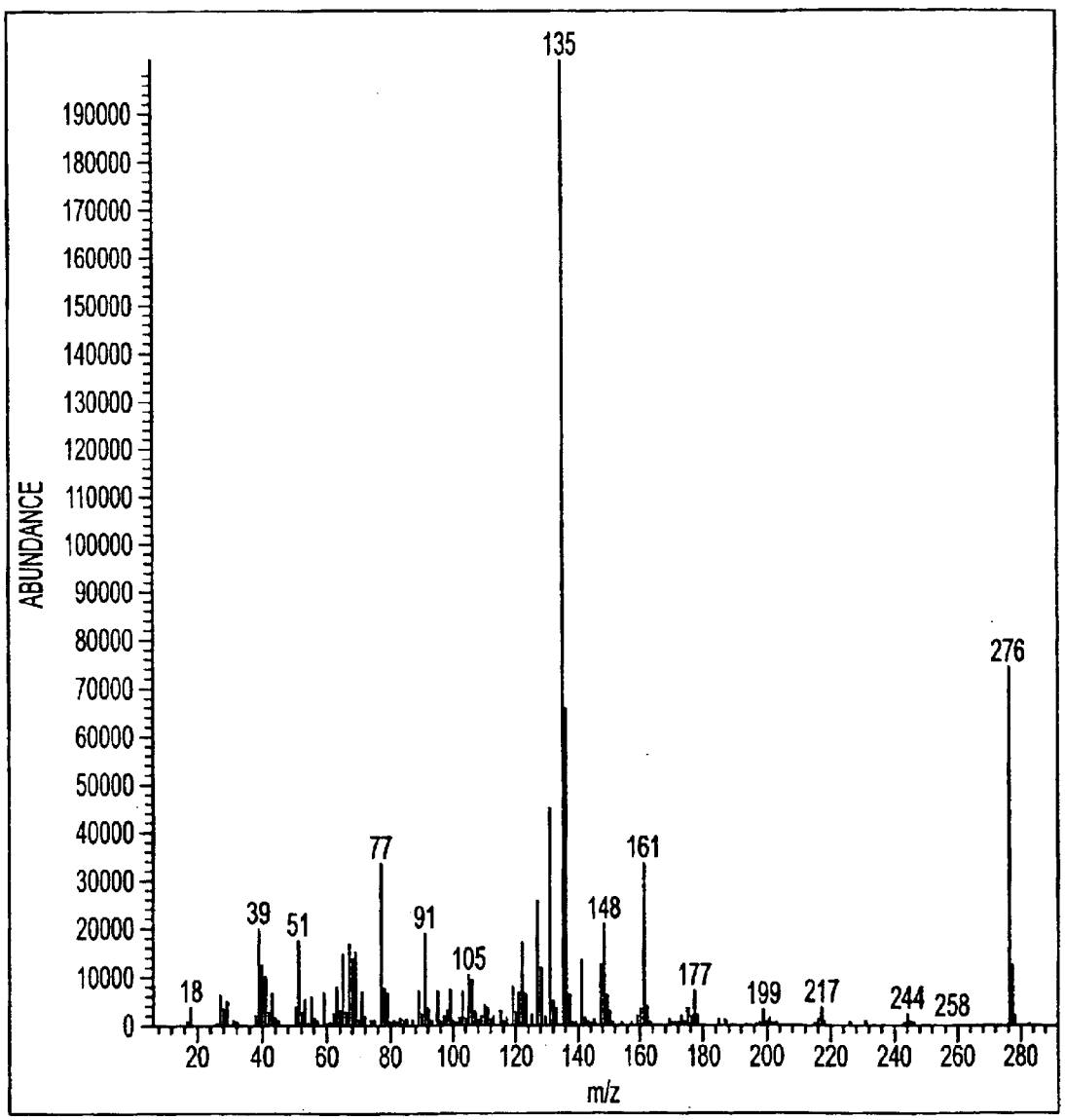
Figure 7:
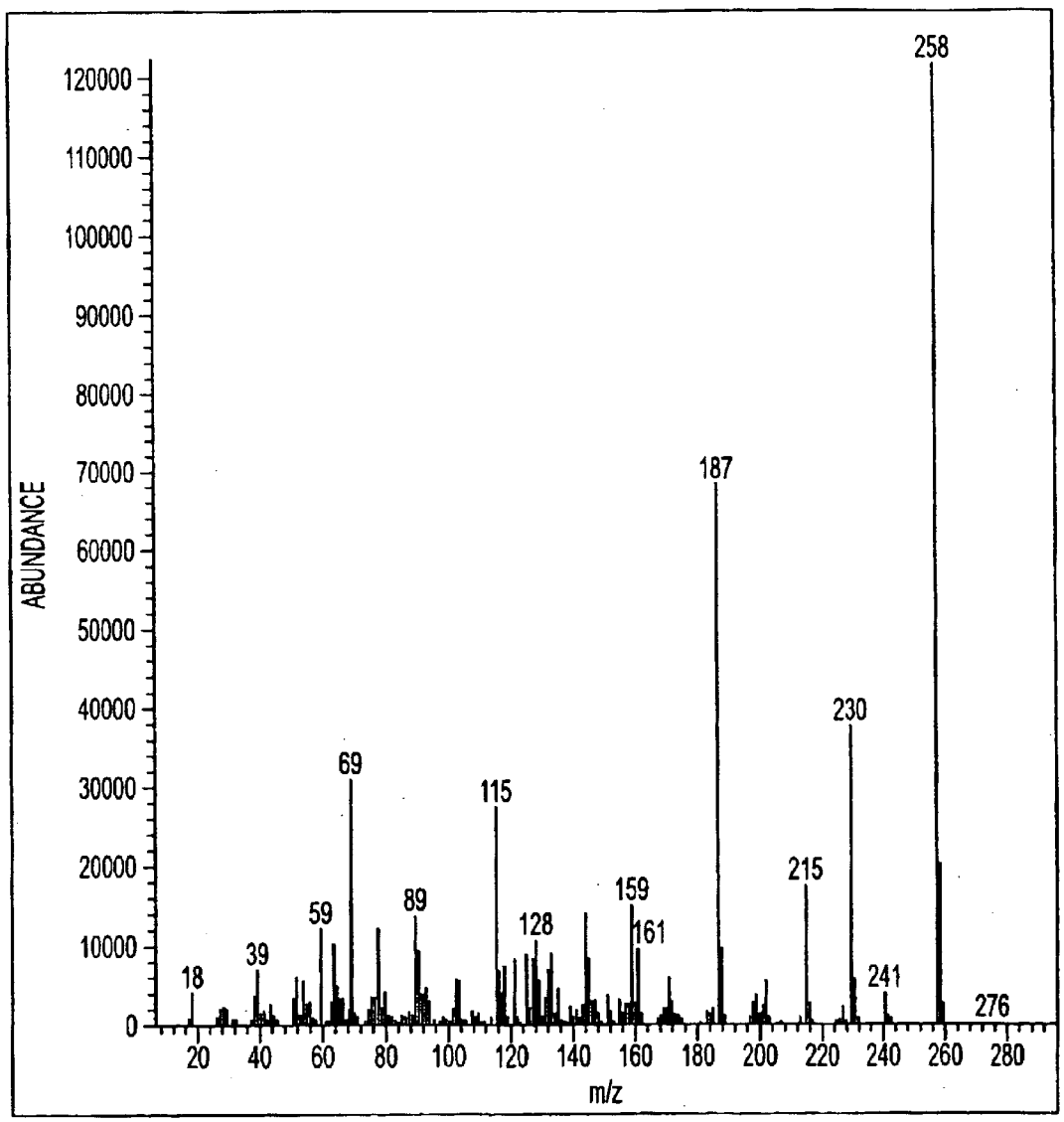
Figure 8:
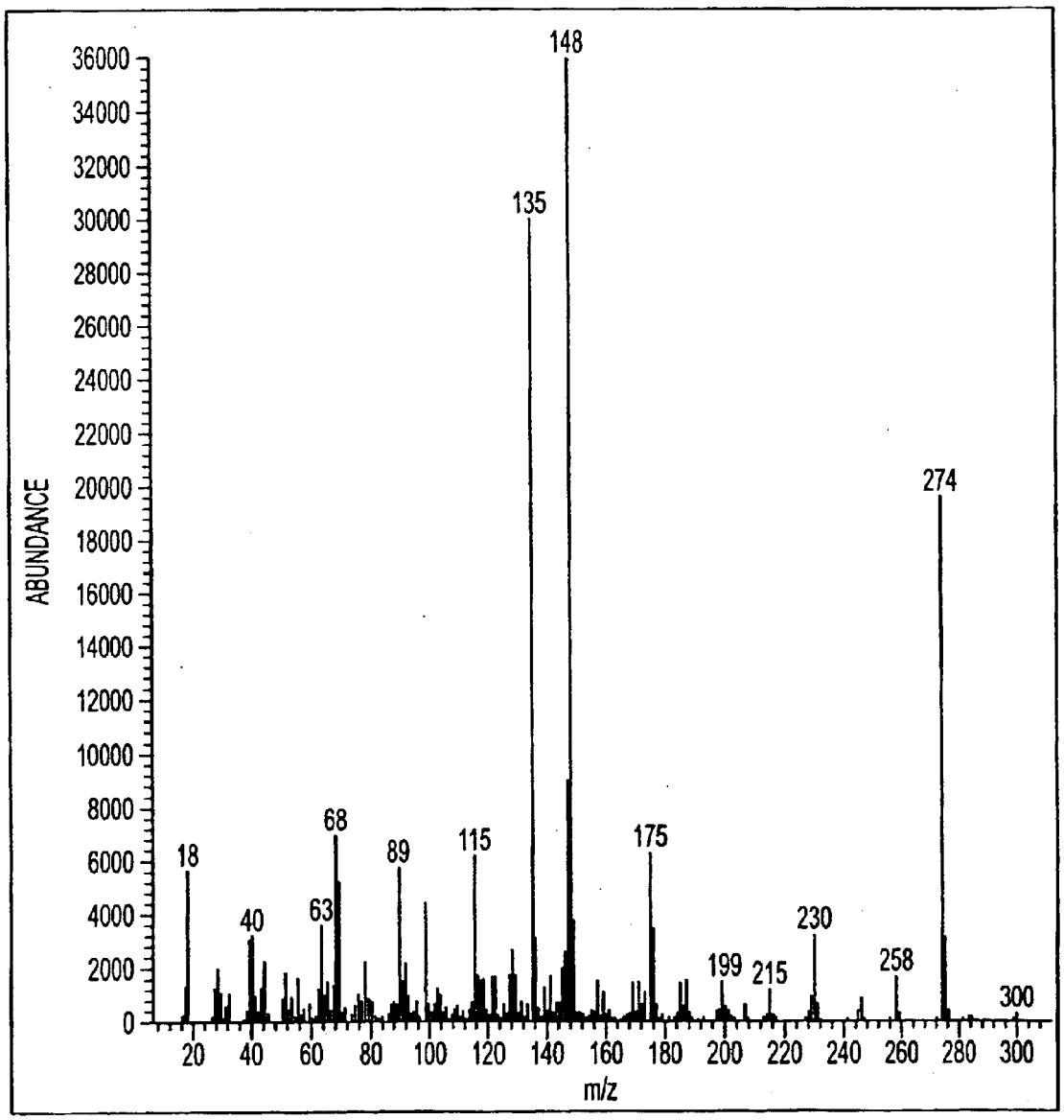
Figure 9:
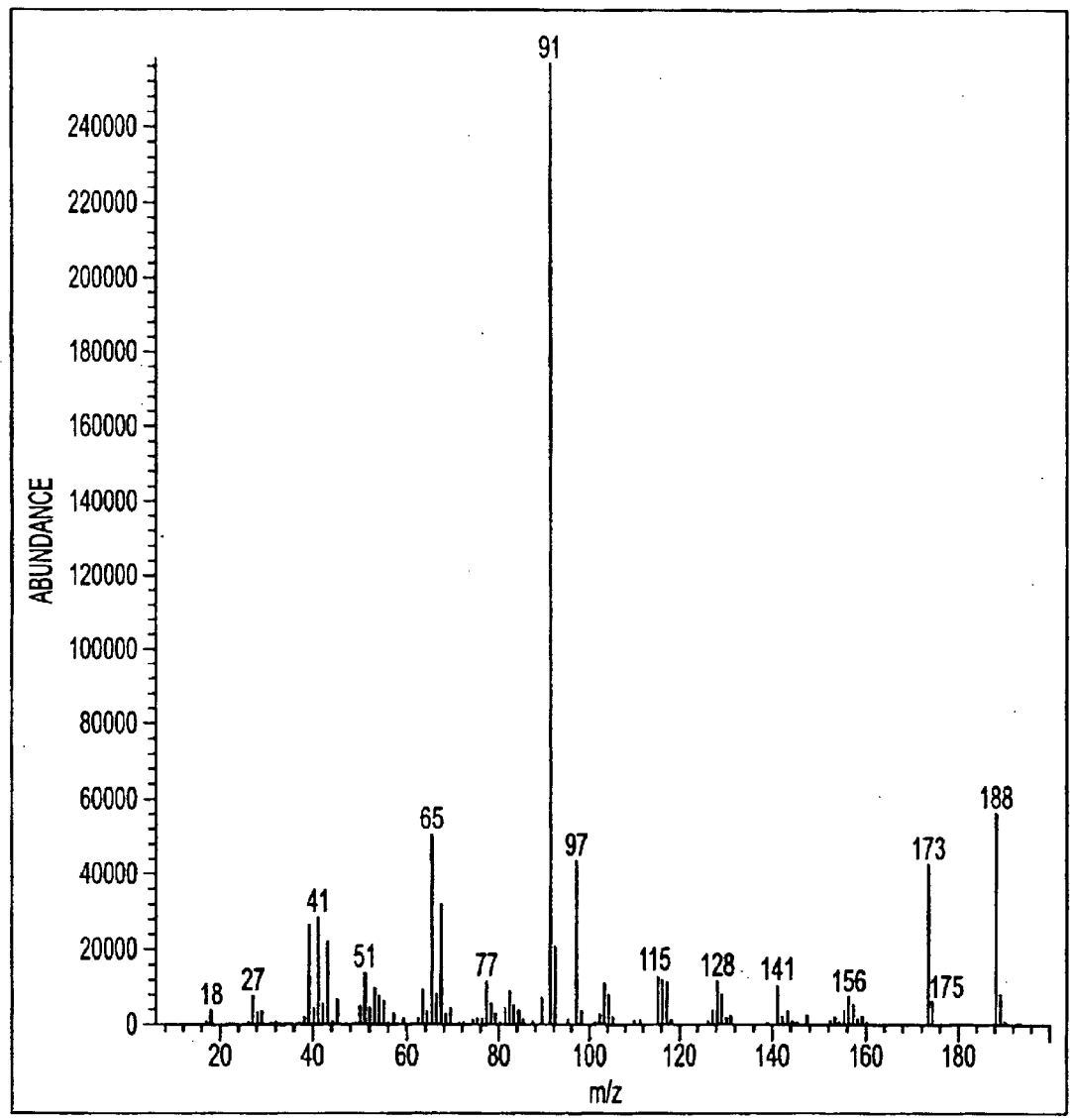
FIGS. 9–13 Spectra of other major peaks which eluted before kavalactones (tR=19.40, 22.1, 23.01, 24.35, and 26.93 min).
Figure 10:
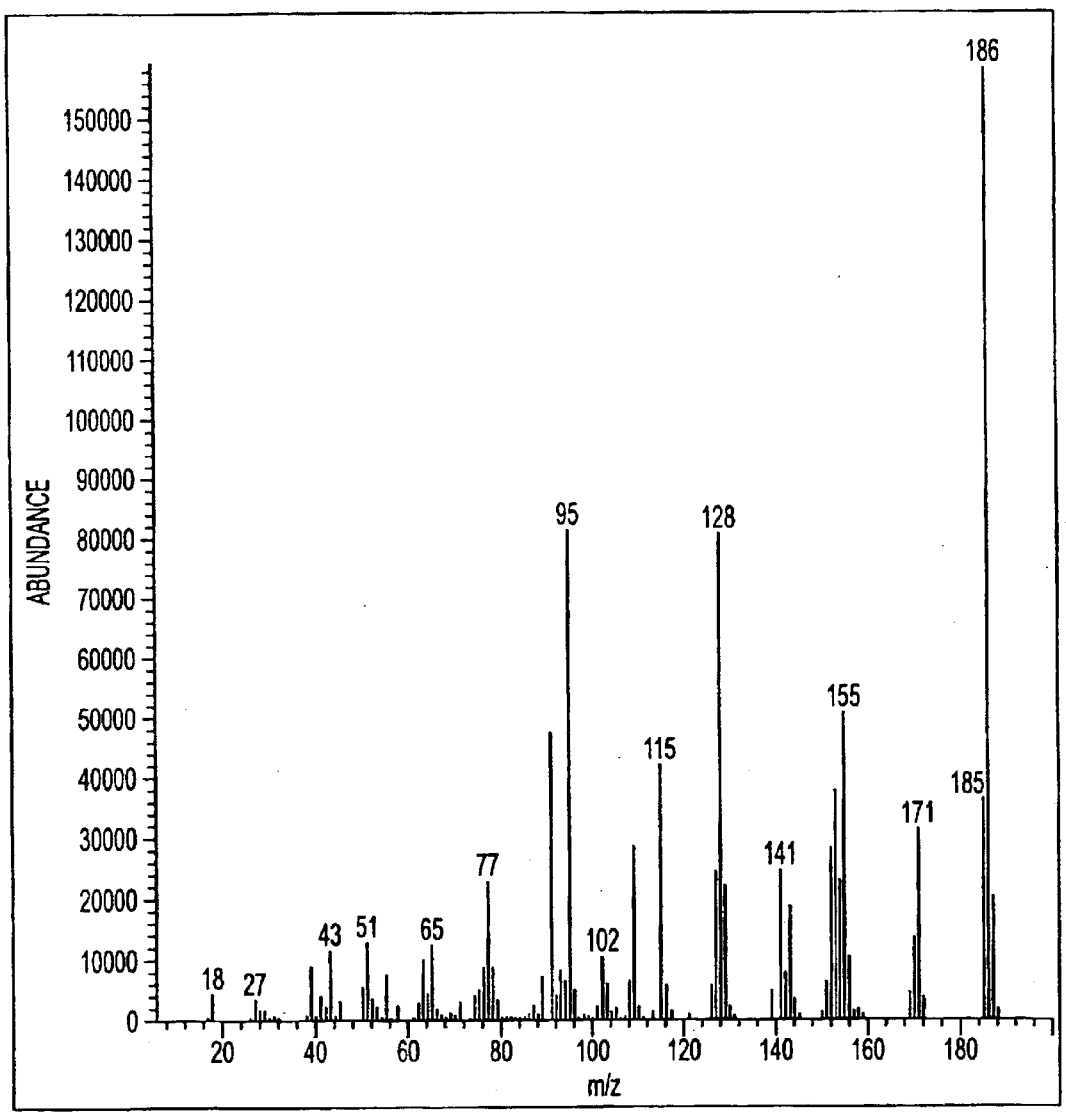
Figure 11:
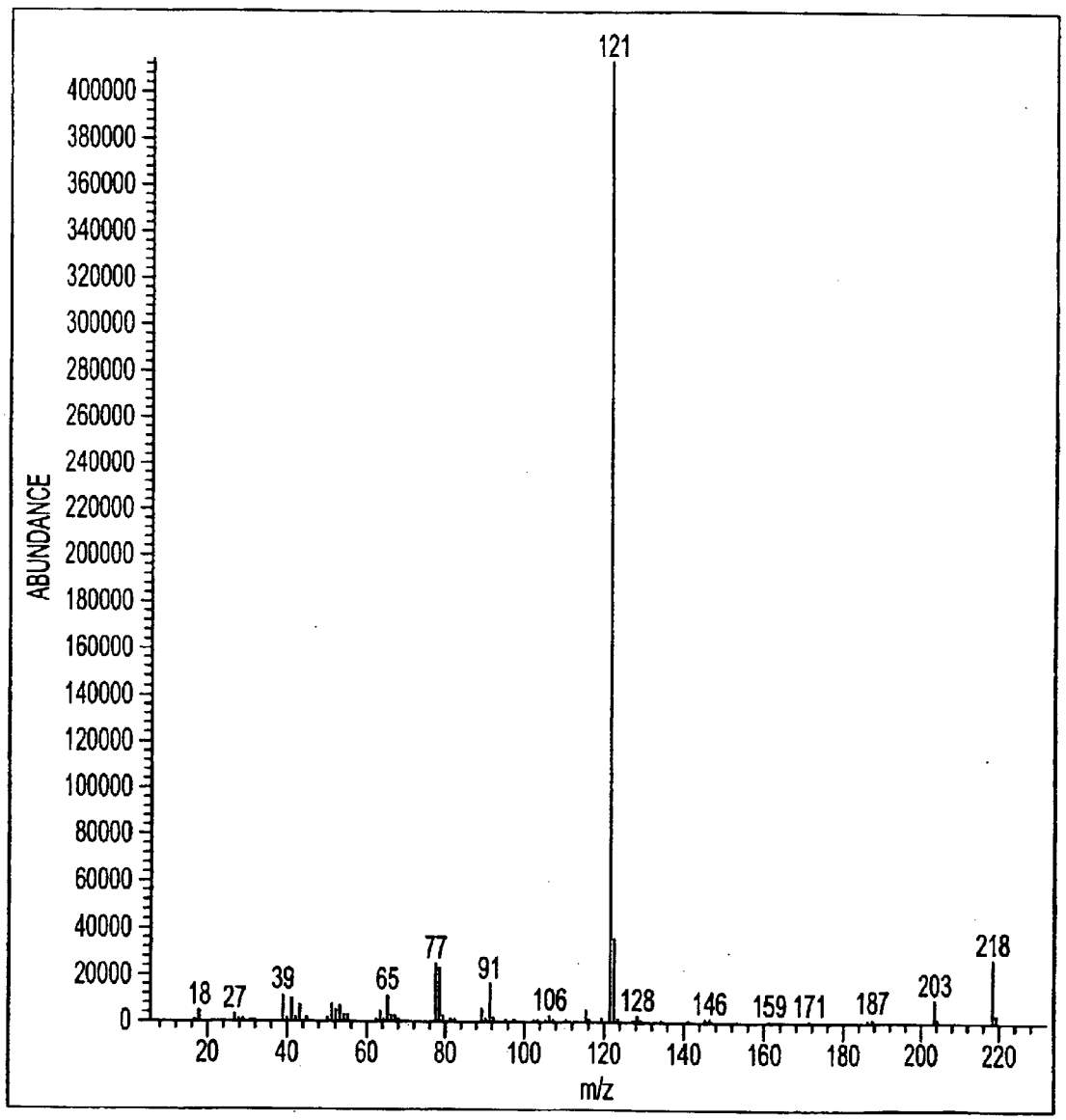
Figure 12:
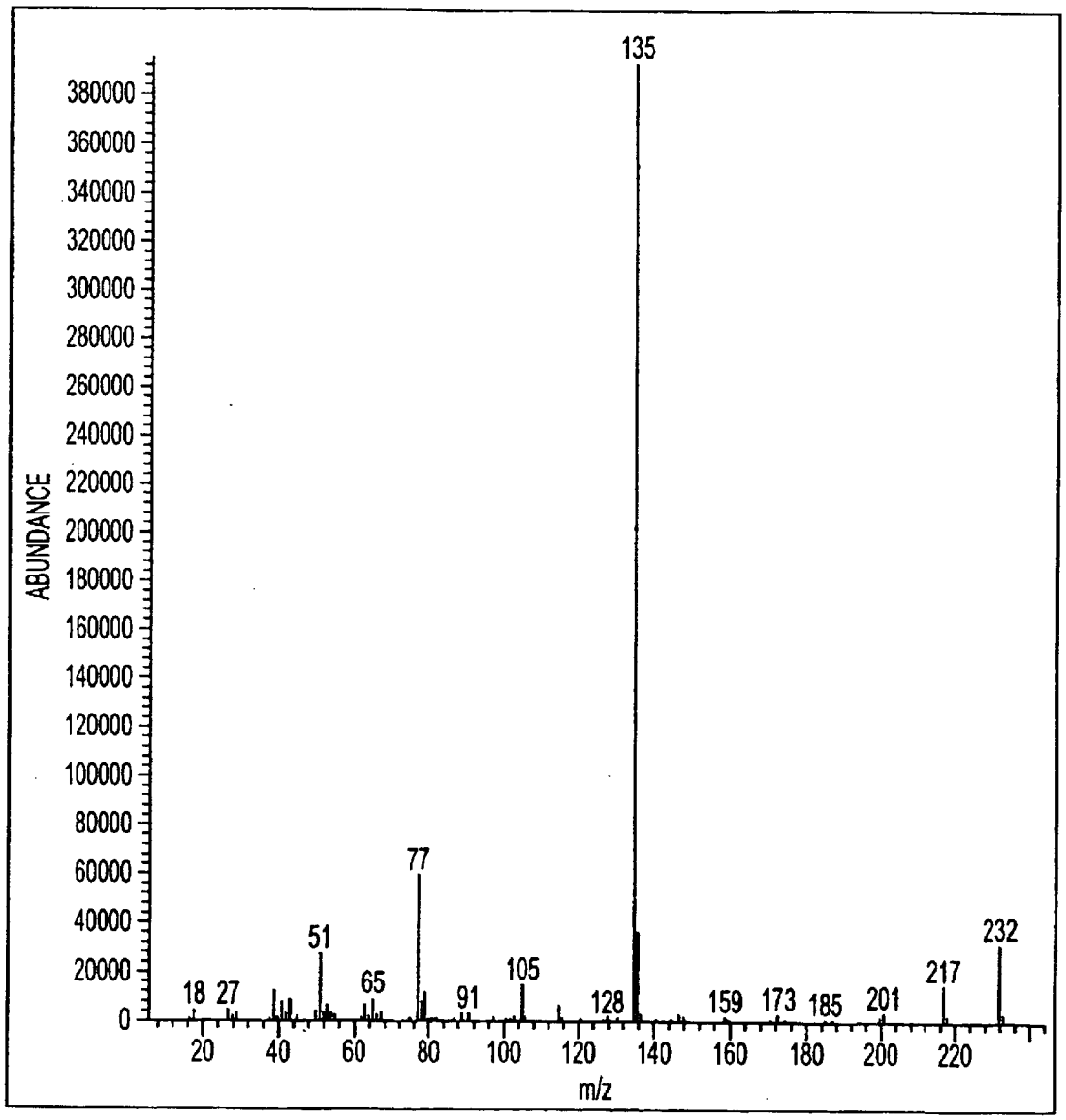
Figure 13:
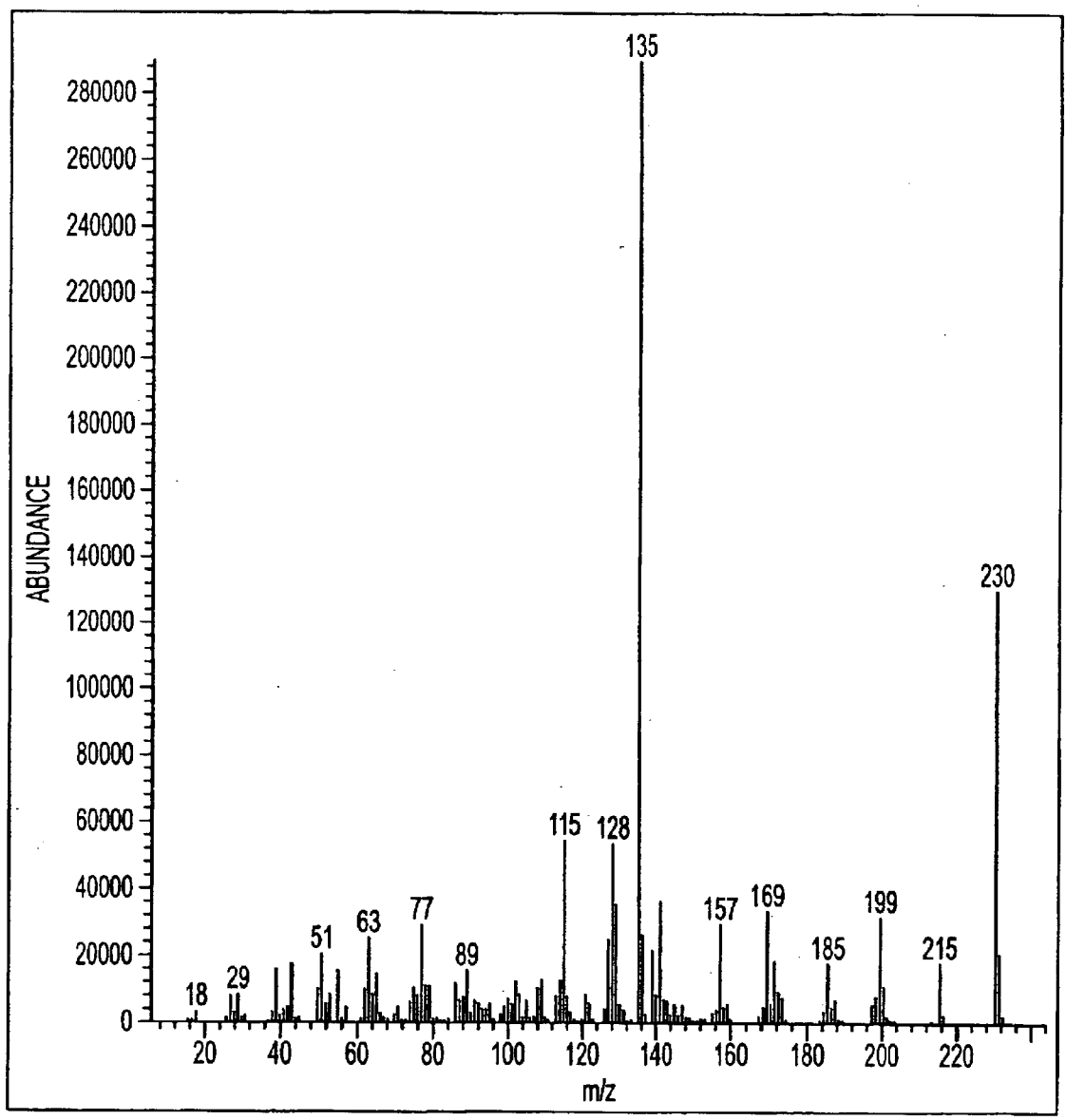

As embodied and broadly described herein, the present invention is directed to methods for isolating and purifying bioactive substances from various natural sources. The invention is further directed to pharmaceutical preparations and dietary supplements which may be prepared with the bioactive substances and use of such pharmaceutical preparations and dietary supplements to treat various human ailments.

1. Supercritical Fluid Extraction

When great amounts of pressure are exerted onto a gas, the gas changes state to become a liquid. Above a certain pressure (the critical pressure) and temperature (the critical temperature), however, a gas may be pressurized further without liquifying. This combination of pressure and temperature is known as the critical point, and above it the gas becomes a supercritical fluid. A gas in the supercritical fluid state exhibits the diffusivity of a gas but has the solvating power of a liquid. The supercritical fluid may be pressurized to achieve densities close to 1.0 kg/l, similar to many liquids. A further property of supercritical fluids is that for a given solute, solvating power is a complex function of fluid density. Consequently, supercritical fluids are often used to selectively extract or separate specific compounds from a mixture by varying fluid density through changes in pressure and temperature.

Carbon dioxide is a commonly used volatile substance for supercritical fluid extractions. At temperatures of 39° C. and above (its critical temperature) and at pressures between 200 and 600 bar, $CO_2$ is capable of removing caffeine from coffee and tea, some fragrances and flavor oils from certain plants and spices (U.S. Pat. Nos. 5,512,285 and 5,120,558), and some pharmacological active principles from certain plants and herbs. Depending on the temperature and pressure used, whether the temperature and pressure are varied during extraction, and the extraction method, different substances can be selectively removed or isolated from a plant species using supercritical fluid extraction.

In one embodiment of the present invention, $CO_2$ supercritical fluid extraction is used to extract bioactive substances from various natural sources including, but not limited to *Piper methysticum*, Byrsonima species, *Aesculus californica, Crataegus mexicana, Simmondsia chinensis*, Pfaffia species, Bursera species, Turnera species, and *Heimia salicifolia*, Psidium species, Enterlobium species, *Ptychopetalum olacoides, Liriosma ovata*, and *Chaunochiton kappleri*.

Supercritical fluid extraction can be applied to a quantity of the root, leaf, bark, or any other part of a plant or herb, or combinations thereof, containing bioactive substances. Generally the specific part or parts are ground to form a powder or paste. The powder or paste may be extracted with $CO_2$ at one or more temperatures, preferably a minimum of 45° C., and at least two pressures, preferably a minimum pressure between 200 and 400 bar and a maximum pressure between 400 and 600 bar. Use of more than one pressure, and more than one temperature, during extraction permits extraction of various bioactive substances which may be soluble in the $CO_2$ at specific pressure and temperature levels.

In a further embodiment, the extraction may be performed with a mixture of $CO_2$ and at least one other volatile substance such as butane, propane, ethanol, hexane, or any other appropriate volatile substance known to those of skill in the art. The gases may be used at any optimum ratio relative to one another. In a preferred embodiment, the extraction is performed with a combination of $CO_2$ and ethanol in a ratio of 17:3.

In another embodiment, the plant or herb may be crushed, macerated, or mixed with a solvent and the solvated mixture may then be extracted with supercritical fluid $CO_2$. See for example U.S. Pat. No. 4,985,265. Under the heavy pressures of supercritical fluid extraction, the $CO_2$-cosolvent mixture remains in the liquid monophase state. This type of liquid-liquid extraction improves elution of certain analytes. A wide variety of solvents appropriate for solvating various bioactive substances in natural sources may be used including, but not limited to, alcohols, weak acids, ketones, chloro derivatives, hydrocarbons, fluorinated hydrocarbons, acetates, ethers, or combinations thereof.

The extraction of the present invention is carried out for a minimum of 5 minutes, preferably at least 30 minutes and more preferably 60 minutes, during which extracted analytes are collected in a collection receptacle, preferably a solid phase trap packed with C18. After completion of extraction, the trap may be rinsed with a solvent appropriate for solvating the bioactive substances that have been extracted, such as, for example, 50/50 ethanol/methylene chloride for kavalactones, to collect most of the analytes in the trap. Similar methods of the present invention are outlined in Example 1 and. Example 2 below wherein seven different kavalactones were extracted from a Kava root. The methods of the present invention can be used to extract bioactive substances from one natural source at a time, or from multiple natural sources in one extraction.

A supercritical fluid extraction of the present invention can be performed as a batch extraction, as a continuous cascading extraction, as a countercurrent solvent extraction, or a combination thereof. The majority of supercritical fluid extractions in the field of natural products has involved configurations of equipment which are batch loaded systems. In these systems, extraction vessels are loaded with raw material, sealed, and the pressure and temperature increased to the desired supercritical processing range. After extraction is completed, the pressure and temperature are decreased, the vessel opened, and the spent natural source removed before the process can be repeated. To date, this process has not proven to be economically viable except in instances where it is performed at sufficiently large scale (e.g. the decaffeination of coffee) or the target compound is of sufficiently high value. In a continuous cascading extraction, multiple extraction vessels are sequentially entered on-line in a continuous manner, with the supercritical fluid passing from vessel to vessel, collecting specific targeted compounds in each vessel. See U.S. Pat. No. 5,120,558; see also Stahle, et al., Dense Gases for Extraction and Refining, Springer-Verlag, Berlin, 1988. This method is advantageous in that the average loading rate of the $CO_2$ is increased because the $CO_2$ fluid carrying low quantities of analyte from partially extracted vessels can dissolve more analyte from the new vessel sequentially introduced, thus effectively increasing the average loading rate of the $CO_2$ fluid, and hence, the analyte extraction rate per hour. In a countercurrent extraction process of the present invention, bioactive substances from plants and herbs are extracted and concentrated in a series of countercurrent mechanical presses. See U.S. Pat. No. 6,013,304. The presses may be kept at high pressure and escalated temperature as outlined above to facilitate the supercritical fluid extraction. As the supercritical fluid becomes more highly concentrated in its analyte content through sequential pressing, the analyte containing fluid is recirculated to the first press to extract more analyte and become more concentrated.

2. Dense Gas Extraction

Due to it's non-flammable nature, as opposed to propane or butane, and excellent solvating properties for a wide range of target analytes, $CO_2$ has become the most common volatile substance used in the art of supercritical fluid extraction. However, $CO_2$ is effective as an extraction medium only at extreme pressures. This results in a high cost of equipment to perform the extraction and to inherent dangers associated with extreme pressure vessels. Furthermore, the cost of scaling up such equipment is prohibitive so the equipment tends to remain small scale. Additionally, supercritical $CO_2$ extraction systems operate at temperatures in excess of 39° C. Holding labile natural materials at such temperatures for long periods during processing may result in thermally or enzymatically induced spoilage.

Recently, non-chlorinated fluorocarbon solvents have been disclosed for extracting fragrances and flavors from natural materials. See U.S. Pat. No. 5,512,285. In one embodiment of the present invention, non-chlorinated fluorocarbon solvents including, but not limited to, trifluoromethane, difluoromethane, fluoromethane, pentafluoroethane, 1,1,1,-trifluoroethane, 1,1-difluoroethane, 1,1,1,2,2,3,3-heptafluoropropane, 1,1,1,3,3,3-hexafluoropropane, 1,1,1,2,2-pentafluoropropane, 1,1,1,2,2,3-hexafluoropropane, 1,1,2,2,3,3-hexafluoropropane, 1,1,1,2,3,3,-hexafluoropropane, and 1,1,1,2-tetrafluoroethane may be used. The solvent used in the present invention may be a mixture of these solvents to tailor the boiling point of the mixture to a particular process and facilitate the selective elution of specific bioactive substances. The solvent may be further modified by mixing with another volatile substance such as butane, hexane, ethanol or any other appropriate substance. In a preferred embodiment, the non-fluorocarbon solvent used for extraction is a tetrafluoroethane, preferably 1,1,1,2-tetrafluoroethane. In a further preferred embodiment, the tetrafluoroethane is unmodified.

In a process of the present invention, ground or crushed natural sources such as plants and/or herbs are contacted with a non-chlorinated fluorocarbon solvent in the liquid phase so as to charge the solvent with analyte. Charged solvent is collected and removed to isolate the analyte. In one embodiment of the present invention, the herb or plant material is contacted with a non-chlorinated fluorocarbon solvent in an extraction vessel after the vessel has been sealed and air has been removed. The resulting mixture of the solvent and natural source is maintained under pressure so that the natural source and solvent are in intimate contact to charge the solvent with analyte. This type of extraction may be carried out in any extractor which may be sealed and evacuated of air as required. The extractor may be made of stainless steel, heavy walled glass, or any other non-reactive material which is able to withstand elevated or reduced pressures. The extraction may be performed at any suitable temperature and is preferably carried out at or below room temperature.

In another embodiment, the extraction may be carried out as a supercritical fluid extraction at increased pressures and varied temperatures. Particularly if the fluorinated hydrocarbon solvent is modified with another volatile substance with a higher boiling point, increased pressures and temperatures may be used to properly elute desired analytes.

In another embodiment, the plant or herb may be crushed, macerated, or mixed with a solvent and the solvated mixture may then be extracted with fluoronated hydrocarbon solvents or modified fluoronated hydrocarbon solvents. This type of liquid-liquid extraction may improve elution of certain analytes. A wide variety of solvents appropriate for solvating various bioactive substances in natural sources may be used including, but not limited to, alcohols, weak acids, ketones, chloro derivatives, hydrocarbons, fluorinated hydrocarbons, acetates, ethers, or a combination thereof Extraction may be carried out batch-wise, as a continuous-cascading extraction, or as a countercurrent-solvent extraction. In a preferred embodiment of the present invention, bioactive substances are extracted from plants and/or herbs using fluorocarbon solvents in a continuous cascading extraction. The extractor may communicate with an evaporator. During evaporation of the solvent from the eluted analyte, the solvent may be allowed to pass intermittently from the reactor to the evaporator to maintain a level of liquid and a gas-filled head space in the evaporator. Evaporation of the solvent may be achieved by withdrawal of gaseous solvent from the head space of the evaporator. The withdrawn gaseous solvent may be transferred to a compressor or some similar device to reliquify the solvent, thereby economically reusing the solvent.

In another embodiment, the evaporator may have one or more sources of heat to control the temperature of the evaporator during evaporation of the solvent. In a further embodiment, the heat source may be thermostatically controlled to provide constant evaporation temperature. The non-chlorinated fluorinated hydrocarbon solvents generally boil off before the desired analytes and it is therefore not necessary to elevate the temperature of distillation of the solution during the solvent recovery phase of the process. Extracts produced in this manner contain very low levels of solvent residues.

The vapor pressure of most fluorocarbon solvents is greater than atmospheric pressure at room temperature. For example, the vapor pressure of 1,1,1,2-tetrafluoroethane is 5.6 bar at 20° C. In a preferred embodiment, extraction is thus carried out at a pressure from 0–10 bar and preferably 3.5–6.0 bar. Although most of these solvents must be handled in equipment which is capable of tolerating such pressures, this equipment is a fraction of the cost of equivalent equipment required for handling supercritical $CO_2$, and a fraction of the degree of sophistication or hazard inherent in a manufacturing plant for handling liquefied hydrocarbon gases under pressure.

3. Supercritical Fluid Chromatography

Once bioactive substances are collected as extracts from plants and herbs following any extraction method, the substances in the extracts can be separated and isolated using various techniques such as gas chromatography (GC) or high pressure liquid chromatography (HPLC). Gas chromatography, however, is not scalable to provide a method for isolation of each substituent in large quantity. Liquid chromatography, on the other hand, has the drawback of utilizing large volumes of solvent.

In one embodiment of the present invention, packed column supercritical fluid chromatography is used to separate the bioactive substances in extracts obtained from various natural sources. Bioactive substances that can be separated from such sources include terpenes, terpenoids, flavones and flavonoids, steroids, sterols, saponins and sapogenins, alkanes, alkaloids, amines, amino acids, aldehydes, alcohols, fatty acids, lipids, lignans, phenols, pyrones, butenolides, lactones, chalcones, ketones, benzenes, cyclohexanes, glucosides, glycosides, cyanidins, furans, phorbols, quinones and phloroglucinols. The invention can also be applied to the recovery of bioactive substances that are large molecular weight materials such as proteins, peptides, enzymes, polysaccharides and carbohydrates. Sources from which bioactive substances can be isolated include, but are not limited to various plant species of Kava (such as Kava root), Byrsonima, Aesculus (e.g. *A. californica*), *Crataegus mexicana*, Jojoba, Pfaffia, Alternanthera (e.g. *A. repens*), Bursera, Turnera, Perezia, Heimia (e.g. *H. salicifolia*), Psidium, Enterlobium, Ptychopetalum (e.g. *P. olacoides*), Liriosma (e.g. *L. ovata*) and Chaunochiton (e.g. *C. kappleri*). Plants from which extracts can be prepared and natural substances isolated according to the invention include the higher plants: Acanthopanax, Acanthopsis, Acanthosicyos, Acanthus, Achyranthes, Acokanthera, Aconitum, Acorus, Acronychia, Actaea, Actinidia, Adenia, Adhatoda, Aegle, Aesculus, Aframomum, Agastache, Agathosma, Alchemilla, Aleurites, Allium, Aloe, Alonsoa, Aloysia, Alphitonia, Alpinia, Alternanthera, Amaranthus, Amomum, Amphipterygium, Amyris, Anchusa, Ancistrocladus, Anemopsis, Angelica, Annona, Anonidium, Anthemis, Antidesma, Apium, Aralia, Aristolochia, Artemisia, Artocarpus, Asarum, Asclepias, Asimina, Aspalanthus, Asparagus, Aspidosperma, Astragalus, Astronium, Atropa, Avena, Azadirachta, Azara, Baccharis, Bacopa, Balanites, Bambusa, Barleria, Barosma, Bauhinia, Belamcanda, Benincasa, Berberis, Berchemia, Bixa, Bocconia, Borago, Boronia, Boswellia, Brosimum, Brucea, Brunfelsia, Bryonia, Buddleja, Bulnesia, Bupleurum, Bursera, Byrsonima, Calamintha, Calea, Calophyllum, Camellia, Camptotheca, Cananga, Canarium, Canella, Capparis, Capsicum, Carthamus, Carum, Cassia, Cassine, Castanospermum, Catalpa, Catha, Catharanthus, Cayaponia, Cecropia, Centaurea, Centipeda, Centranthus, Cephaelis, Chiranthodendron, Chondrodendron, Chrysophyllum, Cimicifuga, Cinchona, Cinnamomum, Cistus, Citrus, Clausena, Cnicus, Coccoloba, Codonopsis, Coffea, Coix, Cola, Coleus, Colletia, Combretum, Commiphora, Cordia, Coriaria, Correa, Corydalis, Costus, Crataegus, Croton, Cryptolepis, Cudrania, Cuminum, Cuphea, Cucurma, Cyclanthera, Cymbopogon, Cynara, Cynoglossum, Cyperus, Cyrtocarpa, Dalbergia, Dalea, Danae, Daphne, Datura, Daucus, Decadon, Dendrocalamus, Dendropanax, Deppea, Derris, Desmos, Dichrostachys, Dictamnus, Digitalis, Dillenia, Dioscorea, Dioscoreophyllum, Diosma, Diospyros, Drimys, Duboisia, Duguetia, Dysoxylum, Echinacea, Eclipta, Ehretia, Ekebergia, Eleagnus, Elettaria, Eleutherococcus, Encelia, Entandrophragma, Ephedra, Epimedium, Eriobotrya, Erodium, Eryngium, Erythrochiton, Erythroxylum, Escholzia, Esenbeckia, Euclea, Eucommia, Euodia, Eupatorium, Fabiana, Ferula, Fevillea, Fittonia, Flindersia, Foeniculum, Gallesia, Galphimia, Garcinia, Gaudichaudia, Gaultheria, Gelsemium, Gentiana, Geranium, Gigantochloa, Gingko, Glochidion, Gloeospernum, Grewia, Greyia, Guaiacum, Gymnema, Haematoxylum, Hamamelis, Hamelia, Harpagophytum, Hauya, Heimia, Helleborus, Hieracium, Hierochloe, Hilleria, Hippophae, Houttuynia, Hovenia, Humulus, Huperzia, Hura, Hybanthus, Hydnocarpus, Hydnophytum, Hydrastis, Hydrocotyle, Hymenaea, Hyoscamus, Hypericum, Hyptis, Hyssopus, Iboza, Idiospermum, Ilex, Illicium, Indigofera, Inga, Inula, Iochroma, Iresine, Iris, Jacaranda, Jatropha, Juniperus, Justicia, Kadsura, Kaempferia, Lactuca, Lagochilus, Larrea, Laurus, Lavandula, Lawsonia, Leonurus, Leucas, Ligusticum, Lindera, Lippia, Liriosma, Litsea, Lobelia, Lonchocarpus, Lonicera, Lycium, Macfadyena, Maclura, Mangifera, Mansoa, Marcgravia, Marrubium, Martinella, Matricaria, Maytenus, Medicago, Melissa, Mentha, Mimosa, Mimusops, Mitragyna, Montanoa, Morkillia, Mouriri, Mucuna, Mutisia, Myrica, Myristica, Nardostachys, Nepeta, Nicotiana, Ocotea, Olea, Oncoba, Ophiopogon, Origanum, Pachyrhizus, Panax, Papaver, Pappea, Parthenium, Passiflora, Paullinia, Pelargonium, Penstemon, Perezia, Perilla, Persea, Petiveria, Petroselinum, Peucedanum, Peumus, Pfaffia, Phoebe, Phyllanthus, Phytolacca, Pilocarpus, Pimenta, Pimpinella, Pinellia, Piper, Piqueria, Pithecellobium, Pittosporum, Plectranthus, Pleuropetalum, Podophyllum, Pogostemon, Polygala, Polygonum, Polymnia, Psacalium, Psychotria, Pterygota, Ptychopetalum, Pueraria, Punica, Pycnanthemum, Pygeum, Quararibea, Quassia, Quillaja, Randia, Ratibida, Rauvolfia, Rehmannia, Renealmia, Rheum, Rollinia, Rorippa, Rosmarinus, Rudbeckia, Ruellia, Rumex, Ruscus, Ruta, Saccharum, Salix, Salvia, Sambucus, Sanguinaria, Sapium, Sassafras, Satureja, Sceletium, Schizandra, Securidaca, Securinega, Serenoa, Simmondsia, , Smilax, Stachytarpheta, Stachys, Staurogyne, Stelechocarpus, Stephania, Sterculia, Stevia, Strophanthus, Strychnos, Symphytum, Syzygium, Tabebuia, Tabernaemontana, Tabernanthe, Tanacetum, Taxus, Tecoma, Terminalia, Teucrium, Thaumatococcus, Tribulus, Trifolium, Trigonella, Triplaris, Triumfetta, Tumera, Tussilago, Tylophora, Tynnanthus, Uncaria, Urginea, Urtica, Uvaria, Vaccinium, Valeriana, Vallesia, Vangueria, Vanilla, Vellozia, Vepris, Verbascum, Verbena, Vetiveria, Virola, Viscum, Vismia, Vitex, Voacanga, Warburgia, Withania, Zanthoxylum, Zingiber, Zizyphus and Zygophyllum. In addition to the genera of higher plants listed above, compounds can be recovered from such biological sources as algae, bacteria, fungi, lichens, mosses, and marine organisms such as corals, sponges, tunicates or other invertebrate or vertebrate organisms.

A variety of stationary phases, pressures, temperatures, and modifier concentrations can be applied to optimize the separation. Separations of extracted kavalactones are used to illustrate some methods of packed column supercritical fluid chromatography separation of the present invention in Examples 3 to 10 below. This invention is significant given the amenability of SFC for both semi-preparative and preparative scale fractionations which could ultimately afford isolation of each substituent in an analyte mixture in milligram quantities. Furthermore, according to the present invention, equipment for the separation of analytes can be built to -communicate with extraction and evaporation equipment to allow a continuous assembly line process for extracting, separating, and isolating specific bioactive substances from selected plants and herbs.

4. Therapeutic Plant Extracts and Their Uses i) Extracts of Byrsonima

In one embodiment of the present invention, extracts of Byrsonima species, such as *Byrsonima crassifolia*, comprising a variety of triterpenes, amino acids, and/or flavonoids are prepared. These extracts may be prepared using water, non-aqueous solvents such as methanol, ethanol, or ethyl acetate, a mix of water with a non-aqueous solvent, or using one of the extraction methods described above. The extracts of Byrsonima may be administered to humans in therapeutic quantities to treat a variety of ailments including, but not limited to, gastrointestinal disorders (e.g. diarrhea, Chron's disease, irritable bowel syndrom), and neurological and vascular disorders such as stroke, Parkinson's disease, and Alzheimer's disease.

The extracts of Byrsonima may further be combined with extracts from other plant species including, but not limited to, Psidium species such as *Psidium Guajava*, and Enterolobium species such as *Enterolobium cyclocarpum*. The extracts of these other species may be prepared by any method known in the art or any of the methods described above.

In a further embodiment of the invention, the extracts of the Byrsonima species and/or any other extracts to be combined with the Byrsonima extract, may be separated to isolate specific bioactive substances to treat specific ailments. For example, pipecolic acid may be isolated from the extracts of the leaves and bark of *Byrsonima crassifolia*. The separation may be performed using any separation technique known to those of skill in the art, or a packed column supercritical fluid chromatography separation method as described herein. Once separated, the pipecolic acid may be administered by itself, or in combination with other bioactive substances from Byrsonima or other plant extracts, in therapeutic quantities to treat neurological and vascular disorders.

In still a further embodiment, extracts of the Byrsonima species alone or in combination with extracts from other plant or herb species, or isolated bioactive substances of the Byrsonima species alone or in combination with bioactive substance of other plants or herbs, may be made into a capsule, pill, pastille, or elixir, in combination with other inert or pharmacological ingredients to be administered to patients.

ii) Extracts of North American Varieties of Aesculus and Crataegus Species

In one embodiment of the present invention, extracts of Aesculus species, such as *Aesculus californica* comprising aescin and a variety of triterpene glycosides, and Crataegus species, such as *Crataegus mexicana* comprising a variety of flavonoids and oligomeric procyanidins are prepared. These extracts may be prepared using water, non-aqueous solvents such as methanol, ethanol, or ethyl acetate, a mix of water with a non-aqueous solvent, or using one of the extraction methods described above. The extracts, of *Aesculus californica* and *Crataegus mexicana* may be administered to humans, either each on their own or in combination, in therapeutic quantities to treat a variety of ailments including, but not limited to, cardiac and vascular disorders. These extracts may also be given as a dietary supplement to provide a cardio and vascular protective effect, particularly in case of cardiac ischeimia and life-threatening reperfusion-induced cardiovascular lesions. See U.S. Pat No. 5,925,355.

The extracts of *Aesculus californica* and *Crataegus mexicana* may further be combined with extracts from other plant species including, but not limited to, Bursera species, such as *Bursera microphylla*. The extracts of these other species may be prepared by any method known in the art or any of the methods described above.

In a further embodiment of the invention, the extracts of the *Aesculus californica* and *Crataegus mexicana* species and/or any other extracts to be mixed with either or both of the Aesculus and Crataegus extracts, may be separated to isolate specific bioactive substances to treat specific ailments. For example, hydroquinone may be isolated from the extracts of *Aesculus californica*. The separation may be performed using any separation technique known to those of skill in the art, or a packed column supercritical fluid chromatography separation method as described herein. Once separated, the hydroquinone acid may be administered by itself, or in combination with other bioactive substances from *Aesculus californica, Crataegus mexicana*, or other plant extracts, in therapeutic quantities to treat cardiac and vascular disorders.

In still a further embodiment, extracts of the Aesculus and Crataegus species alone or in combination with extracts from other plant or herb species, or isolated bioactive substances of the Aesculus and Crataegus species alone or in combination with bioactive substance of other plants or herbs, may be made into a capsule, pill, pastille, or elixir, in combination with other inert or pharmacological ingredients to be administered to patients.

iii) Extracts of Jojoba

In one embodiment of the present invention, extracts of *Simmondsia chinensis* (also known as *S. californica* and Jojoba), particularly extracts of defatted Jojoba meal, comprising simmondsin are prepared using water, non-aqueous solvents such as methanol, ethanol, or ethyl acetate, a mix of water with a non-aqueous solvent, water and non-aqueous solvents in sequence, or using one of the extraction methods described above. The extracts of Simmondsia may be administered to humans in therapeutic quantities as hunger satiation and weight reduction agents.

Extracts of Simmondsia may further be combined with extracts from other plant species. The extracts of the other species may be prepared by any method known in the art or any of the methods described above. In a preferred embodiment, simmondsin is separated from other substances in the Simmondsia extract. The separation may be performed using any separation technique known to those of skill in the art, or a packed column supercritical fluid chromatography separation method as described herein. Once separated, simmondsin may be administered by itself, or in combination with other bioactive substances from Simmondsia or other plant extracts, in therapeutic quantities as a hunger satiation or weight reduction agent. Therapeutically effective amount to satiate hunger are between 5 and 500 mg/kg body weight, preferably between 10 and 250 mg/kg body weight, more preferably between 20 and 100 mg/kg body weight and even more preferably between 25 and 50 mg/kg body weight.

In still a further embodiment, extracts of Simmondsia alone or in combination with extracts from other plant or herb species, or isolated simmondsin alone or in combination with bioactive substances of other plants or herbs, may be made into a capsule, pill, pastille, or elixir, in combination with other inert or pharmacological ingredients to be administered to patients.

iv) Extracts of Turnera and Pfaffia Species

In one embodiment of the present invention, extracts of Turnera species, such as *Turnera diffusa*, and Pfaffia species, such as *Pfaffia paniculata*, comprising various terpenes and phytochemicals are prepared. These extracts may be prepared using water, non-aqueous solvents such as methanol, ethanol, or ethyl acetate, a mix of water with a non-aqueous solvent, or using one of the extraction methods described above. The extracts of Turnera species and Pfaffia species may be administered to humans, either each alone or in combination with one another, in therapeutic quantities to treat a variety of ailments including, but not limited to, diabetes, rheumatism, ulcers, various cancers such as leukemia, chronic coughing, nephritis, orchitis, and spermatorrhea. These extracts may also be administered as a dietary supplement or health tonic to increase sexual drive, aid digestion, and increase fertility.

Extracts of Turnera and Pfaffia species may further be combined with extracts from other plant species including, but not limited to muira puama (a crude drug derived from various species including *Ptychopetalum olacoides, Liriosma ovata* and *Chaunochiton. kappleri*). The extracts of these other species may be prepared by any method known in the art or any of the methods described above.

In a further embodiment of the invention, the extracts of the Turnera and Pfaffia species and/or any other extracts to be mixed with the Turnera and/or Pfaffia extracts, may be separated to isolate specific bioactive substances to treat specific ailments. For example, β-sitosterol may be isolated from the extracts of *Turnera diffusa* and/or *Pfaffia paniculata*. The separation may be performed using any separation technique known to those of skill in the art, or s packed column supercritical fluid chromatography separation method as described herein. Once separated, the β-sitosterol may be administered by itself, or in combination with other bioactive substances from Turnera, Pfaffia, or other plant extracts, in therapeutic quantities as a health tonic to support either or both, male and/or female sexual function.

In still a further embodiment, extracts of the Turnera and Pfaffia species alone or in combination with extracts from other plant or herb species, or isolated bioactive substances of the Turnera and Pfaffia species alone or in combination with bioactive substance of other plants or herbs, may be made into a capsule, pill, pastille, or elixir, in combination with other inert or pharmacological ingredients to be administered to patients.

v) Extracts of Heimia Species

In one embodiment of the present invention, extracts of Heimia species, such as *Heimia solicifolia*, comprising a variety of alkaloids and quinones are prepared. These extracts may be prepared using water, non-aqueous solvents such as methanol and ethanol, a mix of water with a non-aqueous solvent, or using one of the extraction methods described above. The extracts of Heimia species may be administered to humans, either each alone or in combination, in therapeutic quantities to treat a variety of ailments including, but not limited to, joint and muscle inflammation. In a preferred embodiment, extracts of Heimia species are combined and administered in therapeutic quantities as a non-steroidal anti-inflammatory (NSAID).

Extracts of Heimia species may further be combined with extracts from other plant species. The extracts of these other species may be prepared by any method known in the art or any of the methods described above.

In a further embodiment of the invention, the extracts of a Heimia species and/or any other extracts to be mixed with other Heimia extracts, may be separated to isolate specific bioactive substances to treat specific ailments. For example, the alkaloids cryogenine and nesodine may be isolated from *Heimia salicifolia*. The separation may be performed using any separation technique known to those of skill in the art, or the packed column supercritical fluid chromatography separation method described herein. Once separated, cryogenine and nesodine may be administered by themselves, in combination, or in combination with other bioactive substances from *Heimia salicifolia*, or other plant extracts, in therapeutic quantities to treat inflammation of joints, muscles, or other tissue.

In still a further embodiment, extracts of the Heimia species alone or combined with extracts from other plant or herb species, or isolated bioactive substances of the Heimia species also alone or combined with bioactive substance of other plants or herbs, may be made into a capsule, pill, pastille, or elixir, in combination, with other inert or pharmacological ingredients to be administered to patients.

The following experiments are offered to illustrate embodiments of the invention, and should not be viewed as limiting the scope of the invention.

EXAMPLES

Example 1

Supercritical Fluid Extraction—$CO_2$ Extraction

The kavalactone supercritical fluid extractions (SFE) described in Examples 1–2 were performed using a 3 mL extraction vessel. Each extraction contained 0.5 grams of finely ground Kava root. Various experimental conditions, as described below, were used to determine the conditions that maximized recovery of kavalactones. The SFE procedures were performed for 60 minutes at a flow rate of 2 mL/min of liquid $CO_2$.

Supercritical fluid extractions were performed at 350 atm and 450 atm. A solid phase trap packed with C18 was used to collect the extracted analytes. The trap temperature was set at +10C. After completing each supercritical fluid extraction, the trap was rinsed with 10 mL of 50/50% mixture of ethanol/$CH_2CH_2$. The extract volume was then adjusted to 25 mL using $CH_2CH_2$.

Kavalactone Standards—Because no pure kavalactone standards were available, the SFE extracts were compared with Kava root extracts obtained by conventional sonication methods. For this purpose 0.5 gram of Kava root was sonicated for 30 minutes in 25 mL of 50/50 $CH_2CH_{12}$/MeOH as an extraction solvent. The extract was then filtered through a 2 $\mu$m filter paper. The extract was then analyzed with a Hewlett Packard Model 5890 Gas Chromatograph coupled to a Hewlett Packard Model 5972 Mass Spectrometer. Extract from sonication was assumed to yield a 100% recovery of all kavalactones in the root sample. Kavalactone recovery using $CO_2$ SFE was compared with the kavalactone recover using $CH_2C12$/MeOH sonication.

Columns 1 and 2 of Table 1 shows SFE recoveries of different kavalactones from Kava root using different SFE conditions. The recoveries are expressed as a percentage of the recovery obtained by conventional sonication methods. Peak identification were obtained by comparison of three most intense ions in mass spectrum of each peak and those reported by Viorica Lopez-Avila et al. V. Lopez-Avila and Benedicto, J. High Resolut. Chromatogr., 20, 555 (1997).

TABLE 1

Percent Recovery of Different Kavalactones from Kava Root Using Supercritical Fluid Extraction*

| Compound | 350 atm, 60° C. 60° C. 100% $CO_2$ | 450 atm 60° C. 100% $CO_2$ | 350 atm 60° C. 85% $CO_2$ 15% EtOH | 450 atm 60° C. 85% $CO_2$ 15% EtOH |
|---|---|---|---|---|
| 7,8-Dihydro-kavain | 92.9% (7) | 97.5% (6) | 92.7% (2) | 91.1% (5) |
| Kawain | 93.6% (5) | 100.0% (4) | 102.9% (4) | 107.0% (4) |
| 5,6-Dihydro-kavain | 86.1% (8) | 80.3% (5) | 74.0% (8) | 79.9% (7) |
| 5,6,7,8-Tetra-hydroangonin | 97.9% (5) | 92.9% (8) | 96.4% (4) | 106.0% (6) |
| Dihydro-methysticin | 93.2% (8) | 88.4% (6) | 95.3% (8) | 104.1% (4) |
| Yangonin | 84.7% (11) | 67.6% (12) | 72.5% (9) | 84.1% (9) |
| Methysticin | 95.9% (7) | 66.2% (10) | 111.1% (7) | 137.6% (12) |

* = % recovery are based on comparison of SFE with 50/50 CH2Cl2/MeOH sonication extraction.
( ) = % RSD for three replicate extractions.

Example 2

$CO_2$ Extractions with Ethanol

Another supercritical fluid chromatography extraction was performed to test the efficiency of obtaining kavalactones using a mixture of $CO_2$ and ethanol. In this experiment an extraction solution of 85% $CO_2$ and 15% ethanol was used at 350 atm and 450 atm of pressure. The trap temperature was held at 60° C. Table 1 shows that some species of kavalactones, notably Kavain and Methysticin were more efficiently extracted from SFE than with sonication. Table 2 shows the retention times, molecular weights (MW), and three most intense ions in the mass spectra analysis of kavalactones isolated through SFE, as described above.

TABLE 2

Three Most Intense Ions Found in
the Electron Impact Mass Spectra
of Kavalactones Root Extract via SFE

| No. | Compound Name | Retention Time | MW | Three most intense ions (m/z) |
|---|---|---|---|---|
| 1 | 7,8-Dihydrokavain | 27.85 | 232 | 127 (100), 91, 117 |
| 2 | Kavain | 29.05 | 230 | 98 (100), 68, 69 |
| 3 | 5,6-Dihydrokavain | 29.85 | 228 | 228 (100), 157, 69 |
| 4 | 5,6,7,8-Tetrahydro-angonin | 30.71 | 262 | 121 (100), 147, 262 |
| 5 | Dihydromethysticin | 31.96 | 276 | 135 (100), 276, 136 |
| 6 | Yangonin | 32.95 | 258 | 258 (100), 187, 230 |
| 7 | Methysticin | 33.16 | 274 | 148 (100), 135, 274 |

FIG. 1 shows the Gas Chromatograph/Mass Spectroscopy (GC/MS) separation of kavalactones extracted using SFE. FIGS. 2–8 show mass spectra of each kavalactone listed in Table 2. Table 3 shows retention times and four most intense ions for the mass spectra of other peaks that eluted earlier than the major kavalactones.

TABLE 3

Three Most Intense Ions Found
in the Electron Impact Mass Spectra
of Peaks Eluted Earlier than the
Major Kavalactones Extracted via SFE

| No. | Compound Name | Retention time | Four most intense ions (m/z) |
|---|---|---|---|
| 1 | Unknown | 19.40 | 91 (100), 65, 188, 97 |
| 2 | Unknown | 22.01 | 186 (100), 95, 128, 155 |
| 3 | Unknown | 23.01 | 121 (100), 218, 77, 78 |
| 4 | Unknown | 24.35 | 135 (100), 77, 232, 136 |
| 5 | Unknown | 26.93 | 135 (100), 230, 115, 128 |

Figure 14:
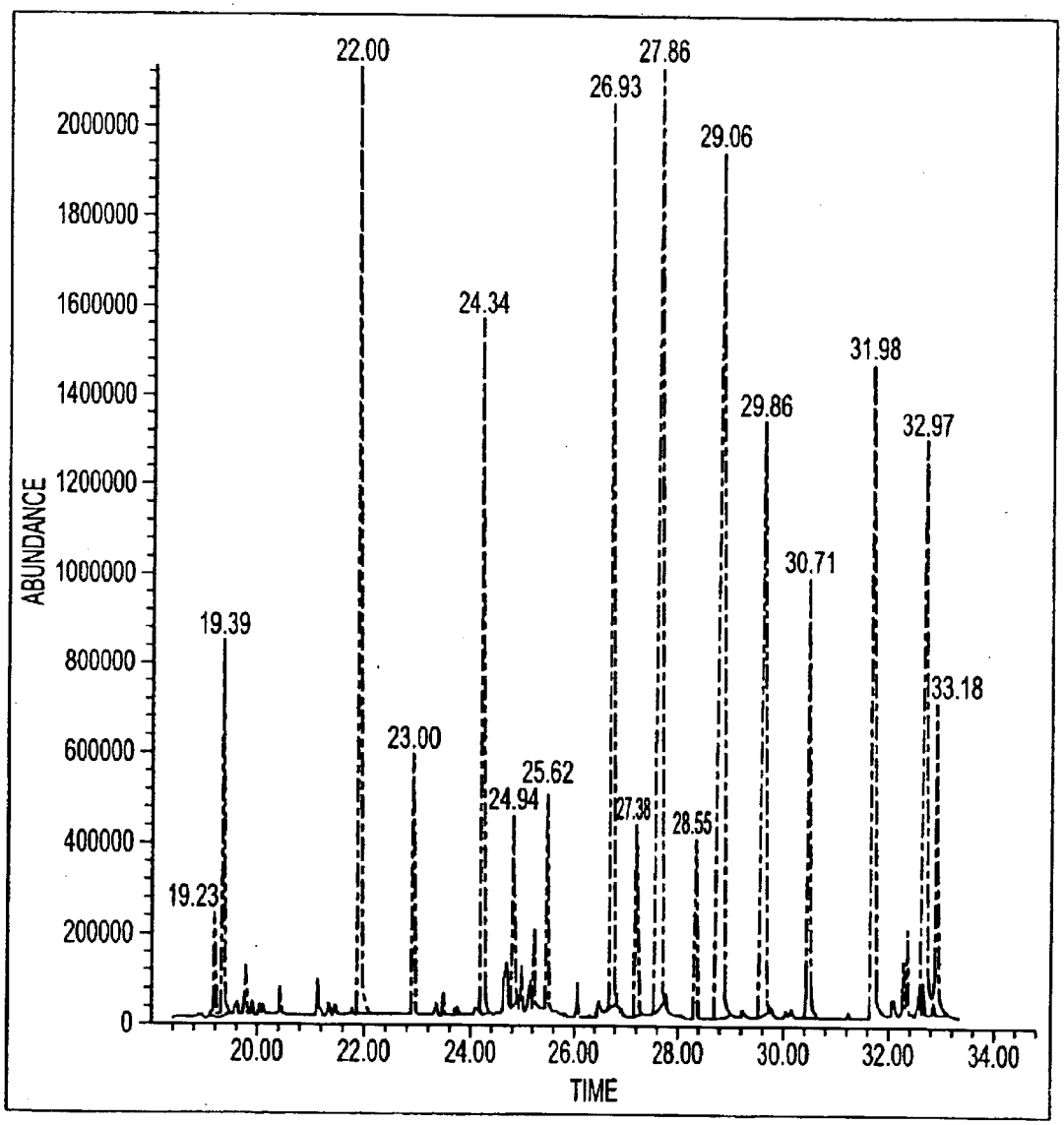
FIG. 14 GC/MS chromatogram of kavalactones extracted via sonication.

FIGS. 9–13 show spectra of other major peaks which eluted before kavalactones (tR=19.40, 22.1, 23.01, 24.35, and 26.93 min). It is believed that the peak with tR=23.1 is a spike (ghost peak) which appeared in MS. FIG. 14 shows GC/MS chromatogram of kavalactones extracted via sonication.

To compare the absolute weights of extracts obtained by SFE and sonication, 0.5 grams of Kava root was extracted via both SFE and sonication, as discussed above. Each extract was then transferred to a vial of known weight. The solvent in each extract was evaporated under a stream of nitrogen. Table 4 shows the weight and percent of extracted analytes from 0.5 gram of Kava root using both an SFE and sonication technique.

TABLE 4

Extracted from Kava root via
Supercritical Fluid Extraction and
Solid-Liquid Extraction (Sonication)

| | Sample weight extraction (g) | Weight of extract (g) | Percent weight of analyte extracted |
|---|---|---|---|
| SFE; 350 atm, 60° C. 85/15 $CO_2$EtOH 2 mL/min | 1.0 | 0.0716 | 7.16 |
| SFE, 350 atm, 60° C. 85/15 $CO_2$EtOH 2 mL/min | 0.5 | 0.038 | 7.6 |

TABLE 4-continued

Extracted from Kava root via
Supercritical Fluid Extraction and
Solid-Liquid Extraction (Sonication)

| | Sample weight extraction (g) | Weight of extract (g) | Percent weight of analyte extracted |
|---|---|---|---|
| Sonication, 15 mL 50/50 $CH_2Cl_2$/MeOH for 30 min | 0.5 | 0.039 | 7.8 |

These results show that more than 90% of the measured kavalactones can be extracted via pure $CO_2$, however, a more complete extraction of kavalactones was found using a composition of 85% $CO_2$ and 15% ethanol as the supercritical fluid.

Example 3

Separation of Kavalactones Using Supercritical Fluid Chromatography

The following separations were performed using a Hewlett Packard Model G1205A supercritical fluid chromatograph (SFC) system equipped with a variable UV detector. The detection wavelength was set to 254 nm. Different columns and chromatography conditions were applied in order to determine the most advantageous separation of kavalactones.

Figure 15:
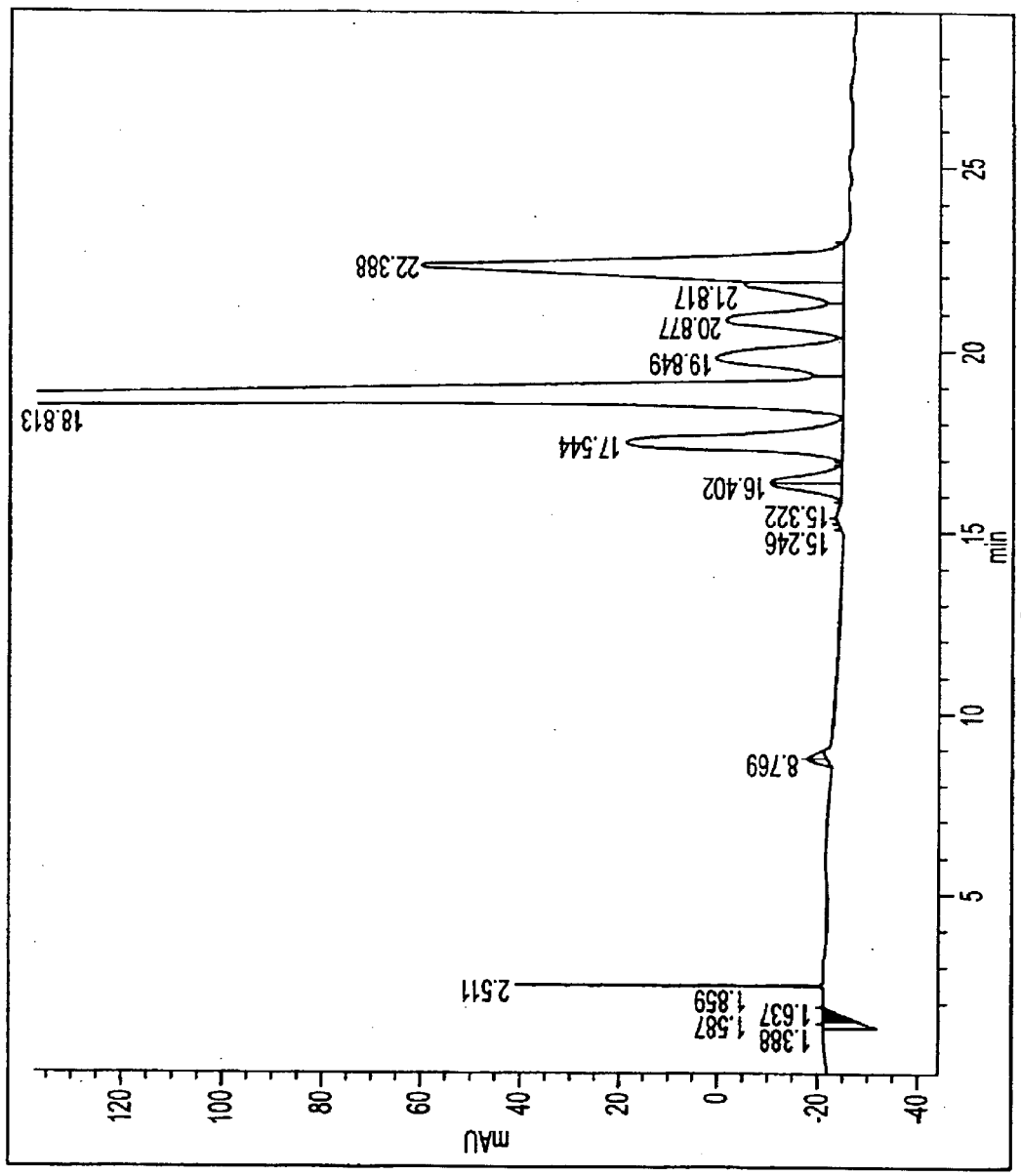
FIGS. 15–17 Results of experiments wherein kavalactone extracts were subjects to SFC using NH2, DIOL, and CN columns.
Figure 16:
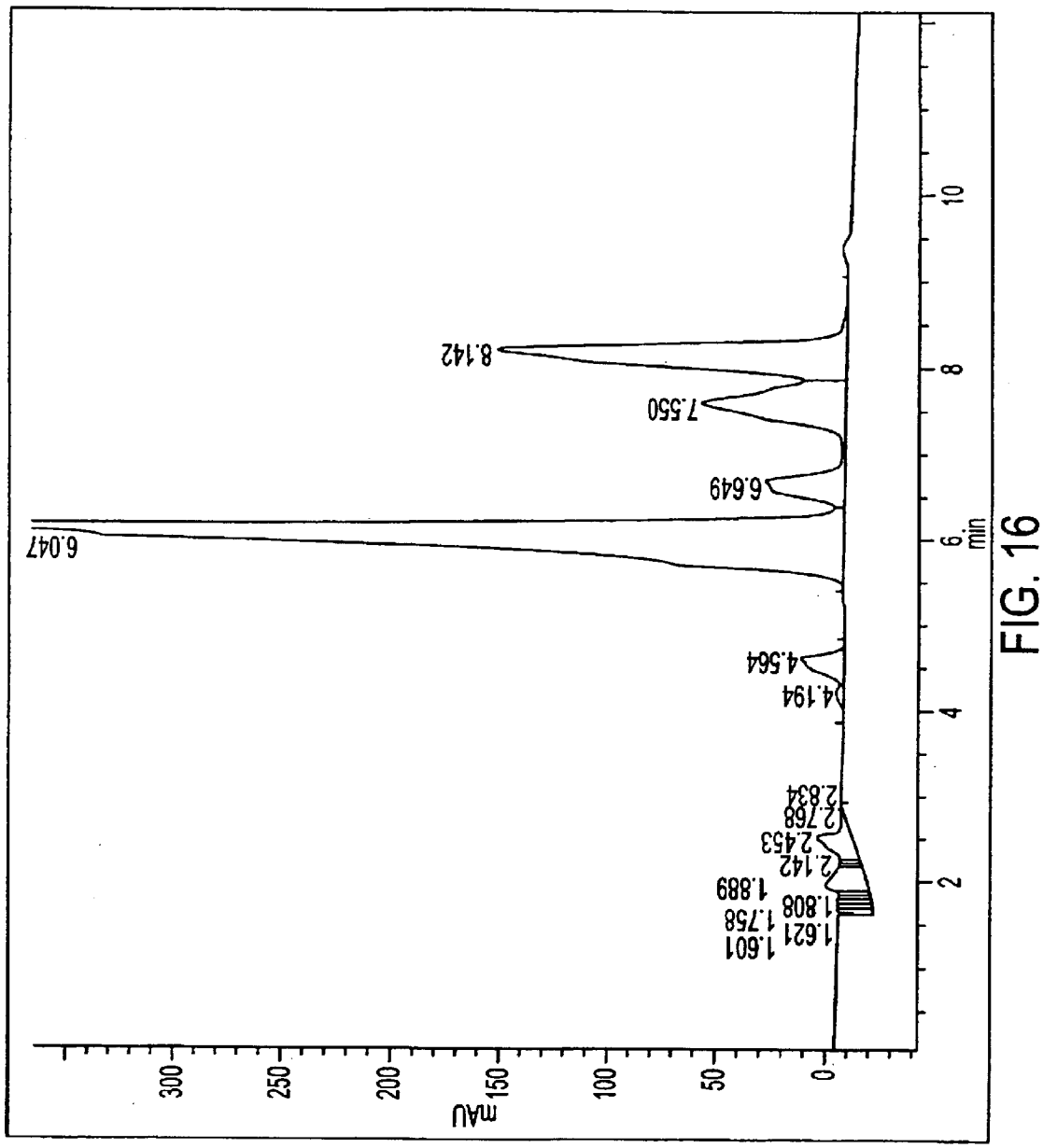
Figure 17:
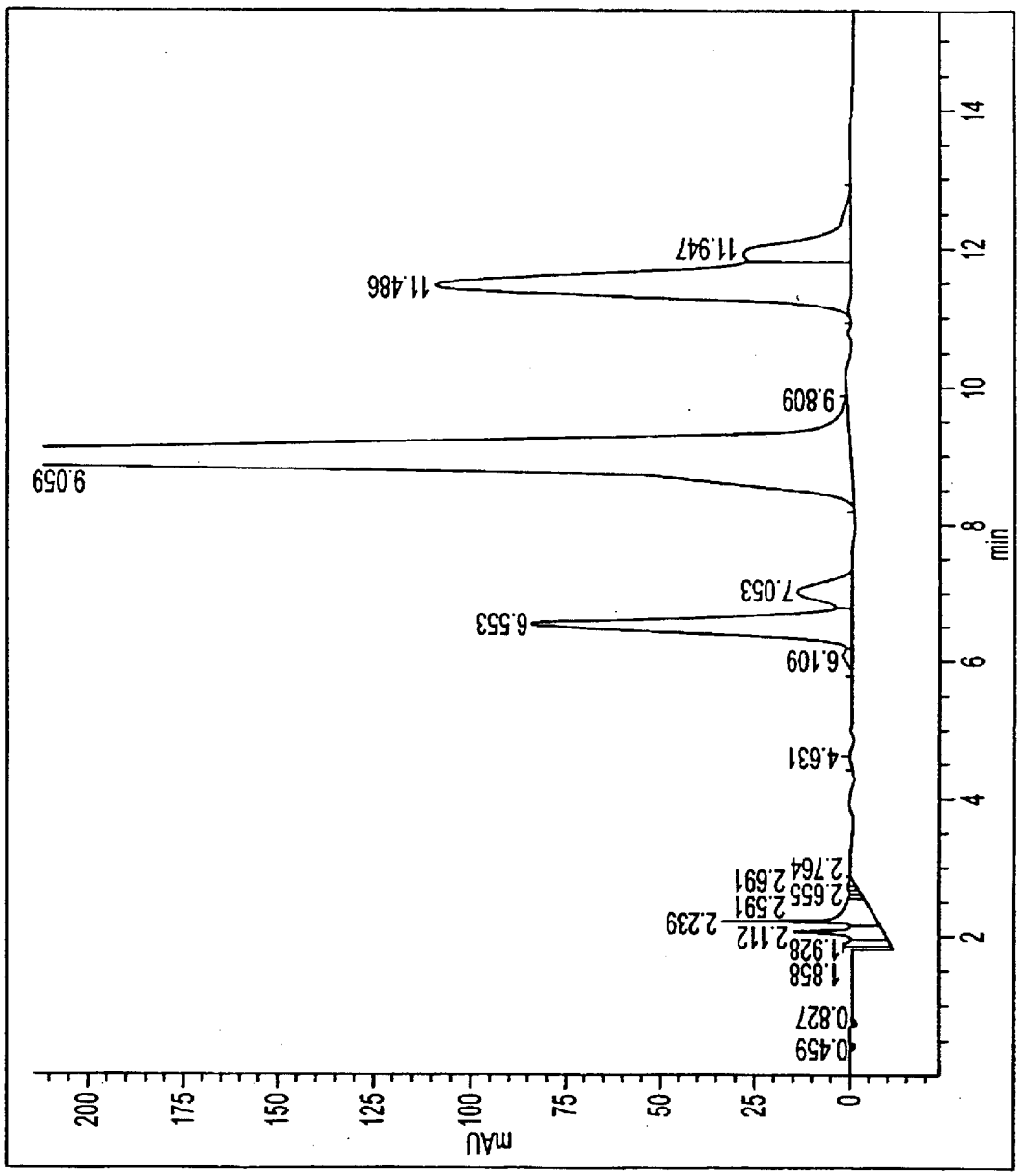

FIGS. 15–17 show results of experiments wherein kavalactone extracts were subjected to SFC using $NH_2$, DIOL, and CN columns. The chromatography conditions for the $NH_2$ column was: Column Material: $NH_2$ with water; Brand Name: Altec Sphenosorb; Length: 25 cm; Inner Diameter: 4.6 mm ID; Pressure: 125 atm; Temperature: 60° C.; Flow Rate: 2 mL/min liquid $CO_2$.

The modifier programming started with 2/98% MeOH/$CO_2$ hold for 3 min., and then increased to 10/90% MeOH/$CO_2$ at a rate of 0.4% min. The chromatography conditions for the DIOL column was: Column Material: DIOL; Brand Name: Vydac Model Supleco; Length: 25 cm; Inner Diameter: 4.6 mm ID; Pressure: 125 atm; Temperature: 60° C.; Flow Rate: 2 mL/min liquid $CO_2$.

Modifier programming started with 2/98% MeOH/$CO_2$ hold for 3 min., and then increased to 10/90% MeOH/$CO_2$ at a rate of 0.4% min. The chromatography conditions for the Cyano (CN) column was: Column Material: CN; Brand Name: Altec; Length: 25 cm; Inner Diameter: 4.6 mm ID; Pressure: 275 atm; Temperature: 60° C.; Flow Rate: 2 mL/min liquid $CO_2$. Modifier programming started with 2/98% MeOH/$CO_2$ at a rate of 0.4% min.

As can be seen upon reference to FIGS. 15–17, the best kavalactone separations were obtained with the $NH_2$ column. Both the CN and DIOL column provided some separation, however co-elution of components was observed.

Example 4

Optimization of CN Column Conditions

Figure 18:
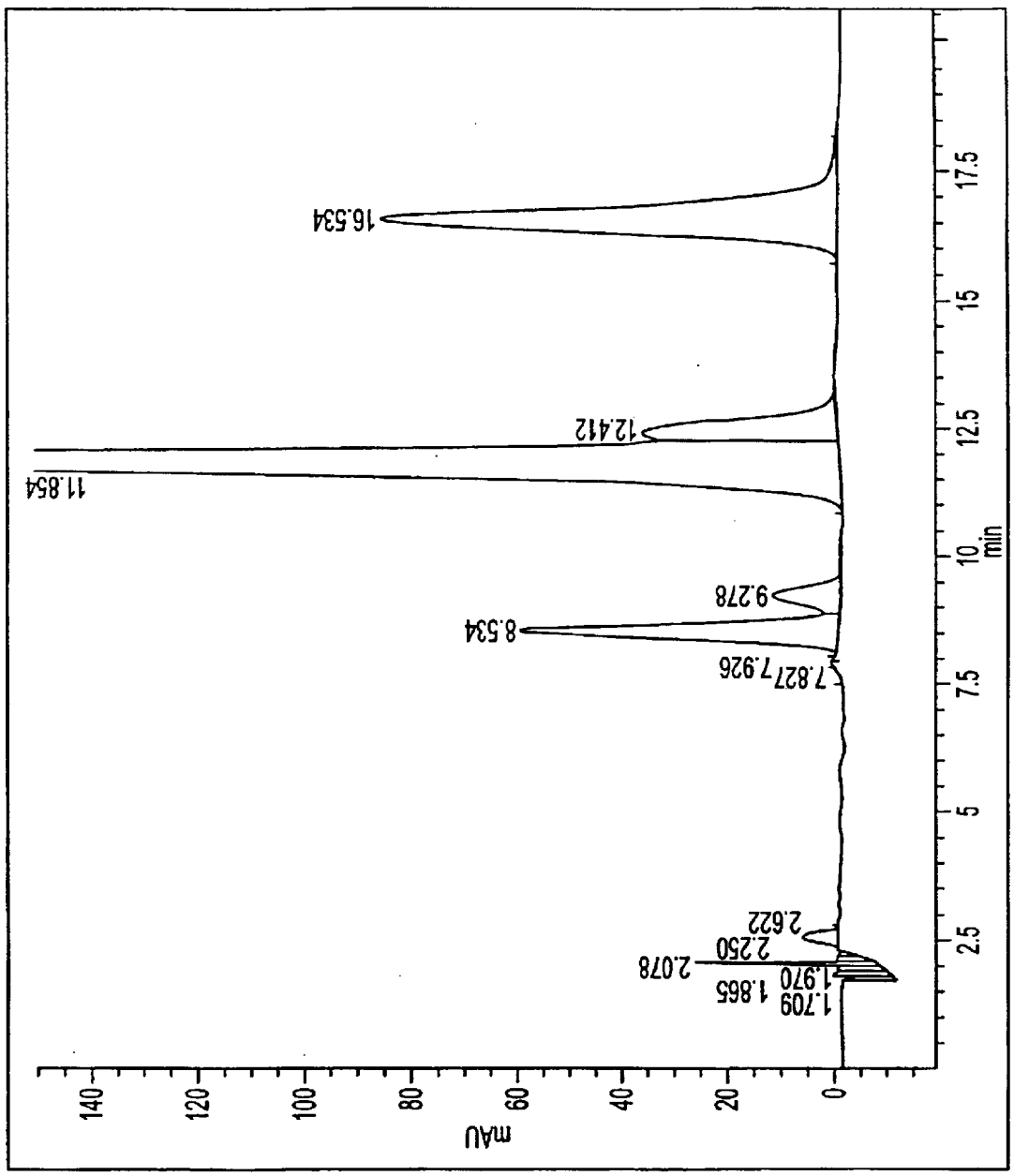
FIG. 18 Results of an experiment wherein kavalactone SFE extracts were separated with SFC at a higher temperature (80° C.) using the CN column. All other chromatography conditions were the same as described for CN above.

FIG. 18 shows the results of an experiment wherein kavalactone SFE extracts were separated with SFC at a higher temperature (80° C.) using the CN column. All other chromatography conditions were the same as described for CN above. Selectivity of the column at 80° C. was changed in that some of the lactones were separated which had co-eluted at 60° C. In addition, some lactones which co-eluted at 80° C. were separated previously at 60° C.

Figure 19:
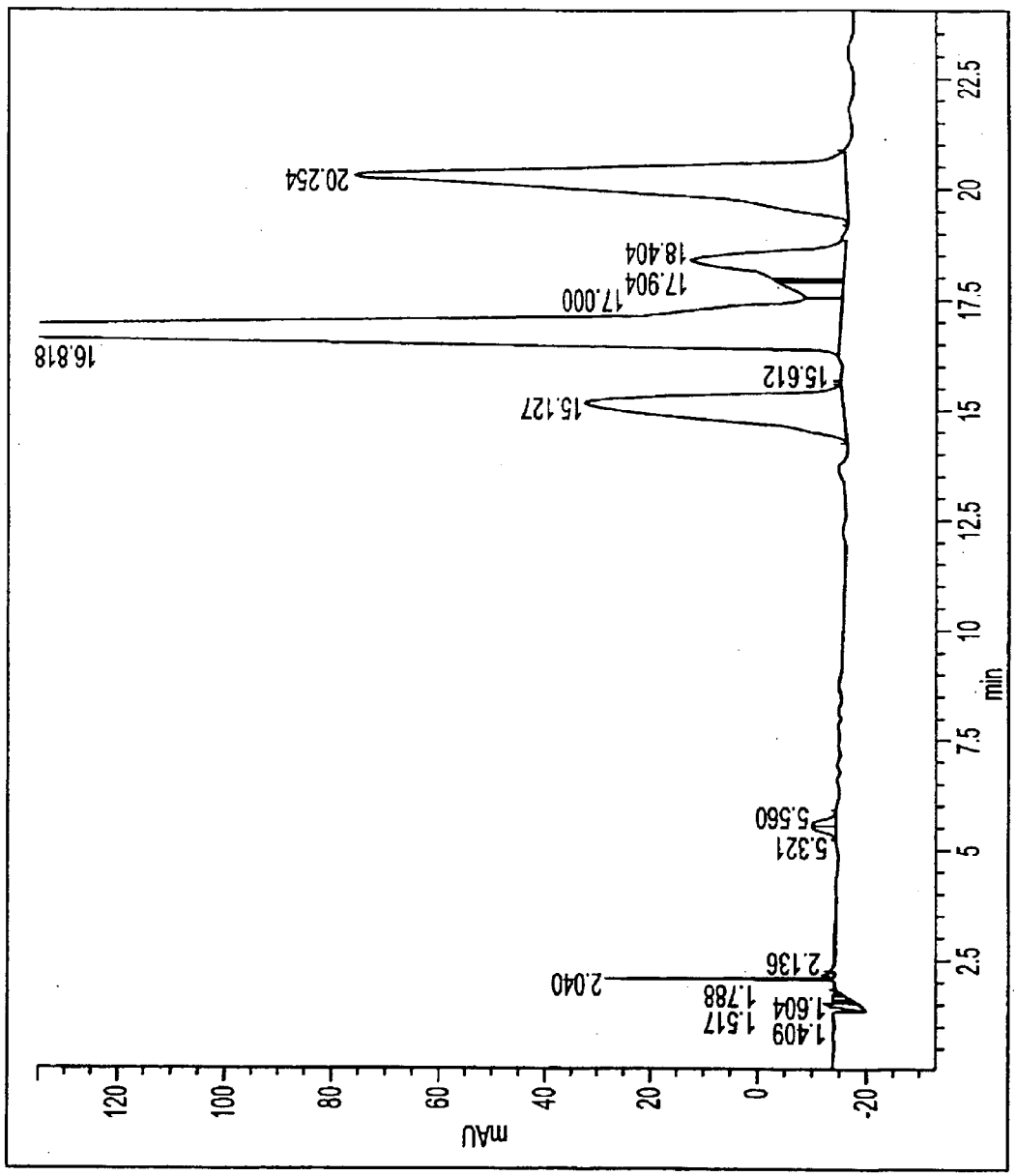
FIG. 19 Pressure (125 atm) did not change the selectivity of the column.

Separation of kavalactones did not improve at a lower temperature (40° C.) using a CN column under the same conditions. Additionally, a change in modifier concentration (modifier programming start with 2/98% MeOH/$CO_2$ hold for 3 min., and then increased to 10/90% MeOH/$CO_2$ at rate of 0.5%/min.) and pressure (125 atm) did not change the selectivity of the column as shown in FIG. 19.

Example 5

Optimization of $NH_2$ Column Conditions

Figure 20:
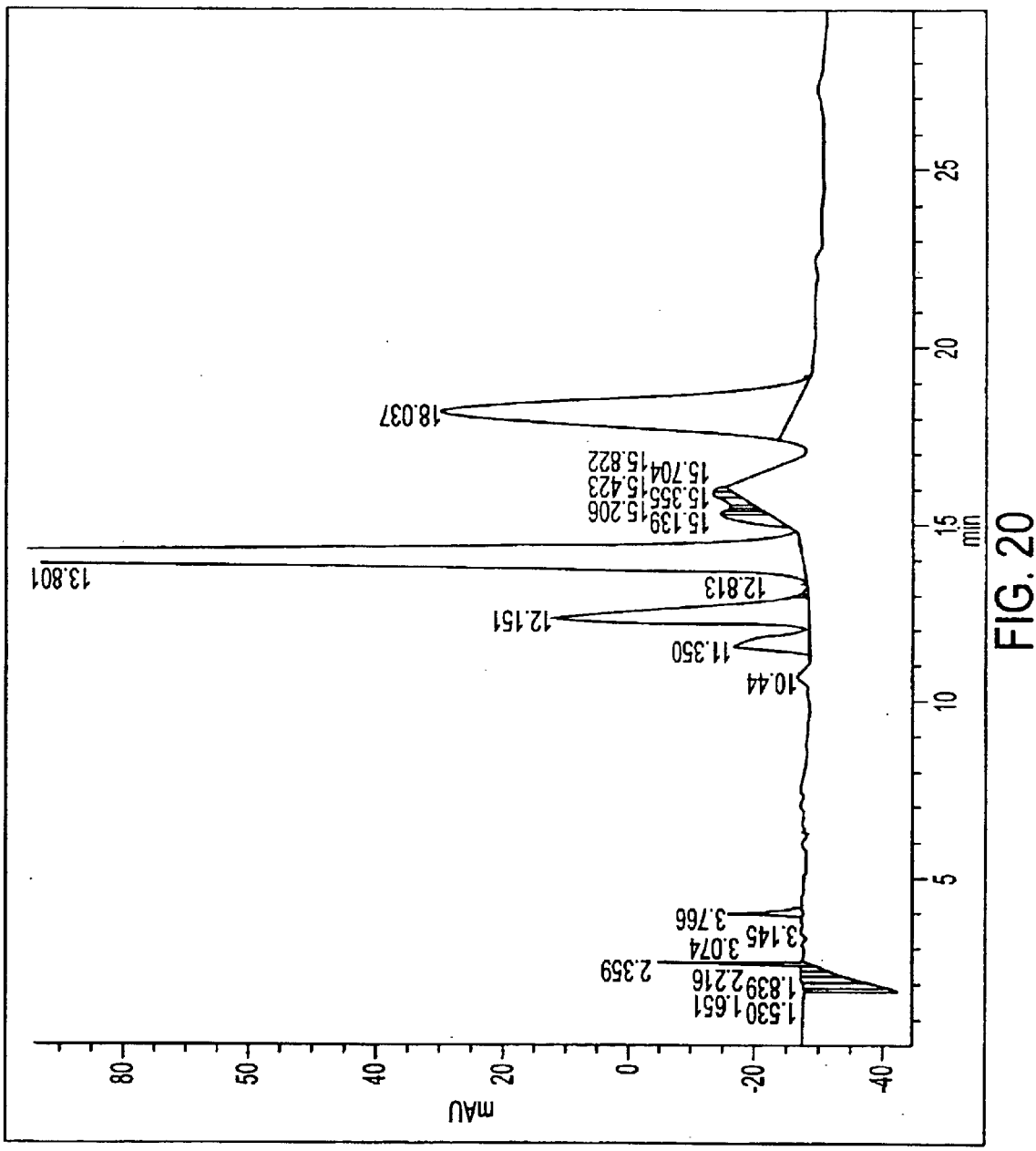
FIGS. 20 and 21 Separation of kavalactone extracts on $NH_2$ columns at 40° C. and 80° C., respectively.
Figure 21:
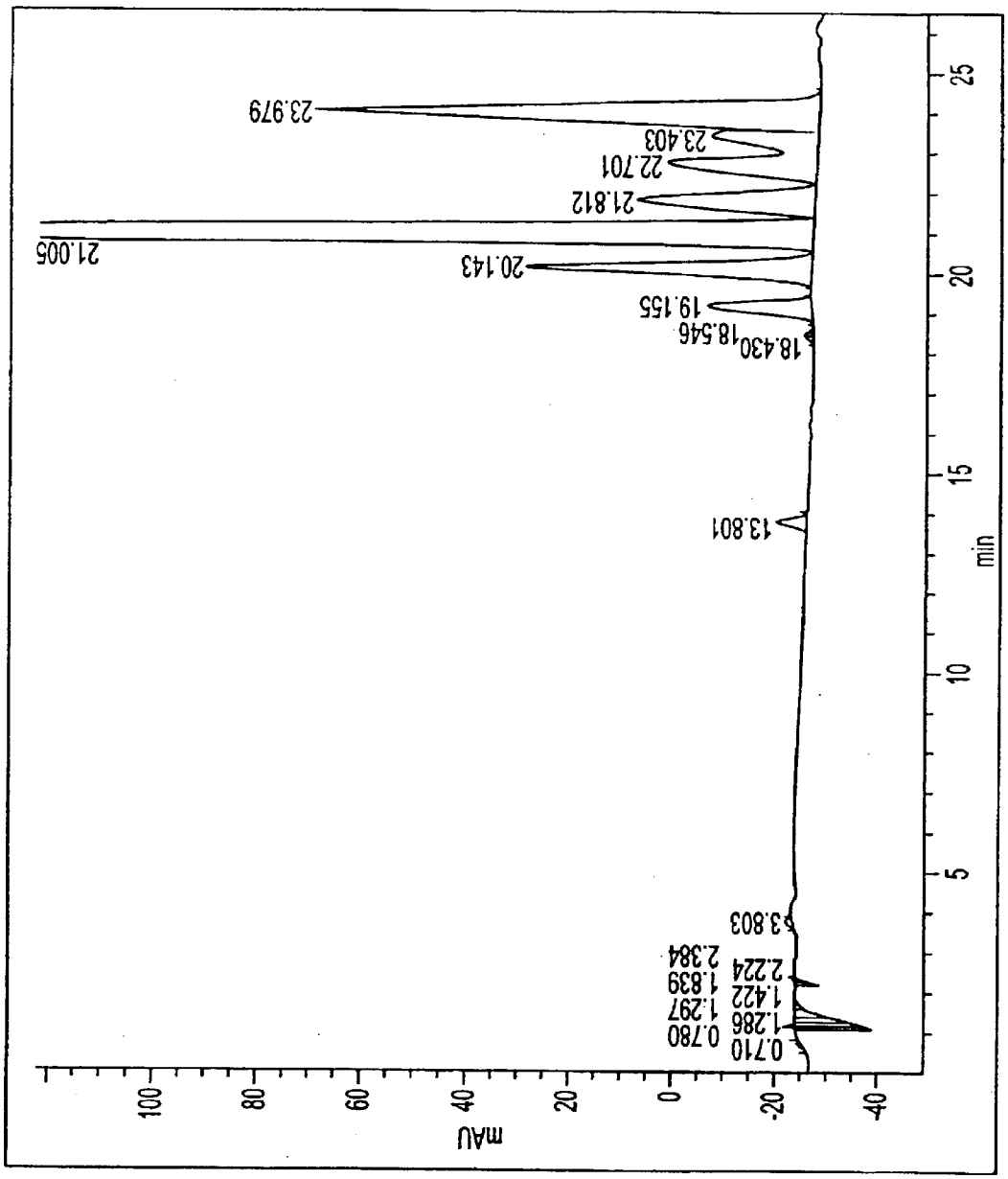

The SFC separation of kavalactone SFE extracts were then optimized with an $NH_2$ chromatography column under varying conditions. FIGS. 20 and 21 show separation of kavalactone extracts on $NH_2$ columns at 40° C. and 80° C., respectively. The chromatography conditions were Pressure 125 atm, and flow rate of 2 mL/min liquid $CO_2$. Modifier programming started with 2/98% MeOH/$CO_2$ hold for 3 min., and then increased to 10/90% MeOH/$CO_2$ at a rate of 0.4%/min. As shown in FIG. 20, the lower temperature separations decreased column selectivity and lactones co-eluted. At higher temperatures, a better solution was obtained for components eluted at 23.39 and 23.97 minutes (FIG. 21) compared to the separation obtained at 60° C. (FIG. 15).

Figure 22:
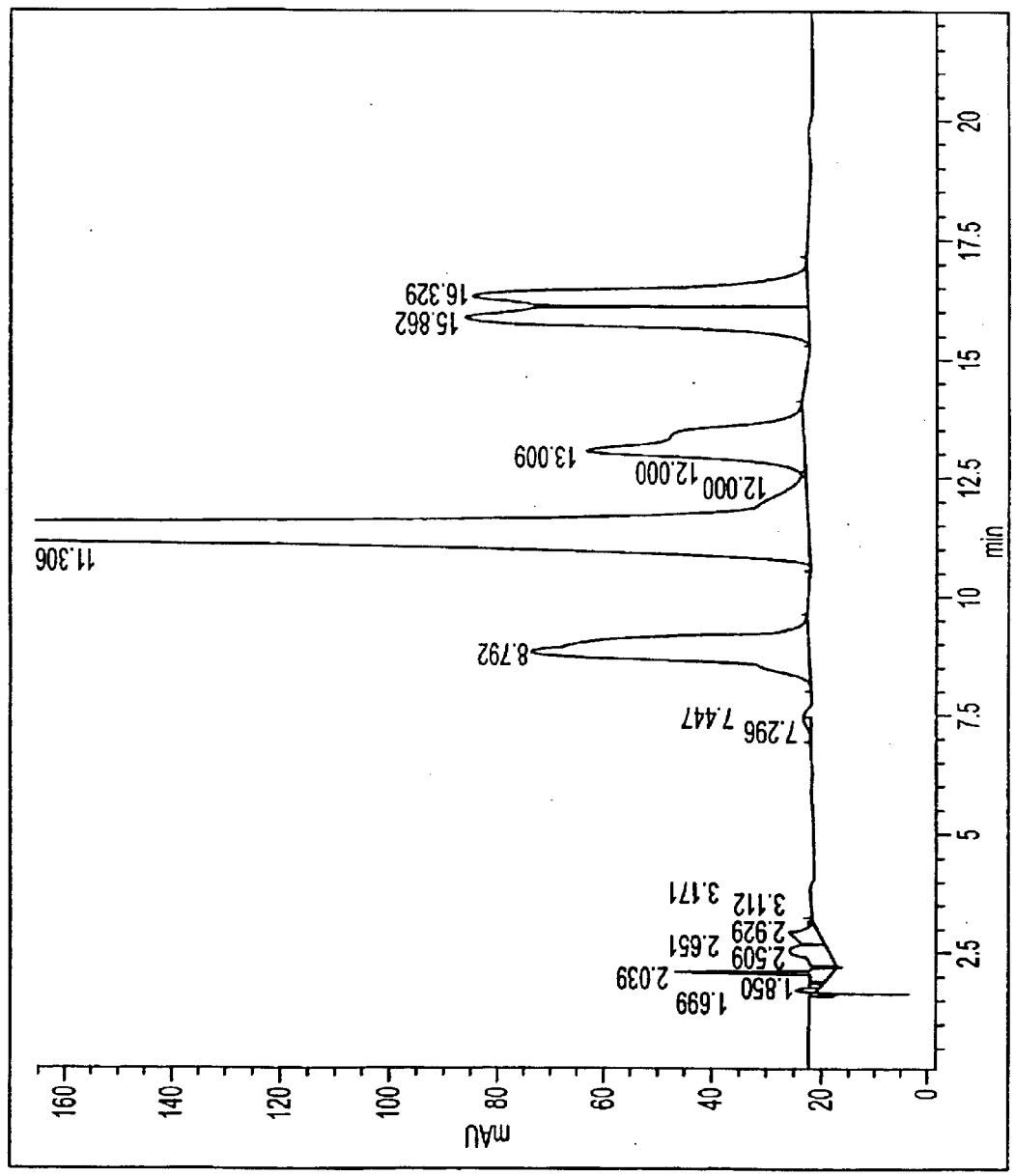
FIG. 22 Results of a separation of the same Kava root extract on an $NH_2$ column, using the same conditions as described with FIG. 21, with the exception that pressure was increased to 275 atm.
Figure 23:
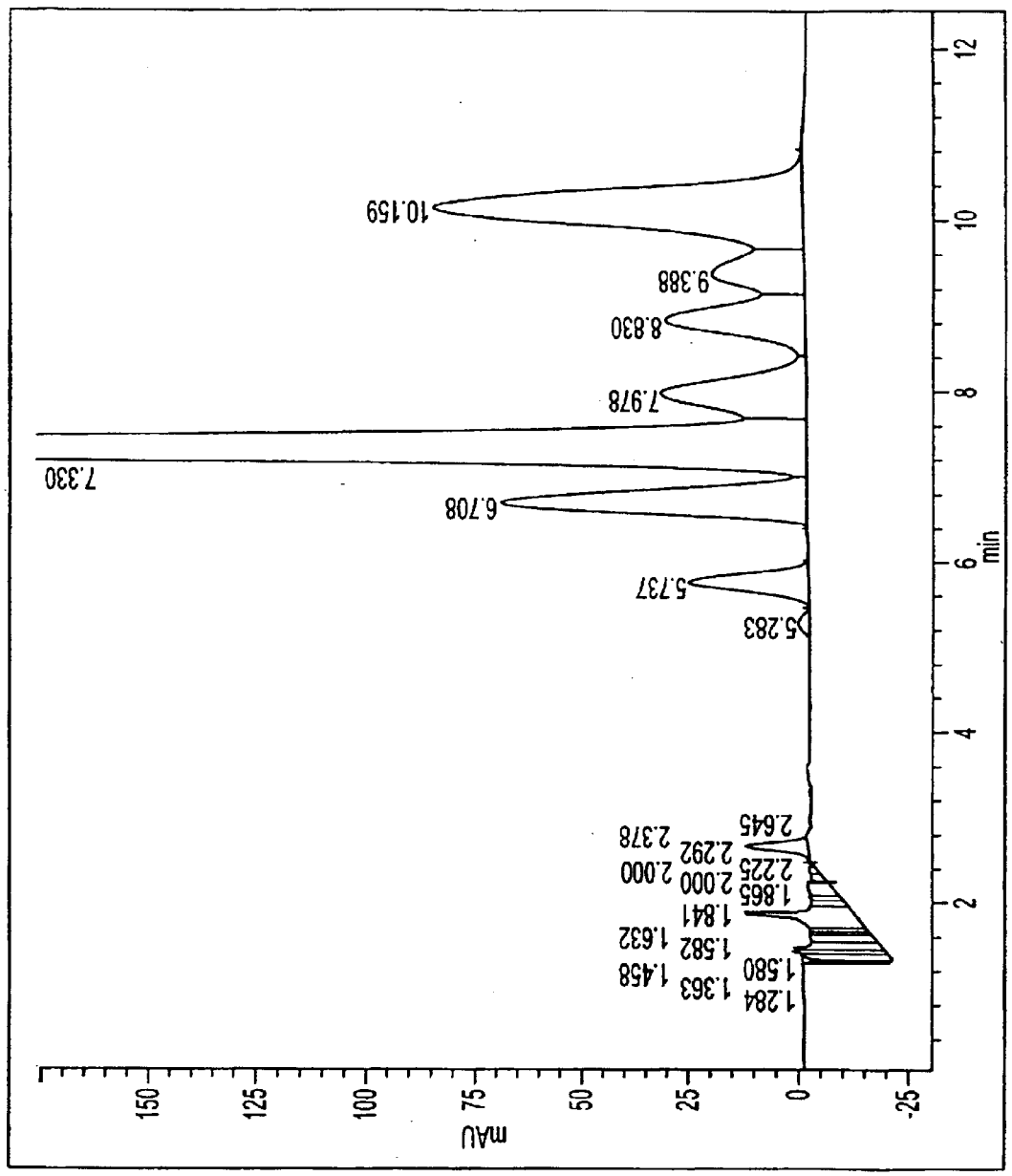
FIG. 23 For this experiment the same pressure (125 atm), temperature (80° C.), flow (2 mL/min of liquid $CO_2$), and column ($NH_2$) was used with the exception that the modifier programming started with 7/93% $MeOH/CO_2$ hold for 3 minutes and then increased to 10/90% $CO_2/MeOH$ at the rate of 0.2% minutes.
Figure 24A:
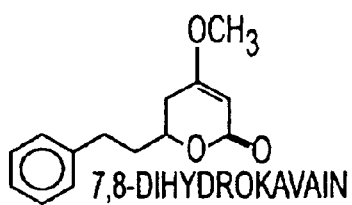
FIG. 24 Chemical structure of seven identified kavalactones.
Figure 24B:
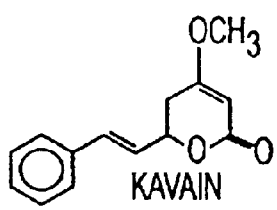
Figure 24C:
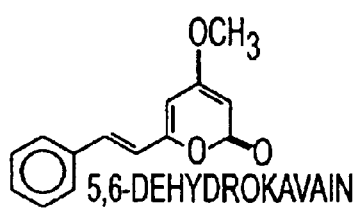
Figure 24D:
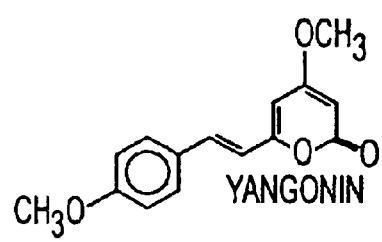
Figure 24E:
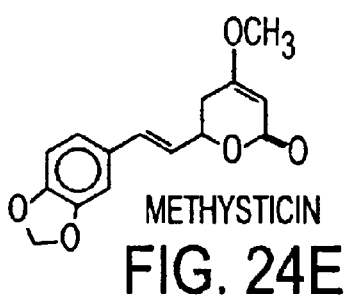
Figure 24F:
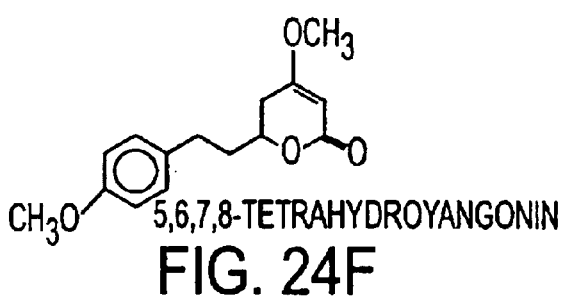
Figure 24G:
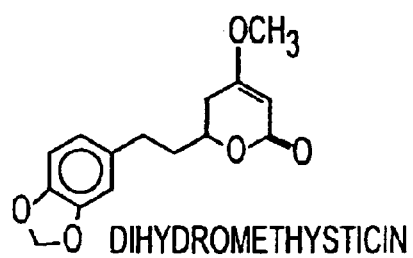

FIG. 22 shows the results of a separation of the same Kava root extract on an $NH_2$ column, using the same conditions as described with FIG. 21, with the exception that pressure was increased to 275 atm. Co-elution of several components was observed. The modifier concentration was then varied to optimize the elution time of the analytes. For this experiment the same pressure (125 atm), temperature (80° C.), flow (2mL/min of liquid $CO_2$), and column ($NH_2$) was used with the exception that the modifier programming started with 7/93% MeOH/$CO_2$ hold for 3 minutes and then increased to 10/90% $CO_2$/MeOH at the rate of 0.2% minutes (FIG. 23). A similar separation as FIG. 21 was obtained. However, the analysis time was reduced from 24 minutes to 11 minutes.

The 7 peaks which were obtained using the $NH_2$ column are the kavalactones that were identified using the supercritical fluid extraction of Kava root and GC/MS. The area percentage of each peak in the chromatogram was as follows: 3, 9.5, 50, 6.9, 5.8, 4.0 and 20%.

Example 6

SFE of Kavalactones with $CO_2$ and 15% Ethanol-modified $CO_2$

All supercritical fluid extractions described in the Examples were performed using an Isco-Suprex (Lincoln, Neb.) Prepmaster equipped with an ACCUTRAP™ and variable flow restrictor. In each extraction 0.5 gram of Kava root, which was previously ground, was used. Extractions were performed for 60 minutes at a flow rate of 2 mL/min of liquid $CO_2$. Two pressures (350 and 450 atm) at 60° C. were used for extractions. A solid phase trap packed with C18 was used to collect the extracted analytes. Trap temperature was set to +10° C. when pure $CO_2$ was used as an extraction fluid, while trap temperature was set to 60° C. when 15% ethanol-modified $CO_2$ was used. After completion of each extraction, the trap was rinsed with 10 mL or 50/50 mixture of ethanol/$CH_2CH_{12}$. The extract volume was then adjusted to 25 mL using $CH_2Cl_{12}$.

Because there was no standard to determine extraction efficiency of kavalactones, all SFE extracts were compared with a liquid-solid extraction (LSE) of Kava root via a sonication method. The LSE was performed by sonicating 0.5 gram of Kava root with 10 mL of 50/50% MeOH/$CH_2CH_{12}$ for 60 minutes at room temperature using a Fisher Scientific (Pittsburgh, Pa.) sonication bath. Next, the supernatant was filtered through a Gelman 0.45 μm nylon Acrodisc filter. The final volume was adjusted to 50 mL and analyzed via GC/MS. This extraction was assumed to yield 100% recovery of all kavalactones from the root.

A Hewlett-Packard G1205A Supercritical Fluid Chromatography (SFC) system with a variable UV detector equipped with a high pressure flow cell was used to obtain all SFC separations. Detection of lactones was monitored at 254 nm. The same instrument was used for semi-preparative scale separations but using the maximum flow rate (4 mL/min).

Table 5 lists the columns and the corresponding vendors that were used in this study. For semi-preparative scale separations, the column was 250×10 mm, dp=5 μm; whereas, analytical scale studies employed columns that were 250×4.6 mm, dp=5 μm. Seven kavalactones were identified in the supercritical extract using GC/MS (Hewlett Packard 5890 gas chromatography equipped with 5971A mass selective detector, and 7673 autosampler, Wilmington, Del.). All GC separations were obtained on a 30 m×0.25 mm i.d.×0.25 μm dp DB-5 (J & W Scientific, Folson, Calif.) fused silica capillary column. The column temperature was held at 50° C. for 3 minutes, then programmed to 280° C. at a rate of 10° C./min.

TABLE 5

Columns Used in This Study*

| Column | Manufacture |
|---|---|
| Spherisorb NH2 | Alltech |
| Altima Cyano | Alltech |
| Supelcosil LC-DIOL | Supleco |
| C4 Protein | Vatic |
| Diphenyl | Vatic |

*250 × 4.6 mm, 5F dp

HPLC grade methanol and ethanol were purchased from EM Science (Gibbstown, N.J.). SFE/SFC grade CO2 was used for both supercritical fluid extraction and supercritical fluid chromatography studies and was obtained from Air Products and Chemicals Co. (Allentown, Pa.).

Various conditions were used to obtain quantitative extraction of kavalactones from Kava root. Two pressures using both pure and 15% ethanol-modified C02 were studied to determine the extraction efficiency of kavalactones from Kava root. To determine the extraction efficiency of each lactone, an identical amount of Kava root was extracted via solid-liquid extraction (sonication) using 50/50% $CH_2CH_{12}$/MeOH as an extraction solvent. Results of the liquid-solid extraction were assumed to yield 100% recovery. Table 6 shows the relative extraction efficiency of each kavalactone extracted from Kava root under several SFE conditions. The results reveal that most of the kavalactones can be extracted with near critical or super critical gasses such as, for example, nitrogen, hydrogen or, preferably, butane, propane or freon. An efficiency of greater than 90% was obtained using pure $CO_2$ at 350 atm and 60° C. Even higher extraction efficiency of kavalactones from Kava root can be obtained using 15% ethanol-modified $CO_2$. However, their extraction efficiency using pure $CO_2$ as an extraction fluid was less than 25%. This could be due to the larger sample size which was used in their extraction compared to results or the differences may be reflective of the different trapping schemes used in the two studies.

TABLE 6

Percent Recoveries of Kavalactones from Kava Root Using SPE*

| Compound | 350 atm, 60° C. 100% $CO_2$ | 450 atm, 60° C. 100% $CO_2$ | 350 atm, 60° C. 85/15 $CO_2$/ EtOH | 450 atm, 60° C. 85/15 $CO_2$/ EtOH |
|---|---|---|---|---|
| 7,8-Dihydro-kavain | 92.9 (7) | 97.5 (6) | 92.7 (2) | 91.1 (5) |
| Kavain | 93.6 (5) | 100.0 (4) | 102.9 (4) | 107.0 (4) |
| 5,6-Dihydro-kavain | 86.1 (8) | 80.3 (5) | 74.0 (8) | 79.9 (7) |
| Dihydro-methysticin | 93.2 (8) | 88.4 (6) | 95.3 (8) | 104.1 (4) |
| Yangonin | 84.7 (11) | 67.6 (12) | 72.5 (9) | 84.1 (9) |
| Methysticin | 95.9 (7) | 66.2 (10) | 111.1 (7) | 137.6 (12) |
| 5,6,6,8-Tetra hydro-angonin | 97.9 (5) | 92.9 (8) | 96.4 (4) | 106.02 (6) |

* = % recoveries are based upon comparison with 50/50 CH2Cl2/MeOH sonication extraction. All extractions were performed at a flow rate of 2 mL/min for 60 minutes.
( ) = RSD for three replicate extractions.

Example 7

Supercritical Fluid Chromatography of Kavalactones—NH2 Column

In the second part of this study, various columns with the same dimensions, particle size (e.g. different stationary phases), and chromatography conditions were studied to optimize the SFC separation of kavalactones. An efficient analytical separation with supercritical fluid was felt to be advantageous in preparation for future scale-up work to isolate large quantities of each kavalactone.

Figure 25:
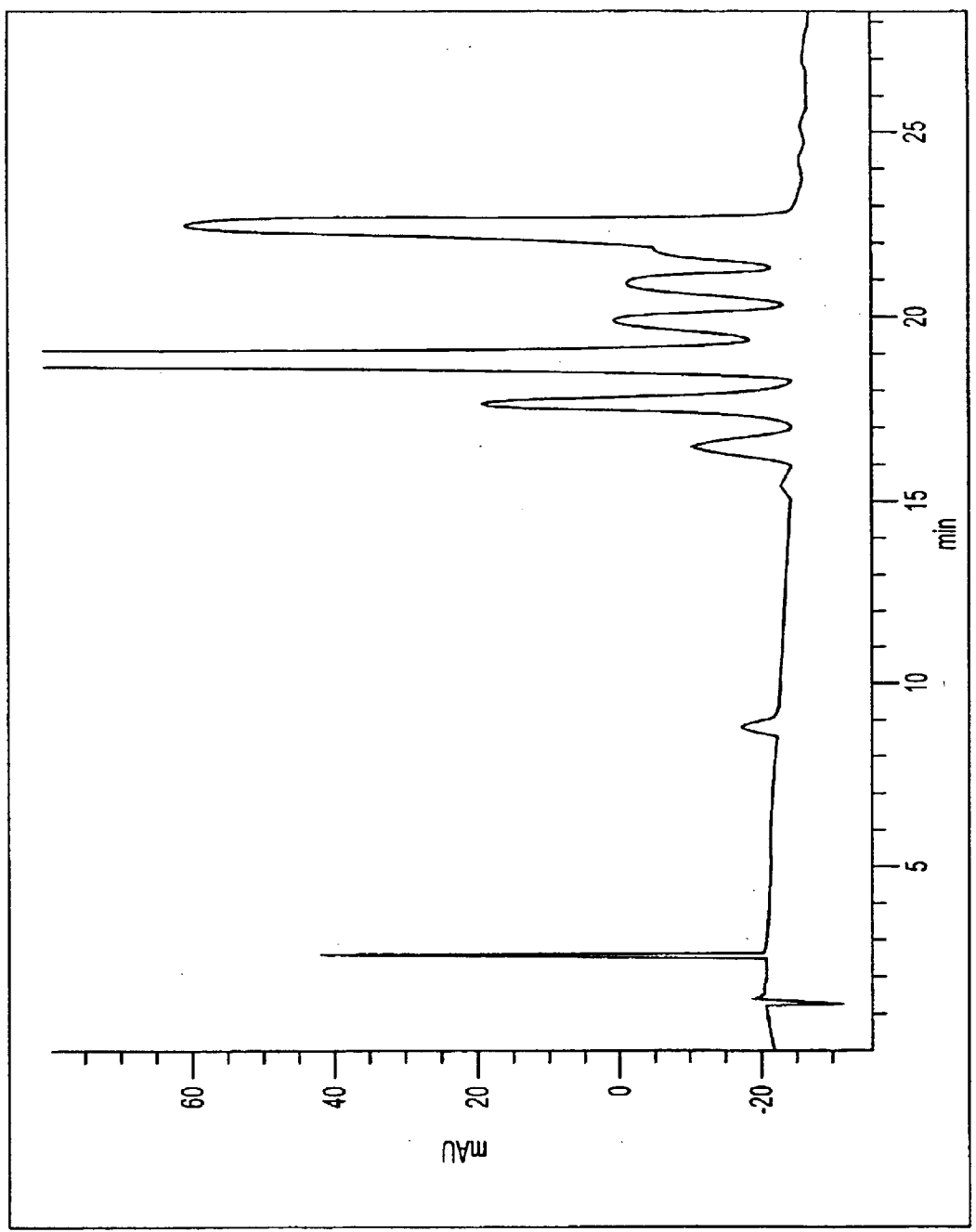
FIG. 25 SFC separation of kavalactone extract. Column $NH_2$ (250×4.6 mm, 5 μm dp). Pressure 125 atm, 60° C., 2 mL/min. Modifier program: 98/2% $CO_2/MeOH$ for 3 min. and then increased to 90/10 $CO_2/MeOH$ at rate of 9.4%/min.
Figure 26:
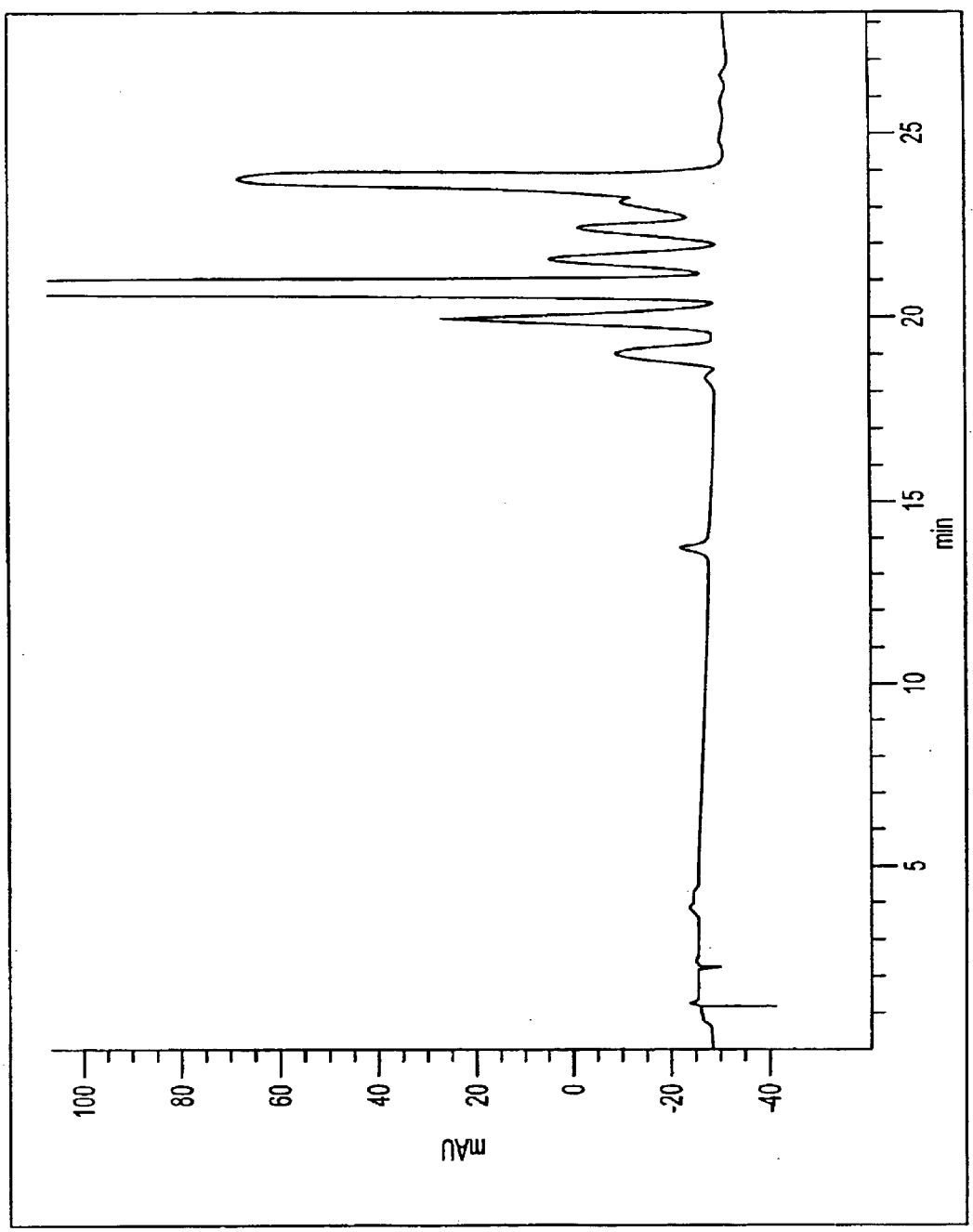
FIG. 26 SFC separation of kavalactone extract. Column $NH_2$ (250×4.6 mm, 5 μm dp). Pressure 125 atm, 80° C., 2 mL/min. Modifier program: 98/2% $CO_2/MeOH$ hold for 3 min. and then increased to 90/10 $CO_2/MeOH$ at rate of 0.4%/min.

FIG. 25 shows the separation of kavalactone extract using an Alltech Sperisorb NH2 column. Separation was obtained isobarically at 125 atm and 60° C. using a gradient of methanol-modified $CO_2$. The initial methanol concentration in $CO_2$ was 2% which was held constant for 3 minutes, and then MeOH was increased to 10% at a rate of 0.4%/minute. A separation of all kavalactones was obtained. However, the sixth peak eluted as a shoulder in front of the last major peak. To improve the separation of the later eluting components both lower and higher temperatures were tested. Lowering the column temperature to 40° C. caused co-elution of several peaks. Increasing the column temperature to 80° C. not only provided baseline separation (FIG. 26) for most of the kavalactones, but also higher resolution was obtained between peak 6 (tR=23.4 min). Increasing the pressure to 275 atm from 125 atm caused the kavalactones to elute as only four peaks. It appeared that peaks 1 and 2, peaks 4 and 5, and peaks 6 and 7 co-eluted; while peak 3 eluted as one major peak.

Figure 27:
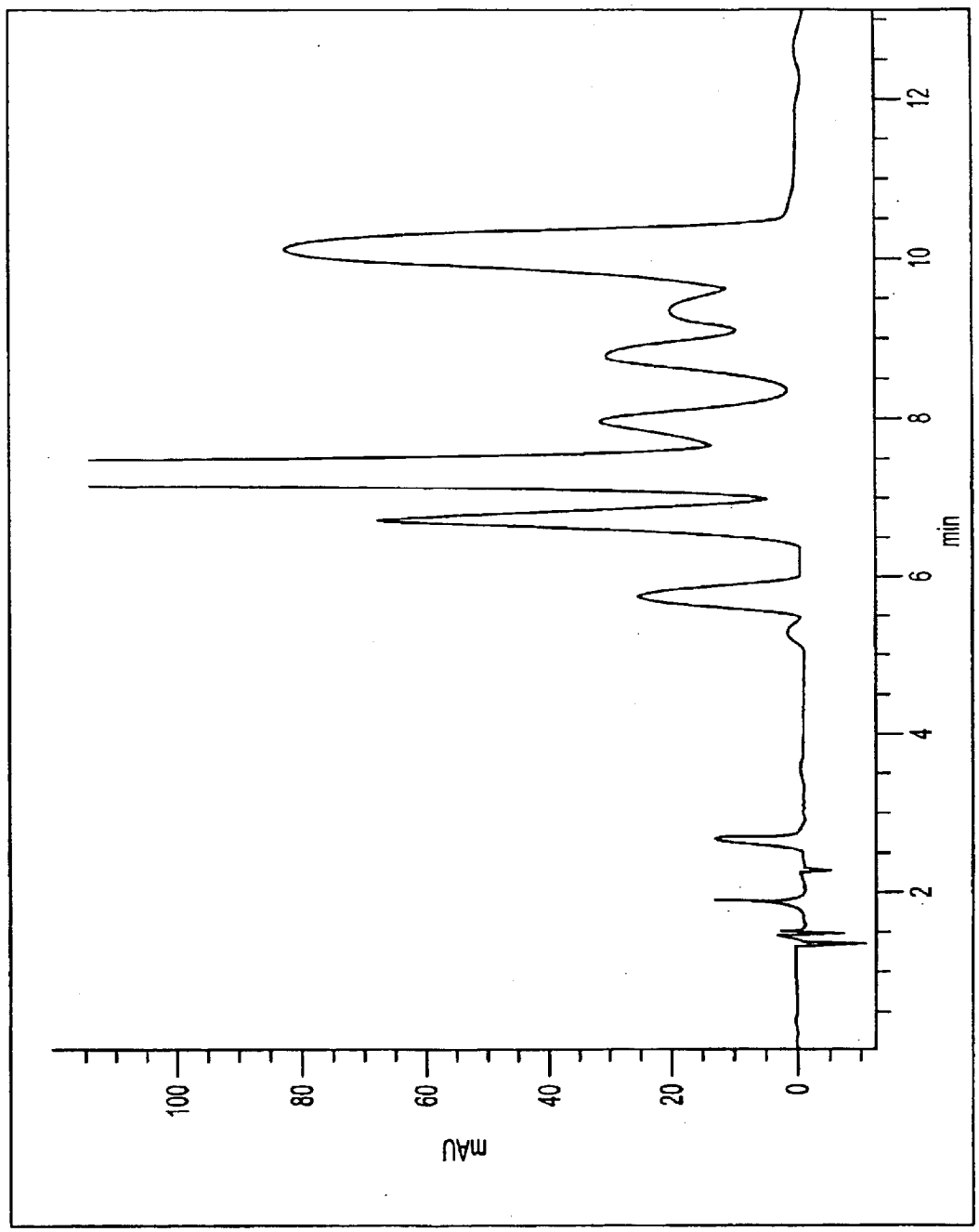
FIG. 27 SFC separation of kavalactone extract. Column $NH_2$ (250×4.6 mm, 5 μm dp). Pressure 125 atm, 60° C., 2 mL/min. Modifier program: 93/7% $CO_2/MeOH$ for 3 min. and then increased to 90/10% $CO_2/MeOH$ at rate of 0.2%/min.

Next, the modifier gradient was varied at 60° C. in order to not only obtain a better separation but also to obtain the analysis in a shorter time. For this purpose, the initial modifier concentration was increased to 7%. After three minutes the modifier concentration was increased to 10% at a rate of 0.2%/min. FIG. 27 shows the resulting separation. As can be observed, increasing the initial modifier concentration not only provided a faster separation (analysis time of 12 minutes vs. 25 minutes), but also provided a separation with higher resolution of the last two peaks.

Example 8

Supercritical Fluid Chromatography of Kavalactones—C4 Protein Column

Figure 28:
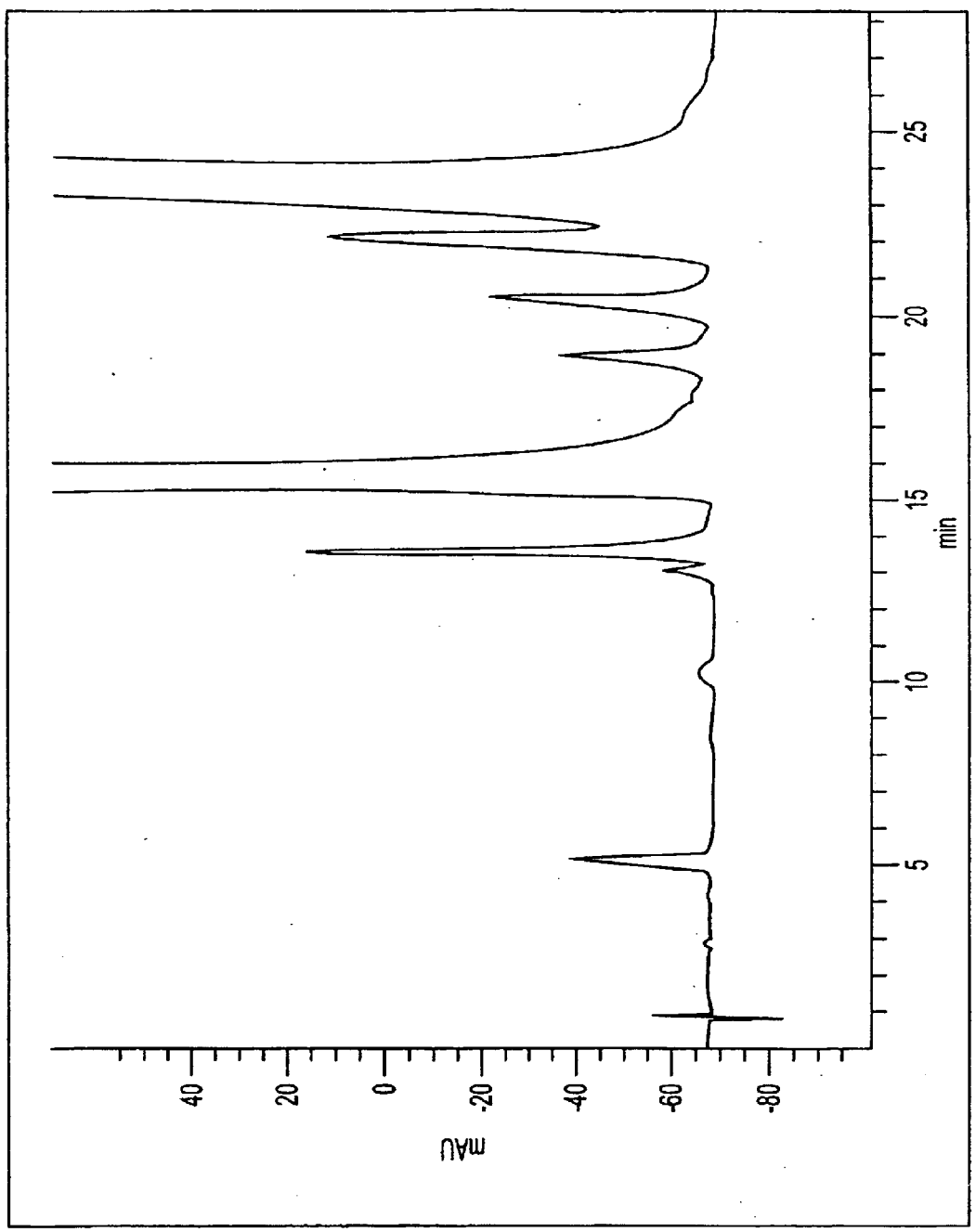
FIG. 28 SFC separation of kavalactone extract. Column protein C4 (250×4.6 mm, 5 μm dp). Pressure 125 atm, 100° C., 2 mL/min. Modifier program: 98.5/1.5%. $CO_2/MeOH$ for 2 min. and then increased to 90/10% $CO_2/MeOH$ at rate of 0.20%/min.
Figure 29:
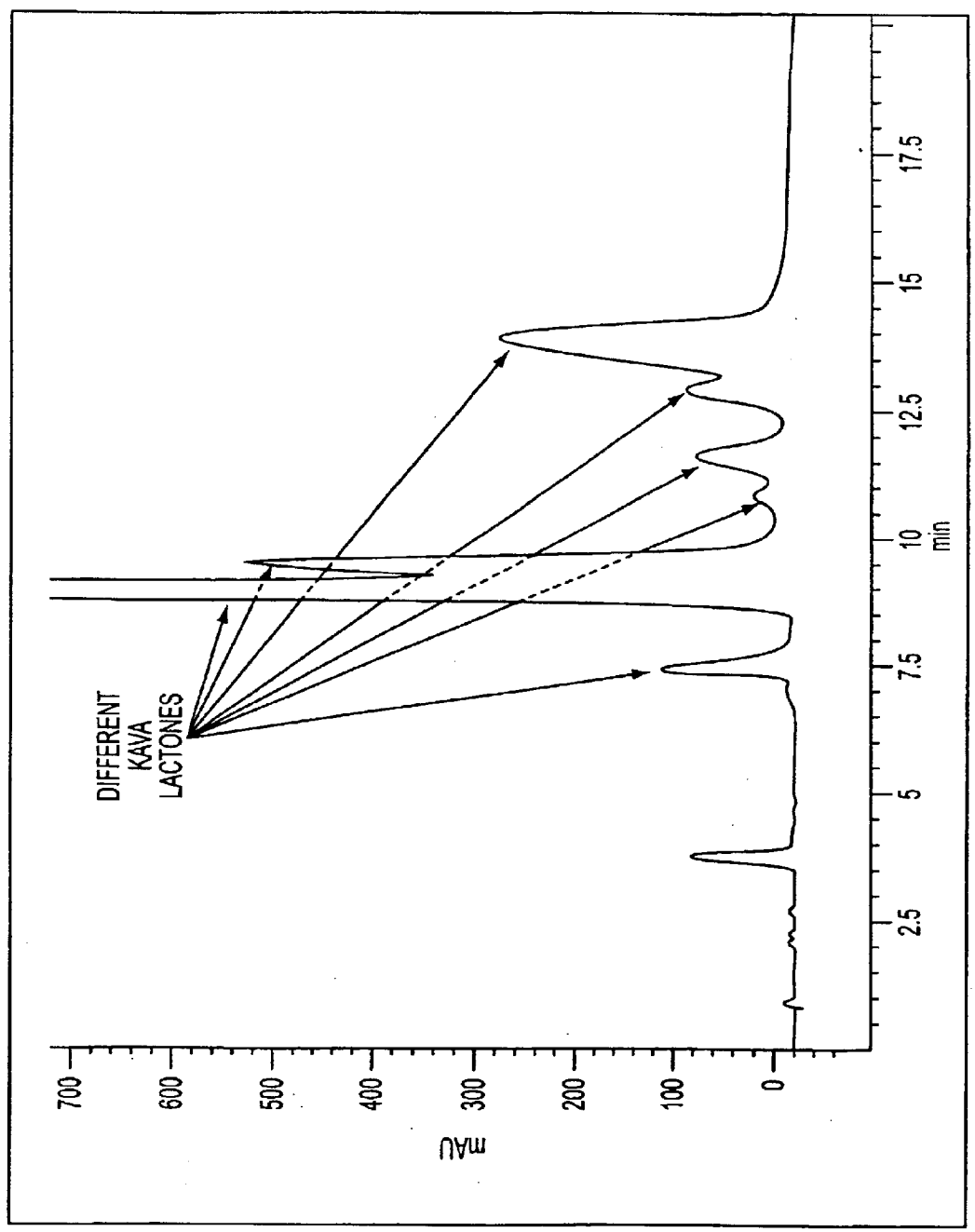
FIG. 29 SFC separation of kavalactone extract. Column protein C4 (250×4.6 mm, 5 μm dp). Pressure 125 atm, 80° C., 2.5 mL/min. Modifier program: 98/2% $CO_2/MeOH$ containing-0.1% isopropylamine for 3 min. and then increased to 90/10% $CO_2/MeOH$ at rate of 0.4%/min.

Most of the lactones co-eluted with a C4 protein column from Vatic using 125 atm, 70° C., 2 mL/min of liquid $CO_2$, and modifier programming (99/1% $CO_2$/MeOH hold for 4 minutes, and then increased to 97/3% $CO_2$/MeOH at rate of 0.1/min). Increasing the oven temperature to 80, 90 and 100° C. with a modifier program steadily improved the separation. FIG. 28 shows a separation of the kavalactone extract using 100° C. and 98.5/1.5% $CO_2$/MeOH as the initial mobile phase. Increasing the oven temperature provided baseline separation for most peaks. Increasing the density by increasing the column back pressure caused co-elution of several peaks. Decreasing the initial modifier concentration and the modifier gradient did not improve the separation at the higher pressure. Addition of 0.1% isopropyl amine (as a secondary modifier) to methanol prior to mixing in-line with CO2 not only improved separation of the lactones but it also decreased the analysis time. Isopropyl amine provided more selectivity to obtain a better separation (FIG. 29).

Example 9

SFC of Kavalactones—CN, DIOL and Diphenyl Columns

Figure 30:
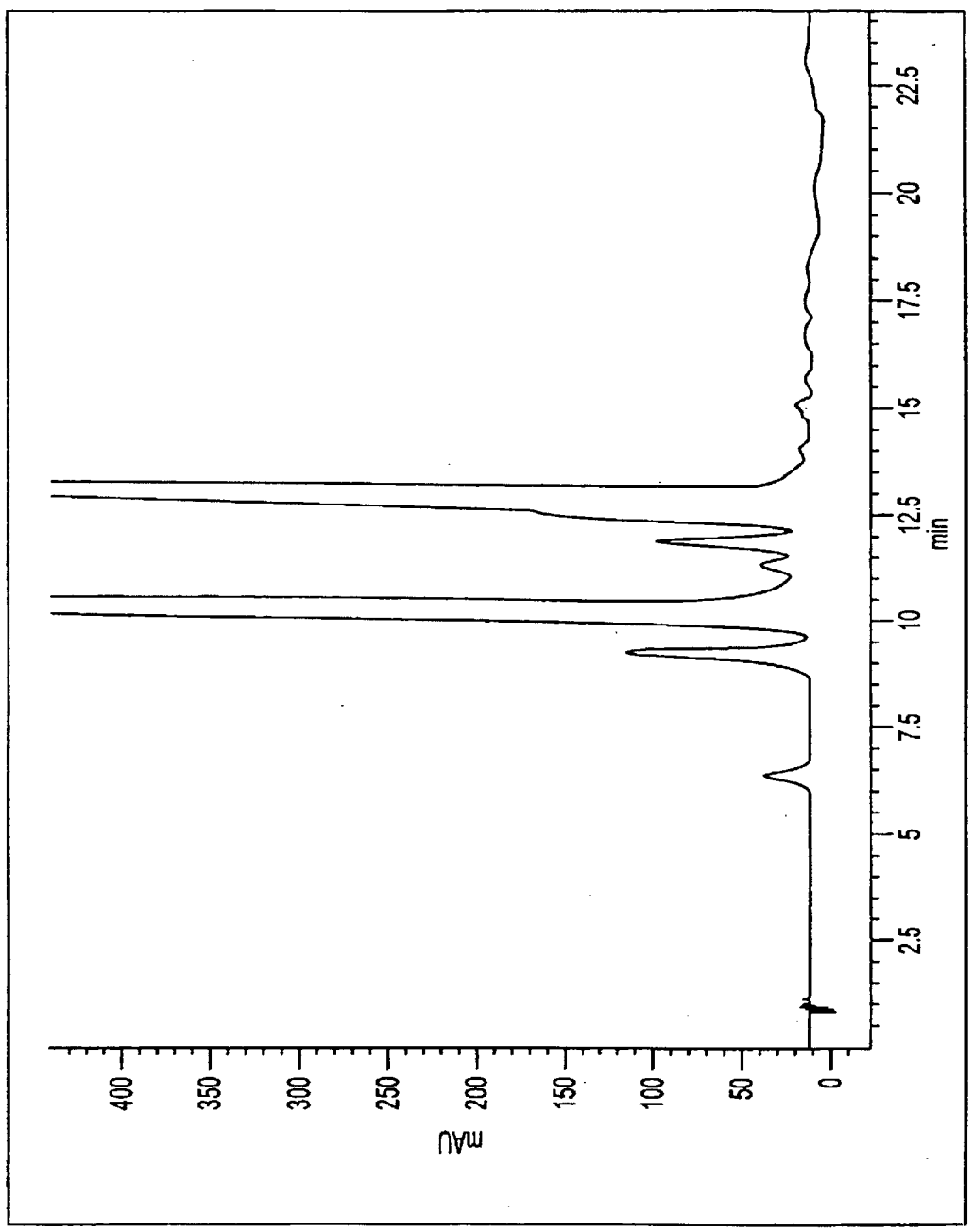
FIG. 30 SFC separation of kavalactone extract. Column diphenyl (250×4.6 mm, 5 μm dp). Pressure: 125 atm for 3 min. and then increased to 195 atm at rate of 5 atm/min, 80° C., 2 mL/min. Modifier program: 98/2% $CO_2/MeOH$, then increased to 93/7% $CO_2/MeOH$ at rate of 0.1%/min.

FIG. 30 shows the separation of the kavalactone extract on a Vatic diphenyl column. Unlike the other separations, the initial column back pressure was set to 125 atm for 3 minutes, which was increased to 195 atm at a rate of 5 atm/min. The initial mobile phase was 98/2% $CO_2$/MeOH which was increased to 93/7% $CO_2$/MeOH at a rate of 0.1%/min. The separation was obtained at 80° C. at a flow rate of 2 mL/min. Only five peaks were observed. Peaks 2 and 3 co-eluted as well as peaks 6 and 7.

Figure 31:
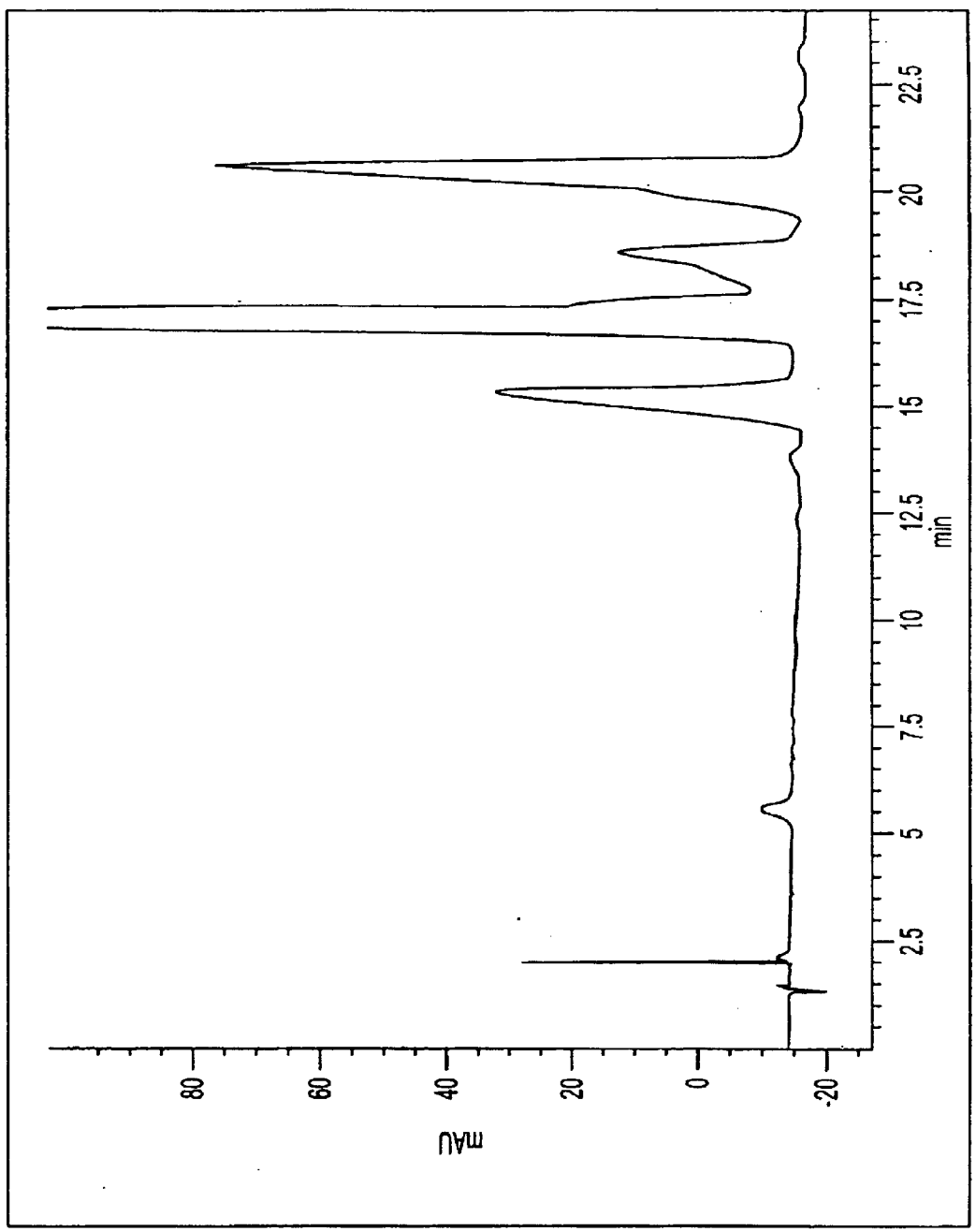
FIG. 31 SFC separation of kavalactone extract. Column CN (250×4.6 mm, 5 μm dp) Pressure 125 atm, 60° C., 2 mL/min. Modifier program: 98/2% $CO_2MeOH$ for 3 min. and then increased to 90/10% $CO_2/MeOH$ at rate of 0.4%/min.

FIG. 31 shows the SFC separation of kavalactones using an Altima CN column from Alltech at 125 atm, 60° C., and modifier programming starting with 98/2% $CO_2$/MeOH hold for 3 minutes and then increased to 90/10% $CO_2$/MeOH at a rate of 0.4%/min. As can be observed most of the analytes co-eluted. Increasing or decreasing either the temperature, pressure or modifier concentration failed to improve the separation. It is believed that this CN column did not have enough selectivity to resolve all the components.

Separation of the same extract on a Supelcosil DIOL column from Supleco was obtained. Chromatography conditions were 125 atm, 60° C., and a mobile phase composition of 98/2% $CO_2$/MeOH hold for 3 minutes and then increased to 90/10% $CO_2$/MeOH at a rate of 0.4%/minute. Separation was similar to those obtained via the CN column. Again, temperature and modifier composition did not have a major effect on the separation.

Results from evaluation of these columns showed that $NH_2$ and protein C4 columns provided (almost) baseline separation of all kavalactones. However, it was believed that most of the peaks were resolved much better with the protein C4 column compared to the $NH_2$ column. Therefore, the protein C4 stationary phase was used to perform the semi-preparative separations.

Example 10

Semi-preparative Separation

Figure 32:
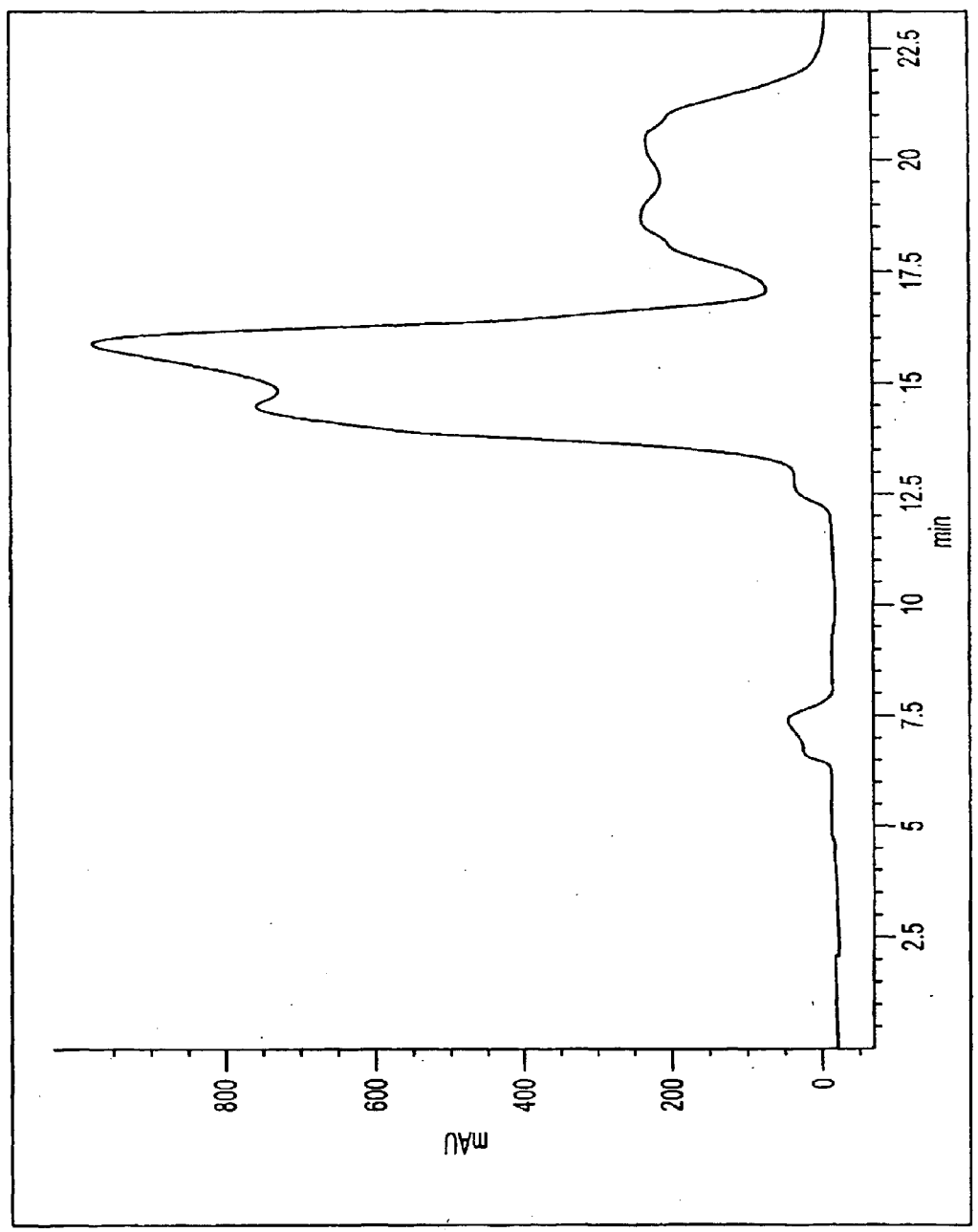
FIG. 32 Semi-preparative SFC separation of kavalactone extract. column a single protein C4 (250×4.6 mm, 5 μm dp). Pressure 125 atm, 80° C., 4 mL/min. Modifier program: 98/2% $CO_2/MeOH$ containing 0.1% isopropylamine for 3 min. and then increased to 90/10% $CO_2/MeOH$ at rate of 0.4%/min.
Figure 33:
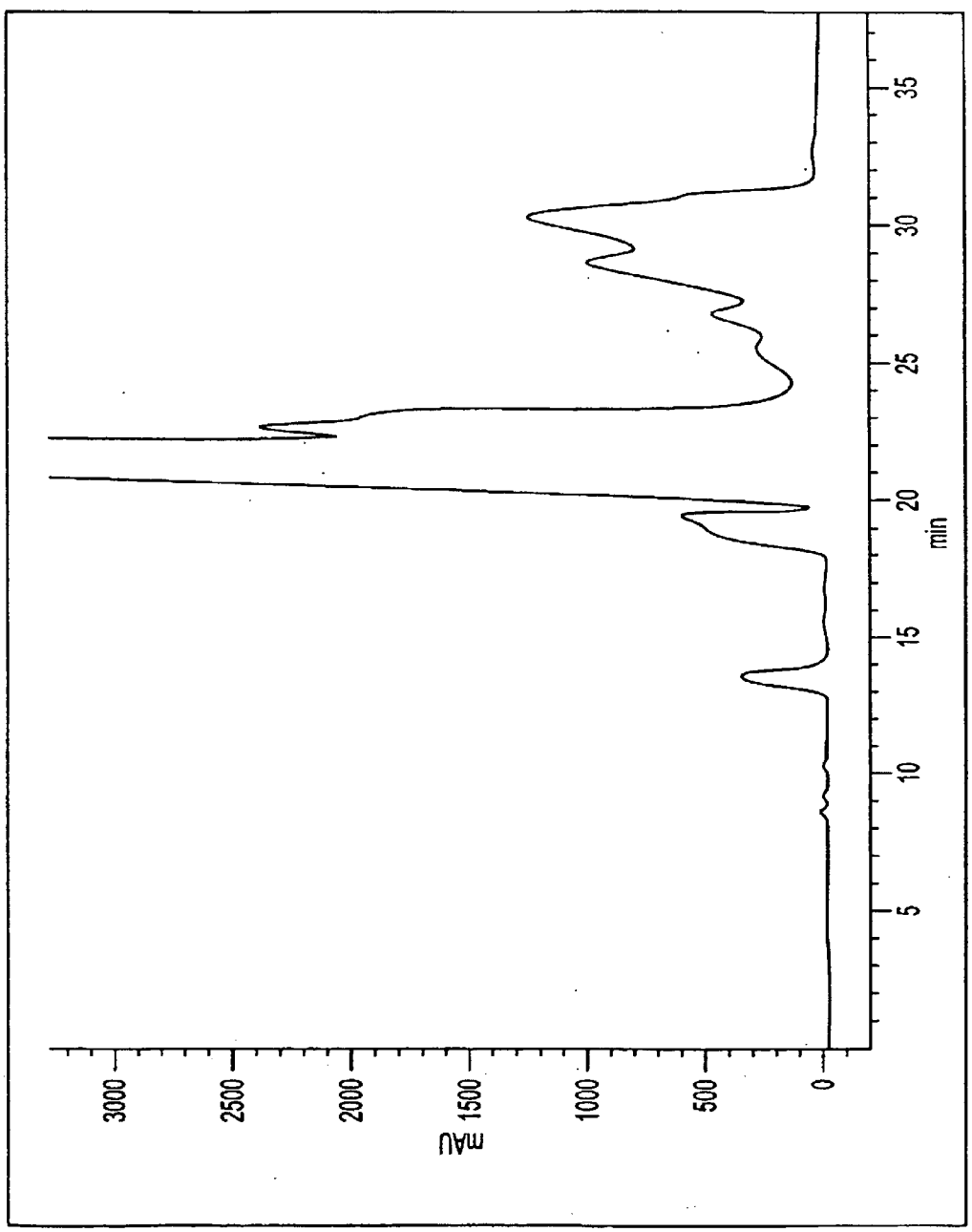
FIG. 33 Semi-preparative SFC separation of kavalactone extract. Column two protein C4 (250×4.6 mm, 5 μm dp) in series. Pressure 125 atm, 80° C., 4 mL/min. Modifier program: 98/2% $CO_2$,/MeOH containing 0.1% isopropylamine for 3 min. increased to 90/10% $CO_2/MeOH$ at rate of 0.4%/min. Injection volume −50 μL (100 μg/μL).

Semi-preparative separation of kavalactones was first tried using a single protein C4 column, 250×10 mm, 5 μm dp. Parameters were changed to optimize the separation. The optimized separation employed 125 atm, 80° C., and a flow rate of 4 mL/min using a gradient of methanol-modified $CO_2$ (FIG. 32). Results showed that a single protein C4 column did not have enough efficiency to separate all the kavalactones in the semi-preparative mode. Next, two semi-preparative protein C4 columns were connected in series to obtain the separation. FIG. 33 shows the separation of the kavalactone extract (injection volume 5 mg) using the previously stated conditions. As can be observed baseline separation of most of the kavalactones, in semi-preparative scale, were achieved-using two columns connected in series.

Extraction of different kavalactones with efficiency greater than 90% was obtained using pure $CO_2$. However, higher extraction efficiency was obtained using 15% ethanol modified $CO_2$. Also, separation of different kavalactones from Kava root extract was performed using methanol modified supercritical $CO_2$. Results showed that separation of different kavalactones can be obtained using analytical scale amino and protein C4 columns. Semi-preparative separation of kavalactones was carried-out using two protein C4 columns connected in series. Baseline separation for most of the components were obtained.

Other embodiments and uses of the invention will be apparent to those skilled in the art from consideration of the specification and practice of the invention disclosed herein. All references cited herein, including all U.S. and foreign patents and patent applications including U.S. provisional patent applications serial Nos. 60/102,912, 60/122,526 and 60/136,409, and U.S. patent application Ser. Nos. 09/408, 922 and 09/518,191, are specifically and entirely incorporated by reference. It is intended that the specification and examples be considered exemplary only, with the true scope and spirit of the invention indicated by the following claims.

What is claimed is:

1. A method for obtaining bioactive substances from plant material, comprising:
   mechanically disrupting plant material comprising kava root;
   contacting the disrupted material with a supercritical fluid containing carbon dioxide, an alcohol and an isopropyl amine, and separating the bioactive substances there from by supercritical fluid chromatography; and
   collecting the bioactive substances with a resin trap.

2. The method of claim 1, wherein mechanically disrupting comprises grinding, crushing, macerating or a combination thereof.

3. The method of claim 1, wherein the disrupted material is contacted with the supercritical fluid at a minimum pressure of between 200 and 400 bar, and a maximum pressure of between 400 and 600 bar.

4. The method of claim 1, wherein the supercritical fluid chromatography comprises passing the supercritical fluid through an $NH_2$ column.

5. The method of claim 1, wherein the resin trap is a C-18 resin.

6. The method of claim 1, wherein the column is maintained at a temperature of at least 90 degrees centigrade.

7. A method for obtaining a kawain or a methysticin from a kava root, comprising:
   mechanically disrupting the kava root;
   contacting the disrupted material with a supercritical fluid containing carbon dioxide, an alcohol and an isopropyl amine at a pressure of at least 350 atmospheres and separating substances there from by supercritical fluid chromatography;
   collecting the substances with a resin trap; and
   eluting the kawain or the methysticin from said substances.

8. The method of claim 7, wherein the alcohol is an ethanol and said ethanol comprises at least 15% of said supercritical fluid.

9. The method of claim 7, wherein the supercritical fluid chromatography is carried out at a temperature of at least 60 degrees centigrade.

10. The method of claim 7, wherein the pressure is maintained between 350 to 450 atmospheres.

11. The method of claim 7, wherein the supercritical fluid chromatography is carried out at a temperature of at least 90 degrees centigrade.

12. A method for obtaining a kavalactone from kava root, comprising:
   mechanically disrupting a material containing kava root;
   contacting the disrupted material with supercritical fluid containing carbon dioxide, an alcohol and an isopropyl amine, at a pressure of at least 275 atmospheres and separating the substances by supercritical fluid chromatography over an $NH_2$ column;
   collecting the kavalactone with a resin trap.

13. The method of claim 12, wherein 15% by volume of the super critical fluid is ethanol.

14. The method of claim 12, wherein the kavalactone is purified by supercritical fluid chromatography over another $NH_2$ column.

15. The method of claim 12, wherein the $NH_2$ column is operated at a temperature above 40 degrees centigrade.

16. The method of claim 12, wherein the supercritical fluid chromatography comprises a gradient of from 7% to 10% methanol.

17. The method of claim 12, wherein the column is maintained at a temperature of at least 90 degrees centigrade.

18. A method for obtaining bioactive substances from a plant material, comprising:
   mechanically disrupting plant material comprising kava root;
   contacting the disrupted material with a supercritical fluid containing isopropyl amine, carbon dioxide and an alcohol;
   collecting the bioactive substances with a resin trap;
   eluting the bioactive substances from the resin trap by supercritical fluid chromatography over an $NH_2$ column.

19. The method of claim 18, wherein the isopropyl amine is mixed into the alcohol prior to mixing the alcohol with the carbon dioxide.

20. The method of claim 18, wherein the column is maintained at a temperature of at least 90 degrees centigrade.

21. The method of claim 18, wherein mechanically disrupting comprises grinding, crushing, macerating or a combination thereof.

* * * * *